(12) United States Patent
Gusmeroli et al.

(10) Patent No.: US 11,365,175 B2
(45) Date of Patent: Jun. 21, 2022

(54) AROMATIC AMIDES HAVING A FUNGICIDAL ACTIVITY, THEIR AGRONOMIC COMPOSITIONS AND RELATIVE PREPARATION METHOD

(71) Applicant: ISAGRO S.p.A., Milan (IT)

(72) Inventors: Marilena Gusmeroli, Monza (IT);
Paolo Bellandi, Carcare (IT); Silvia Mormile, Novara (IT); Paolo Boggio, Turin (IT); Paolo Bravini, Novara (IT); Matteo Vazzola, Cogliate (IT); Christian Badaracco, Vittuone (IT); Riccardo Liguori, Monza (IT)

(73) Assignee: ISAGRO S.P.A., Milan (IT)

( * ) Notice: Subject to any disclaimer, the term of this patent is extended or adjusted under 35 U.S.C. 154(b) by 235 days.

(21) Appl. No.: 16/760,056

(22) PCT Filed: Nov. 2, 2018

(86) PCT No.: PCT/IB2018/058629
§ 371 (c)(1),
(2) Date: Apr. 29, 2020

(87) PCT Pub. No.: WO2019/087145
PCT Pub. Date: May 9, 2019

(65) Prior Publication Data
US 2020/0354314 A1    Nov. 12, 2020

(30) Foreign Application Priority Data

Nov. 3, 2017   (IT) .................. 102017000125037

(51) Int. Cl.
| | |
|---|---|
| *C07C 327/34* | (2006.01) |
| *A01N 37/40* | (2006.01) |
| *A01N 37/44* | (2006.01) |
| *A01N 55/00* | (2006.01) |
| *C07C 233/18* | (2006.01) |
| *C07C 323/63* | (2006.01) |
| *C07F 7/08* | (2006.01) |
| *C07D 309/12* | (2006.01) |
| *C07C 323/62* | (2006.01) |
| *C07F 7/18* | (2006.01) |
| *C07C 237/44* | (2006.01) |

(52) U.S. Cl.
CPC ............ *C07C 327/34* (2013.01); *A01N 37/40* (2013.01); *A01N 37/44* (2013.01); *A01N 55/00* (2013.01); *C07C 233/18* (2013.01); *C07C 237/44* (2013.01); *C07C 323/63* (2013.01)

(58) Field of Classification Search
CPC ... C07C 327/34; C07C 233/18; C07C 237/44; C07C 232/63; C07C 2601/02; C07C 2601/14; C07C 2601/18; C07C 2601/20; C07C 2602/42; C07C 2603/74; C07C 323/62; A01N 37/40; A01N 37/44; A01N 55/00; C07F 7/081; C07F 7/1804; C07D 309/12
See application file for complete search history.

(56) References Cited

FOREIGN PATENT DOCUMENTS

| EP | 2277869 A1 | 1/2011 |
|---|---|---|
| WO | 99/27783 A1 | 6/1999 |
| WO | 01/05769 A2 | 1/2001 |
| WO | 01/12587 A1 | 2/2001 |
| WO | 01/14339 A2 | 3/2001 |

OTHER PUBLICATIONS

Moriggi, J., "International Search Report and Written Opinion of the International Searching Authority for PCT/IB2018/058629," European Patent Office, dated Mar. 27, 2019.

*Primary Examiner* — Trevor Love
(74) *Attorney, Agent, or Firm* — Florek & Endres PLLC

(57) ABSTRACT

Aromatic amides are described, having general formula (I):

suitably substituted and having a high fungicidal activity, together with their use for controlling phytopathogenic fungi of important agricultural crops.

17 Claims, No Drawings

AROMATIC AMIDES HAVING A FUNGICIDAL ACTIVITY, THEIR AGRONOMIC COMPOSITIONS AND RELATIVE PREPARATION METHOD

The present invention relates to aromatic amides having a high fungicidal activity; in particular, it relates to amides suitably substituted having a high fungicidal activity and their use for the control of phytopathogenic fungi of important agricultural crops. Aromatic amides having a fungicidal activity are already known and in particular are described in patent applications WO9/27783, WO01/14339, WO01/12587 and WO01/05769.

The products described in these documents, however, are often unsatisfactory in terms of effectiveness with respect to various phytopathogenic fungi of interest in important agricultural crops.

The Applicant has now surprisingly found that the combination of specific substituents on the aromatic ring of these amides allows the spectrum of action already known previously on analogous compounds to be broadened, without demonstrating symptoms of phytotoxicity in the agricultural crops of interest.

The object of the present invention therefore relates to new amides having general formula (I):

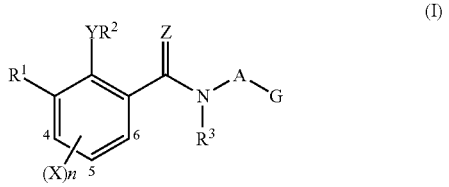

wherein:

$R^1$ represents a $C_1$-$C_{12}$ alkoxyl, a $C_1$-$C_{12}$ haloalkoxyl, a $C_3$-$C_{18}$ cycloalkoxyl, a —$NR^4R^5$ group;

$R^2$ represents a hydrogen atom, a $C_2$-$C_{13}$ acyl, a $C_2$-$C_{12}$ alkanoyloxyalkyl $C_1$-$C_{12}$, a $C_2$-$C_{12}$ haloalkanoyloxyalkyl $C_1$-$C_{12}$, a $C_1$-$C_{12}$ alkoxy-$C_1$-$C_{12}$-alkanoyloxyalkyl $C_1$-$C_{12}$, a $C_1$-$C_{12}$ haloalkoxy-$C_1$-$C_{12}$-alkanoyloxyalkyl $C_1$-$C_{12}$, a $C_3$-$C_{18}$ cycloalkoxy-$C_1$-$C_{12}$-alkanoyloxyalkyl $C_1$-$C_{12}$, an aryloxy $C_1$-$C_{12}$ alkanoyloxyalkyl $C_1$-$C_{12}$, a benzyloxy $C_1$-$C_{12}$ alkanoyloxyalkyl $C_1$-$C_{12}$, a $C_4$-$C_{18}$ cycloalkanoyloxyalkyl $C_1$-$C_{12}$, a $C_1$-$C_{12}$ aroyloxyalkyl, a $C_1$-$C_{12}$ benzoyloxyalkyl, a $C_1$-$C_{12}$ heterocyclylcarbonyloxyalkyl, a $C_1$-$C_{12}$ alkyloxyalkyl $C_1$-$C_{12}$, a $C_1$-$C_{12}$ haloalkyloxyalkyl $C_1$-$C_2$, a $C_1$-$C_{12}$ alkoxy-$C_1$-$C_{12}$-alkyloxyalkyl $C_1$-$C_2$, a $C_1$-$C_{12}$ haloalkoxy-$C_1$-$C_{12}$-alkyloxyalkyl $C_1$-$C_{12}$, a $C_3$-$C_{18}$ cycloalkoxy $C_1$-$C_{12}$-alkyloxyalkyl $C_1$-$C_{12}$, an aryloxy $C_1$-$C_{12}$-alkyloxyalkyl $C_1$-$C_{12}$, a benzyloxy $C_1$-$C_{12}$-alkyloxyalkyl $C_1$-$C_{12}$, a $C_3$-$C_{18}$ cycloalkyloxyalkyl $C_1$-$C_{12}$, a $C_1$-$C_{12}$ aryloxyalkyl, a $C_1$-$C_{12}$ benzyloxyalkyl; a $C_1$-$C_{12}$ heterocyclyloxyalkyl, a $C_4$-$C_{12}$ alkanoylthioalkyl $C_1$-$C_{12}$, a $C_2$-$C_{12}$ haloalkanoylthioalkyl $C_1$-$C_{12}$, a $C_4$-$C_{18}$ cycloalkanoylthioalkyl $C_1$-$C_{12}$, a $C_1$-$C_{12}$ aroylthioalkyl, a $C_1$-$C_{12}$ benzoylthioalkyl; a $C_1$-$C_{12}$ heterocyclylcarbonylthioalkyl, a $C_1$-$C_{12}$ alkylthioalkyl $C_1$-$C_{12}$, a $C_1$-$C_{12}$ haloalkylthioalkyl $C_1$-$C_{12}$, a $C_1$-$C_{12}$ alkoxy-$C_1$-$C_{12}$-alkylthioalkyl $C_1$-$C_{12}$, a $C_1$-$C_{12}$ haloalkoxy-$C_1$-$C_{12}$-alkylthioalkyl $C_1$-$C_{12}$, a $C_3$-$C_{18}$ cycloalkoxy $C_1$-$C_{12}$-alkylthioalkyl $C_1$-$C_2$, a $C_1$-$C_{12}$ aryloxy alkylthioalkyl $C_1$-$C_{12}$, a $C_1$-$C_{12}$ benzyloxy alkylthioalkyl $C_1$-$C_{12}$, a $C_3$-$C_{18}$ cycloalkylthioalkyl $C_1$-$C_{12}$, a $C_1$-$C_{12}$ benzylthioalkyl, a $C_1$-$C_{12}$ arylthioalkyl, a $C_1$-$C_{12}$ heterocyclylthioalkyl, a $C_2$-$C_{12}$ alkanoylaminoalkyl $C_1$-$C_{12}$, a $C_2$-$C_{12}$ haloalkanoylaminoalkyl $C_1$-$C_{12}$, a $C_4$-$C_{18}$ cycloalkanoylaminoalkyl $C_1$-$C_{12}$, a $C_1$-$C_{12}$ aroylaminoalkyl, a $C_1$-$C_{12}$ benzoylaminoalkyl, a $C_1$-$C_{12}$ heterocyclylcarbonylaminoalkyl, a $C_1$-$C_{12}$ heterocyclylaminoalkyl, a $C_4$-$C_{18}$ cycloalkylaminoalkyl $C_1$-$C_{12}$, a tetrahydropyranyl, a $C_1$-$C_{12}$ trimethylsilyloxyalkyl, a $C_1$-$C_{12}$ trimethylsilyl-ethoxyalkyl;

$R^1$ and $R^2$ together with the carbon atoms to which they are bound can form a 1,3-oxazole ring;

$R^3$ represents a hydrogen atom, a $C_1$-$C_{12}$ alkyl, a $C_3$-$C_8$ cycloalkyl;

$R^4$ and $R^5$, the same or different, represent a hydrogen atom, an aminocarbonyl group, a methylaminocarbonyl group, a dimethylaminocarbonyl group, a $C_1$-$C_{12}$ alkyl, a formyl, a $C_2$-$C_{13}$ acyl, a $C_2$-$C_{13}$ haloalkylcarbonyl, a benzyl group, an aroyl group, a $C_2$-$C_{13}$ alkoxycarbonyl, a $C_1$-$C_{12}$ alkoxyalkyl $C_1$-$C_{12}$; a $C_1$-$C_{12}$ alkanoyloxyalkyl $C_1$-$C_{12}$, a $C_1$-$C_{12}$ haloalkanoyloxyalkyl $C_1$-$C_{12}$, a $C_3$-$C_{18}$ cycloalkanoyloxyalkyl $C_1$-$C_{12}$, a $C_1$-$C_{12}$ aroyloxyalkyl, a $C_1$-$C_{12}$ heterocyclylcarbonyloxyalkyl, a $C_1$-$C_{12}$ aryloxyalkyl, a $C_1$-$C_{12}$ heterocyclyloxyalkyl, a $C_1$-$C_{12}$ alkanoylthioalkyl $C_1$-$C_{12}$, a $C_1$-$C_{12}$ halo-alkanoylthioalkyl $C_1$-$C_{12}$, a $C_3$-$C_{18}$ cycloalkanoylthioalkyl $C_1$-$C_{12}$, a $C_1$-$C_{12}$ aroylthioalkyl, a $C_1$-$C_{12}$ heterocyclylthioalkyl, a $C_1$-$C_{12}$ arylthioalkyl, a $C_1$-$C_{12}$ alkanoylaminoalkyl $C_1$-$C_{12}$, a $C_1$-$C_{12}$ haloalkanoylaminoalkyl $C_1$-$C_{12}$, a $C_3$-$C_{18}$ cycloalkanoylaminoalkyl $C_1$-$C_{12}$, a $C_1$-$C_{12}$ aroylaminoalkyl, a $C_1$-$C_{12}$ heterocyclylaminoalkyl;

A represents a direct bond or a $C_1$-$C_{12}$ alkyl;

Y represents an oxygen or sulfur atom;

Z represents an oxygen or sulfur atom;

X represents a halogen atom, a CN group, a $NO_2$ group;

n represents a number ranging from 0 to 3;

G represents a $C_3$-$C_{18}$ cycloalkyl containing from 0 to 3 heteroatoms selected from O, N, S, a $C_3$-$C_{18}$ cycloalkenyl containing from 1 to 3 unsaturations and from 0 to 3 heteroatoms selected from O, N, S, a $C_6$-$C_{20}$ bicycloalkyl containing from 0 to 3 heteroatoms selected from O, N, S, a $C_6$-$C_{20}$ bicycloalkenyl containing from 1 to 3 unsaturations and from 0 to 3 heteroatoms selected from O, N, S, adamantyl, said cyclic groups being optionally substituted with 1 to 3 groups, the same or different, selected from $C_1$-$C_6$ alkyl, $C_3$-$C_{12}$ cycloalkyl, benzyl and with the possibility of incorporating in said cyclic structure a group selected from: C=O, C(=O)O, C(=O)S, C(=S)O, C(=S)S, C(=O)$NR^3$;

with the proviso that if $R^1$ represents a —$NR^4R^5$ group wherein $R^4$ is a hydrogen atom and $R^5$ is an aminocarbonyl group, a methylaminocarbonyl group, a dimethylaminocarbonyl group, a formyl, a $C_2$-$C_{13}$ acyl, a $C_2$-$C_{13}$ alkoxycarbonyl, and $R^2$ and $R^3$ represent a hydrogen atom, and Y is an oxygen atom, G cannot be a $C_3$-$C_{12}$ cycloalkyl, a $C_3$-$C_{12}$ cycloalkenyl and a $C_3$-$C_8$ cycloalkyl containing from 0 to 3 heteroatoms selected from O, N, S. Amides having formula (I) are preferred wherein:

$R^1$ represents a $C_1$-$C_6$ alkoxyl, a $C_1$-$C_6$ halohaloalkoxyl, a $C_3$-$C_{12}$ cycloalkoxyl, a —$NR^4R^5$ group;

$R^2$ represents a hydrogen atom, a $C_2$-$C_7$ acyl, a $C_2$-$C_7$ alkanoyloxyalkyl $C_1$-$C_6$, a $C_2$-$C_7$ haloalkanoyloxyalkyl $C_1$-$C_6$, a $C_1$-$C_6$ alkoxy-$C_1$-$C_6$-alkanoyloxyalkyl $C_1$-$C_6$, a $C_1$-$C_6$ haloalkoxy-$C_1$-$C_6$-alkanoyloxyalkyl $C_1$-$C_6$, a $C_3$-$C_{12}$ cycloalkoxy-$C_1$-$C_6$-alkanoyloxyalkyl $C_1$-$C_6$, an aryloxy $C_1$-$C_6$ alkanoyloxyalkyl $C_1$-$C_6$, a benzyloxy $C_1$-$C_6$ alkanoyloxyalkyl $C_1$-$C_6$, a $C_4$-$C_{12}$ cycloalkanoyloxyalkyl $C_1$-$C_6$, a $C_1$-$C_6$ aroyloxyalkyl, a $C_1$-$C_6$ benzoyloxyalkyl, a $C_1$-$C_6$ heterocyclylcarbonyloxyalkyl, a $C_1$-$C_6$ alkyloxyalkyl $C_1$-$C_6$, a $C_1$-$C_6$ haloalkyloxyalkyl $C_1$-$C_6$, a $C_1$-$C_6$ alkoxy-$C_1$-$C_6$-alkyloxyalkyl $C_1$-$C_6$, a $C_1$-$C_6$ haloalkoxy-$C_1$-$C_6$-alkyloxyalkyl $C_1$-$C_6$, a $C_3$-$C_{12}$ cycloalkoxy $C_1$-$C_6$-alkyloxyalkyl $C_1$-$C_6$, an aryloxy $C_1$-$C_6$-alkyloxyalkyl $C_1$-$C_6$, a benzyloxy $C_1$-$C_6$-alkyloxyalkyl $C_1$-$C_6$, a $C_3$-$C_{12}$ cycloalkyloxyalkyl $C_1$-$C_6$, a $C_1$-$C_6$ aryloxyalkyl, a $C_1$-$C_6$ benzyloxyalkyl; a $C_1$-$C_6$ heterocyclyloxyalkyl, a $C_4$-$C_6$ alkanoylthioalkyl $C_1$-$C_6$, a $C_2$-$C_6$ haloalkanoylthioalkyl $C_1$-$C_6$, a $C_4$-$C_{12}$ cycloalkanoylthioalkyl $C_1$-$C_6$, a $C_1$-$C_6$ aroylthioalkyl, a $C_1$-$C_6$ benzoylthioalkyl; a $C_1$-$C_6$ heterocyclylcarbonylthioalkyl, a $C_1$-$C_6$ alkylthioalkyl $C_1$-$C_6$, a $C_1$-$C_6$ haloalkylthioalkyl $C_1$-$C_6$, a $C_1$-$C_6$ alkoxy-$C_1$-$C_6$-alkylthioalkyl $C_1$-$C_6$, a $C_1$-$C_6$ haloalkoxy-$C_1$-$C_6$-alkylthioalkyl $C_1$-$C_6$, a $C_3$-$C_{12}$ cycloalkoxy $C_1$-$C_6$ alkylthioalkyl $C_1$-$C_6$, a $C_1$-$C_6$ aryloxy alkylthioalkyl $C_1$-$C_6$, a $C_1$-$C_6$ benzyloxy alkylthioalkyl $C_1$-$C_6$, a $C_3$-$C_{12}$cycloalkylthioalkyl $C_1$-$C_6$, a $C_1$-$C_6$ benzylthioalkyl, a $C_1$-$C_6$ arylthioalkyl, a $C_1$-$C_6$ heterocyclylthioalkyl, a $C_2$-$C_6$ alkanoylaminoalkyl $C_1$-$C_6$, a $C_2$-$C_6$ haloalkanoylaminoalkyl $C_1$-$C_6$, a $C_4$-$C_{12}$ cycloalkanoylaminoalkyl $C_1$-$C_6$, a $C_1$-$C_6$ aroylaminoalkyl, a $C_1$-$C_6$ benzoylaminoalkyl, a $C_1$-$C_6$ heterocyclylcarbonylaminoalkyl, a $C_1$-$C_6$ heterocyclylaminoalkyl, a $C_4$-$C_{12}$ cycloalkylaminoalkyl $C_1$-$C_6$, a tetrahydropyranyl, a $C_1$-$C_6$ trimethylsilyloxyalkyl, a $C_1$-$C_6$ trimethylsilyl-ethoxyalkyl;

$R^3$ represents a hydrogen atom, a $C_1$-$C_6$ alkyl, a $C_3$-$C_{12}$ cycloalkyl;

$R^4$ and $R^5$, the same or different, represent a hydrogen atom, an aminocarbonyl group, a methylaminocarbonyl group, a dimethylaminocarbonyl group, a $C_1$-$C_6$ alkyl, a formyl, a $C_2$-$C_7$ acyl, a $C_2$-$C_7$ haloalkylcarbonyl, a benzyl group, an aroyl group, a $C_2$-$C_7$ alkoxycarbonyl, a $C_1$-$C_6$ alkoxyalkyl $C_1$-$C_6$; a $C_1$-$C_6$ alkanoyloxyalkyl $C_1$-$C_6$, a $C_1$-$C_6$ haloalkanoyloxyalkyl $C_1$-$C_{12}$, a $C_3$-$C_{12}$ cycloalkanoyloxyalkyl $C_1$-$C_6$, a $C_1$-$C_6$ aroyloxyalkyl, a $C_1$-$C_6$ heterocyclylcarbonyloxyalkyl, a $C_1$-$C_6$ aryloxyalkyl, a $C_1$-$C_6$ heterocyclyloxyalkyl, a $C_1$-$C_6$ alkanoylthioalkyl $C_1$-$C_6$, a $C_1$-$C_6$ haloalkanoylthioalkyl $C_1$-$C_6$, a $C_3$-$C_{12}$ cycloalkanoylthioalkyl $C_1$-$C_6$, a $C_1$-$C_6$ aroylthioalkyl, a $C_1$-$C_6$ heterocyclylthioalkyl, a $C_1$-$C_6$ arylthioalkyl, a $C_1$-$C_6$ alkanoylaminoalkyl $C_1$-$C_6$, a $C_1$-$C_6$ haloalkanoylaminoalkyl $C_1$-$C_6$, a $C_3$-$C_{12}$ cycloalkanoylaminoalkyl $C_1$-$C_6$, a $C_1$-$C_6$ aroylaminoalkyl, a $C_1$-$C_6$ heterocyclylaminoalkyl;

A represents a direct bond or a $C_1$-$C_6$ alkyl;

Y represents an oxygen or sulfur atom;

X represents a halogen atom, a CN group, a $NO_2$ group;

n represents a number ranging from 0 to 1;

G represents a $C_3$-$C_{12}$ cycloalkyl containing from 0 to 3 heteroatoms selected from O, N, S, a $C_3$-$C_{12}$ cycloalkenyl containing from 1 to 3 unsaturations and from 0 to 3 heteroatoms selected from O, N, S, a $C_6$-$C_{16}$ bicycloalkyl containing from 0 to 3 heteroatoms selected from O, N, S, a $C_6$-$C_{16}$ bicycloalkenyl containing from 1 to 3 unsaturations and from 0 to 3 heteroatoms selected from O, N, S, adamantyl, said cyclic groups being optionally substituted with 1 to 3 groups, the same or different, selected from $C_1$-$C_6$ alkyl, $C_3$-$C_{12}$ cycloalkyl, benzyl and with the possibility of incorporating in said cyclic structure one or more groups selected from: C=O, C(=O)O, C(=O)S, C(=S)O, C(=S)S, C(=O)$NR^3$.

More preferred are amides having formula (I) wherein:

$R^2$ represents a $C_2$-$C_6$ acyl, a $C_1$-$C_6$ alkoxy-$C_1$-$C_6$-alkanoyloxyalkyl $C_1$-$C_6$, a $C_1$-$C_6$ haloalkoxy-$C_1$-$C_6$-alkanoyloxyalkyl $C_1$-$C_6$, a $C_3$-$C_{12}$ cycloalkoxy-$C_1$-$C_6$-alkanoyloxyalkyl $C_1$-$C_6$, a $C_3$-$C_{12}$ cycloalkyloxyalkyl $C_1$-$C_6$, a $C_4$-$C_{12}$ alkanoylthioalkyl $C_1$-$C_6$, a $C_2$-$C_6$ haloalkanoylthioalkyl $C_1$-$C_6$, a $C_4$-$C_{12}$ cycloalkanoylthioalkyl $C_1$-$C_6$, a $C_2$-$C_6$ alkanoylaminoalkyl $C_1$-$C_6$, a $C_2$-$C_6$ haloalkanoylaminoalkyl $C_1$-$C_6$, a $C_1$-$C_6$ alkoxy-$C_1$-$C_6$-alkyloxyalkyl $C_1$-$C_6$, a $C_1$-$C_6$ haloalkoxy-$C_1$-$C_6$-alkyloxyalkyl $C_1$-$C_6$, a $C_3$-$C_{12}$ cycloalkoxy $C_1$-$C_6$-alkyloxyalkyl $C_1$-$C_6$, a tetrahydropyranyl, a $C_1$-$C_6$ trimethylsylyloxyalkyl, a $C_1$-$C_6$ trimethylsylyl-ethoxyalkyl;

Y and Z both represent an oxygen atom;

G represents a $C_3$-$C_{12}$ cycloalkyl containing from 0 to 3 heteroatoms selected from O, N, S, a $C_3$-$C_{12}$ cycloalkenyl containing from 1 to 3 unsaturations and from 0 to 3 heteroatoms selected from O, N, S, a $C_6$-$C_{16}$ bicycloalkyl containing from 0 to 3 heteroatoms selected from O, N, S, a $C_6$-$C_{16}$ bicycloalkenyl containing from 1 to 3 unsaturations and from 0 to 3 heteroatoms selected from O, N, S, adamantyl, said cyclic groups being optionally substituted with 1 to 3 groups, the same or different, selected from $C_1$-$C_6$ alkyl, $C_3$-$C_{12}$ cycloalkyl, benzyl and with the possibility of incorporating in said cyclic structure one or more groups selected from: C=O, C(=O)O, C(=O)S, C(=S)O, C(=S)S, C(=O)$NR^3$.

Even more preferred are amides having formula (I) wherein:

$R^2$ represents a hydrogen atom;

G represents a $C_3$-$C_{12}$ cycloalkyl containing from 0 to 3 heteroatoms selected from O, N, S, a $C_3$-$C_{12}$ cycloalkenyl containing from 1 to 3 unsaturations and from 0 to 3 heteroatoms selected from O, N, S, said cyclic groups being optionally substituted with 1 to 3 groups, the same or different, selected from $C_1$-$C_6$ alkyl, $C_3$-$C_{12}$ cycloalkyl, benzyl and incorporating in said cyclic structure one or more groups selected from: C=O, C(=O)O, C(=O)S, C(=S)O, C(=S)S, C(=O)$NR^3$.

Said cyclic systems can also be condensed with an aromatic system with 5 and 6 terms possibly containing from 1 to 2 heteroatoms selected from O, N. S.

Said cyclic systems can be substituted by one or more groups selected from halogen atoms, $C_1$-$C_{12}$ alkyl groups, $C_1$-$C_{12}$ haloalkyl groups, $C_3$-$C_{18}$ cycloalkyl groups, $C_2$-$C_{12}$ alkenyl groups, $C_3$-$C_{18}$ cycloalkenyl groups, $C_2$-$C_{12}$ haloalkenyl groups, $C_1$-$C_{12}$ alkoxyl groups, $C_3$-$C_{18}$ cycloalkoxyl groups, $C_1$-$C_{12}$ haloalkoxyl groups, a cyano group, a formyl, a $C_1$-$C_{12}$ alkylthioalkyl $C_1$-$C_{12}$ group, a $C_1$-$C_{12}$ haloalkylthioalkyl $C_1$-$C_{12}$ group, a $C_3$-$C_{18}$ cycloalkylthioalkyl $C_1$-$C_{12}$ group, an aryl group, a phenoxyl group, a thiophenoxyl group, a benzyl group, a $C_4$-$C_{18}$ cycloalkylalkyl group, a $C_1$-$C_{12}$ alkoxyalkyl $C_2$-$C_{12}$ group, a $C_1$-$C_{12}$ alkylthioalkyl $C_1$-$C_{12}$ group, a $C_2$-$C_{12}$ alkoxycarbonyl group, a $C_4$-$C_{12}$cycloalkoxycarbonyl group, a phenoxycarbonyl group, a benzyloxycarbonyl group, a $C_2$-$C_{12}$ alkylaminocarbonyl group, a $C_3$-$C_{12}$ dialkylaminocarbonyl group, a $C_1$-$C_{12}$ alkylamine group, a $C_3$-$C_{18}$ cycloalkylamine group, an arylamine group, a $C_2$-$C_{12}$ dialkylamine group, a N—$C_1$-$C_2$alkyl-N—$C_3$-$C_{18}$ cycloalkylamine group, a diarylamine group;

or an $R^6$ group wherein $R^6$ represents a spiro-anular carbocyclic group with from 3 to 10 terms saturated or partially unsaturated.

$C_2$-$C_{12}$ alkanoyloxyalkyl $C_1$-$C_{12}$, $C_2$-$C_{12}$ haloalkanoyloxyalkyl $C_1$-$C_{12}$, $C_4$-$C_{18}$ cycloalkanoyloxyalkyl $C_1$-$C_{12}$, $C_1$-$C_{12}$ aroyloxyalkyl, $C_1$-$C_{12}$ benzoyloxyalkyl, $C_1$-$C_{12}$ heterocyclylcarbonyloxyalkyl, refer to a radical having formula RaC(=O)ORb wherein Ra respectively has the meaning of $C_1$-$C_{12}$ alkyl, $C_1$-$C_{12}$ haloalkyl, $C_3$-$C_{18}$ cycloalkyl, aryl, benzyl and heterocyclyl and Rb has the meaning of $C_1$-$C_{12}$ alkyl.

Examples of these groups are propanoyloxymethyl, cyclohexanoyloxymethyl, benzoyloxyethyl.

$C_1$-$C_{12}$ alkoxy $C_1$-$C_{12}$ alkanoyloxyalkyl $C_1$-$C_{12}$, $C_1$-$C_{12}$ haloalkoxy $C_1$-$C_{12}$-alkanoyloxyalkyl $C_1$-$C_{12}$, $C_3$-$C_{18}$ cycloalkoxy $C_1$-$C_{12}$ alkanoyloxyalkyl $C_1$-$C_{12}$, phenoxy $C_1$-$C_{12}$ alkanoyloxyalkyl $C_1$-$C_{12}$, benzyloxy $C_1$-$C_{12}$ alkanoyloxyalkyl $C_1$-$C_{12}$, refer to a radical having formula RcORbC(=O)ORa wherein Rc respectively has the meanings of $C_1$-$C_{12}$ alkyl, $C_1$-$C_{12}$ haloalkyl, $C_3$-$C_{18}$ cycloalkyl, aryl and benzyl and heterocyclyl and Ra and Rb have the meaning of $C_1$-$C_{12}$ alkyl.

Examples of these groups are 3-methoxy-1-propanoyloxymethyl, 2-cyclopropoxy-butanoyloxynethyl.

$C_2$-$C_{12}$ alkanoylthioalkyl $C_1$-$C_{12}$, $C_2$-$C_{12}$ haloalkanoylthioalkyl $C_1$-$C_{12}$, $C_4$-$C_{18}$ cycloalkanoylthioalkyl $C_1$-$C_{12}$, $C_1$-$C_{12}$ aroylthioalkyl, $C_1$-$C_{12}$ benzoylthioalkyl, $C_1$-$C_{12}$ heterocyclylcarbonylthioalkyl, refer to a radical having formula RaC(=O)SRb wherein Ra respectively has the meaning of $C_1$-$C_{12}$ alkyl, $C_1$-$C_{12}$ haloalkyl, $C_3$-$C_{18}$ cycloalkyl, aryl and benzyl and heterocyclyl and Rb has the meaning of $C_1$-$C_{12}$ alkyl.

Examples of these groups are propanoylthiomethyl, cyclohexanoylthiomnethyl, benzoylthioethyl.

$C_1$-$C_{12}$ alkyloxyalkyl $C_1$-$C_{12}$, $C_1$-$C_{12}$ haloalkyloxyalkyl $C_1$-$C_{12}$, a $C_3$-$C_{18}$ cycloalkyloxyalkyl $C_1$-$C_{12}$, a $C_1$-$C_{12}$ aryloxyalkyl, a benzyloxyalkyl $C_1$-$C_{12}$; a heterocyclyloxyalkyl $C_1$-$C_{12}$, refer to a radical having formula RaORb wherein Ra has the meaning of $C_1$-$C_{12}$ alkyl, $C_1$-$C_{12}$ haloalkyl, $C_3$-$C_{18}$ cycloalkyl, aryl and benzyl and heterocyclyl and Rb has the meaning of $C_1$-$C_{12}$ alkyl.

Examples of these groups are ethoxymethyl, trifluoromethoxymethyl, phenoxyethyl.

$C_1$-$C_{12}$ alkylthioalkyl $C_1$-$C_{12}$, $C_1$-$C_{12}$ haloalkylthioalkyl $C_1$-$C_{12}$, $C_3$-$C_{18}$ cycloalkylthioalkyl $C_1$-$C_{12}$, a $C_1$-$C_{12}$ benzylthioalkyl, a $C_1$-$C_{12}$ arylthioalkyl, a $C_1$-$C_{12}$ heterocyclylthioalkyl, refer to a radical having formula RaSRb wherein Ra has the meaning of $C_1$-$C_{12}$ alkyl, $C_1$-$C_{12}$ haloalkyl, $C_3$-$C_{18}$ cycloalkyl, aryl and benzyl and heterocyclyl and Rb has the meaning of $C_1$-$C_{12}$ alkyl.

Examples of these groups are ethylthioethyl, cyclopropylthiomethyl, phenylthioethyl. $C_1$-$C_{12}$ alkoxy $C_1$-$C_{12}$ alkyloxyalkyl $C_1$-$C_{12}$, $C_1$-$C_{12}$ haloalkoxy $C_1$-$C_{12}$-alkyloxyalkyl $C_1$-$C_{12}$, $C_3$-$C_{18}$ cycloalkoxy $C_1$-$C_{12}$ alkyloxyalkyl $C_1$-$C_{12}$, $C_1$-$C_{12}$ aryloxy $C_1$-$C_{12}$ alkyloxyalkyl, $C_1$-$C_{12}$ benzyloxy $C_1$-$C_{12}$ alkyloxyalkyl, refer to a radical having formula RcORbORa wherein Rc has the meaning of $C_1$-$C_{12}$ alkyl, $C_1$-$C_{12}$ haloalkyl, $C_3$-$C_{18}$ cycloalkyl, aryl, and benzyl and Ra and Rb have the meaning of $C_1$-$C_{12}$ alkyl. Examples of these groups are 1-methoxy-propyl-2-oxy-methyl, cyclopentoxy-2-ethoxy-methyl.

$C_1$-$C_{12}$ alkoxy $C_1$-$C_{12}$ alkylthioalkyl $C_1$-$C_{12}$, $C_1$-$C_{12}$ haloalkoxy-$C_1$-$C_{12}$-alkylthioalkyl $C_1$-$C_{12}$, $C_3$-$C_{18}$ cycloalkoxy $C_1$-$C_{12}$-alkylthioalkyl $C_1$-$C_{12}$, aryloxy $C_1$-$C_{12}$-alkylthioalkyl $C_1$-$C_{12}$, benzyloxy $C_1$-$C_{12}$ alkylthioalkyl $C_1$-$C_{12}$, refer to a radical having formula RcORbSRa wherein Rc has the meaning of $C_1$-$C_{12}$ alkyl, $C_1$-$C_{12}$ haloalkyl, $C_3$-$C_{18}$ cycloalkyl, aryl, and benzyl and Ra and Rb have the meaning of $C_1$-$C_{12}$ alkyl. Examples of these groups are 1-methoxy-propyl-2-thio-methyl, cyclopentoxy-2-ethylthio-methyl.

$C_2$-$C_{12}$ alkanoylaminoalkyl $C_1$-$C_{12}$, $C_2$-$C_{12}$ haloalkanoylaminoalkyl $C_1$-$C_{12}$, $C_4$-$C_{18}$ cycloalkanoylaminoalkyl $C_1$-$C_{12}$, $C_1$-$C_{12}$ aroylamino-alkyl, $C_1$-$C_{12}$ heterocyclylcarbonylaminoalkyl, refer to a radical having formula RaC(=O)NHRb wherein Ra has the meaning of $C_1$-$C_{12}$ alkyl, $C_1$-$C_{12}$ haloalkyl, $C_3$-$C_{18}$ cycloalkyl, aryl and heterocyclyl and Rb has the meaning of $C_1$-$C_{12}$ alkyl.

Examples of these groups are propanoylaminomethyl, cyclohexanoylaminonethyl, benzoylaninoethyl.

$C_2$-$C_{12}$ alkoxyalkyl, $C_4$-$C_{12}$ cycloalkyl-oxyalkyl, $C_1$-$C_{12}$ aryloxyalkyl and $C_1$-$C_{12}$ heterocyclyloxyalkyl, refer to a radical RaORb wherein Ra respectively has the meaning of $C_1$-$C_{12}$ alkyl, $C_3$-$C_{18}$ cycloalkyl, aryl and heterocyclyl and Rb has the meaning of $C_1$-$C_{12}$ alkyl.

Examples of these groups are cyclopentyloxymethyl, 2-thiadiazoles-oxymethyl.

$C_2$-$C_{12}$ alkylthioalkyl, $C_1$-$C_{12}$ cycloalkylthioalkyl, $C_1$-$C_{12}$ arylthioalkyl, $C_1$-$C_{12}$ heterocyclylthioalkyl, refer to a radical RaSRb wherein Ra respectively has the meaning of $C_1$-$C_{12}$ alkyl, $C_3$-$C_{18}$ cycloalkyl, aryl and heterocyclyl and Rb has the meaning of $C_1$-$C_{12}$ alkyl.

Examples of these groups are cyclopentylthiomethyl, 2-thiadiazolyl-thiomethyl.

$C_1$-$C_{12}$ cycloalkylaminoalkyl, and $C_1$-$C_{12}$ heterocyclylaminoalkyl, refer to a radical RaNHRb respectively has the meaning of $C_3$-$C_{18}$ cycloalkyl, and heterocyclyl and Rb has the meaning of $C_1$-$C_{12}$ alkyl.

Examples of these groups are N-cyclopentyl-N-methylamino, N-2-thiadiazol-N-methylamino.

Examples of halogen are fluorine, chlorine, bromine, iodine.

Examples of $C_1$-$C_{12}$ alkyl are methyl, ethyl, n-propyl, isopropyl, n-butyl, isobutyl, sec-butyl, tert-butyl, n-pentyl, 3-methylbutyl, n-hexyl, 3,3-dimethylbutyl.

Examples of $C_1$-$C_{12}$ haloalkyl are fluoromethyl, difluoromethyl, trifluoromethyl, chloromethyl, dichloromethyl, 2,2,2-trifluoroethyl, 1,1,2-tetrafluoroethyl, pentafluoroethyl, heptafluoropropyl, 4,4,4-trichloro-butyl, 4,4-difluoropentyl, 5,5-difluorohexyl.

Examples of $C_3$-$C_{18}$ cycloalkyl are cyclopropyl, cyclobutyl, cyclopentyl, cyclohexyl, (2E,6E,10E)-2,6,9,9-tetramethyl-2,6,10-cycloundecatrienyl.

Examples of $C_6$-$C_{20}$ bicycloalkyl are bicyclo[2.2.1]heptane, bicyclo[4.3.0] nonane, bicyclo[3.2.1] octane.

Examples of $C_2$-$C_{12}$ alkenyl are: ethenyl, propenyl, butenyl.

Examples of $C_2$-$C_{12}$ haloalkenyl are: 2,2-dichloro-propenyl, 1,2,2-trichloropropenyl.

Examples of $C_3$-$C_{18}$ cycloalkenyl are cyclobutenyl, cyclopentenyl, cyclohexenyl.

Examples of bicycloalkenyl are 2,3,4A,5,8,8a-hexahydronaphthyl, norbornyl.

Examples of $C_4$-$C_{18}$ cycloalkylalkyl are: 2-ethylcyclopropyl, cyclopentylmethyl, 3-propylhexyl.

Examples of $C_2$-$C_{13}$ acyl groups are acetyl, propanoyl, isopropanoyl.

Examples of $C_2$-$C_{12}$ haloalkylcarbonyl are: fluoromethylcarbonyl, difluoromethylcarbonyl, trifluoromethylcarbonyl, dichloromethylecarbonyl, 2,2,2-trifluoroethylcarbonyl.

Examples of $C_2$-$C_{12}$ alkoxycarbonyl are methoxycarbonyl, propoxycarbonyl, hexyloxycarbonyl.

Examples of $C_4$-$C_{12}$ cycloalkoxycarbonyl are cyclopropoxicarbonyl, cyclohexyloxycarbonyl.

Examples of $C_2$-$C_{12}$ alkylaminocarbonyl are N-methyl-aminocarbonyl, N-propylaminocarbonyl, N-decylaminocarbonyl.

Examples of $C_3$-$C_{12}$ dialkylaminocarbonyl are N, N-dimethylaminocarbonyl, N-propyl-N-methylaminocarbonyl, N-decyl-N-propylaminocarbonyl.

Examples of $C_1$-$C_{12}$ alkylamino are methylamino, isopropylamino, dodecylamino.

Examples of $C_3$-$C_{18}$ cycloalkylamino are cyclopentylamino, cyclohexylamino, cyclooctylamino.

Examples of $C_2$-$C_{18}$ dialkylamino are N,N-dimethylamino, N-ethyl-N-butylamino, N-hexyl-N-nonylamino.

Examples of N—$C_1$-$C_{12}$ alkyl-N—$C_3$-$C_{18}$ cyclo-alkylamino $C_3$-$C_{18}$ are N-methyl-N-cyclopropylamino; N-propyl-N-cyclohexylamino, N-octyl-N-cyclopropylamino.

Examples of $C_1$-$C_{12}$ alkoxyl are methoxyl, ethoxyl.

Examples of $C_1$-$C_{12}$ haloalkoxyl are trifluoromethoxyl, 1,1,2,2-tetrafluoroethoxyl, 1,1,2,3,3,3-hexafluoro-propyloxyl.

Examples of $C_3$-$C_{18}$ cycloalkoxyl are cyclopropoxyl, cyclopentloxyl.

Examples of $C_1$-$C_{12}$ thioalkyl are thiomethyl, thioethyl.

Examples of $C_1$-$C_{12}$ thiohaloalkyl are trifluorothiomethyl, 1,1,2,2-tetrafluorothioethyl.

Examples of $C_3$-$C_{18}$ thiocycloalkyl are thiocyclopropyl, thiocyclopentyl.

Examples of heterocyclic rings, which refer to 5 or 6-term cyclical systems, aromatic or non-aromatic, possibly benzocondensed, containing from 1 to 3 heteroatoms selected from O, N, S, are: thiazole, 1,3,4 thiadiazole, pyrrolidine, piperidine, morpholine, pyrazole etc.

Examples of aryl, which refer to mono, bi or tricyclic aromatic systems, consisting of only carbon atoms, are phenyl, naphthyl, phenanthrenyl, anthracenyl.

All of the aryl, benzyl, phenoxy, thiophenoxyl and heterocyclic systems can be substituted by one or more groups selected from halogens, $C_1$-$C_{12}$ alkyl, $C_1$-$C_{12}$ haloalkyl, $C_3$-$C_{18}$ cycloalkyl, $C_1$-$C_{12}$ alkoxyl, $C_4$-$C_{18}$ cycloalkoxyl, $C_1$-$C_{18}$ haloalkoxyl.

The following also fall within the spirit of the present invention:

a) all the possible geometric isomers of the compounds having general formula (I) deriving from particular meanings of the substituents $R^1$-$R^6$, Z, A and G;

b) the salts of the compounds having formula (I) obtained by the addition of inorganic or organic acids;

c) possible hydrated forms of the compounds having formula (I).

Examples of preferred compounds having general formula (I) are compounds wherein $R^1$, $R^2$, $R^3$, Y, Z, X, n, A, G have the meanings indicated in Table 1:

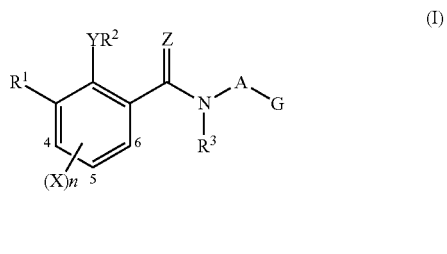

TABLE 1

| Com. | $R^1$ | $R^2$ | $R^3$ | Y | Z | A | X | n | G |
|---|---|---|---|---|---|---|---|---|---|
| 1. | NHCHO | *—CH₂—O—C(CH₃)H—C(=O)— | H | O | O | — | | 0 | 3,3,5-trimethylcyclohexyl |
| 2. | NHCHO | *—CH₂—O—C(CH₃)₂—C(=O)— | H | O | O | — | | 0 | 3,3,5-trimethylcyclohexyl |
| 3. | NHCHO | *—CH₂—O—C(cyclopropyl)H—C(=O)— | H | O | O | — | | 0 | 3,3,5-trimethylcyclohexyl |
| 4. | $NR^2$CHO | *—CH₂—O—C(CH₃)H—C(=O)— | H | O | O | — | | 0 | 3,3,5-trimethylcyclohexyl |
| 5. | $NR^2$CHO | *—CH₂—O—C(CH₃)₂—C(=O)— | H | O | O | — | | 0 | 3,3,5-trimethylcyclohexyl |

TABLE 1-continued

| Com. | R¹ | R² | R³ | Y | Z | A | X | n | G |
|---|---|---|---|---|---|---|---|---|---|
| 6. | NR²CHO | *-CH₂-O-C(=O)-cyclopropyl | H | O | O | — | | 0 | *-3,3,5,5-tetramethylcyclohexyl |
| 7. | NR₂² | *-CH₂-O-C(=O)-CH(CH₃)₂ | H | O | O | — | | 0 | *-3,3,5,5-tetramethylcyclohexyl |
| 8. | NR₂² | *-CH₂-O-C(=O)-C(CH₃)₃ | H | O | O | — | | 0 | *-3,3,5,5-tetramethylcyclohexyl |
| 9. | NR₂² | *-CH₂-O-C(=O)-cyclopropyl | H | O | O | — | | 0 | *-3,3,5,5-tetramethylcyclohexyl |
| 10. | NHCHO | *-CH₂-O-C(=O)-CH(CH₃)₂ | H | O | O | — | | 0 | *-3,3,5-trimethyl-5-ethylcyclohexyl |
| 11. | NHCHO | *-CH₂-O-C(=O)-CH(CH₃)₂ | H | O | O | — | | 0 | *-cyclododecyl |
| 12. | NHCHO | *-CH₂-O-C(=O)-CH(CH₃)₂-O | H | O | O | — | | 0 | *-cyclooctyl |
| 13. | NHCHO | *-CH₂-O-C(=O)-CH(CH₃)₂ | H | O | O | — | | 0 | *-adamantyl |
| 14. | NHCHO | *-CH₂-O-C(=O)-CH(CH₃)₂ | H | O | O | — | | 0 | *-macrocyclic ketone group |

TABLE 1-continued
| Com. | R¹ | R² | R³ | Y | Z | A | X | n | G |
|---|---|---|---|---|---|---|---|---|---|
| 15. | NHCHO | 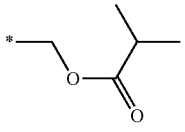 | H | O | O | — | | 0 | 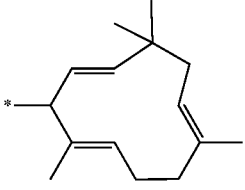 [SMILES: *C1/C=C/C(C)(C)C/C=C(\C)CC/C=C/1C] |
| 16. | NHCHO | 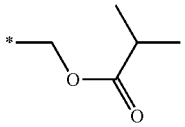 | H | O | O | — | | 0 | 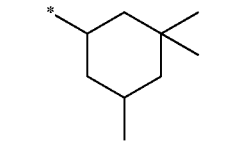 [SMILES: *C1CC(C)CC(C)(C)C1] |
| 17. | NHCHO | 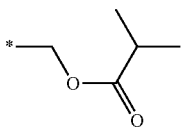 | H | O | O | — | | 0 | 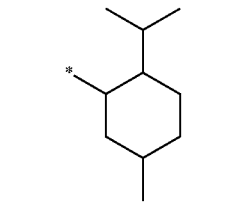 |
| 18. | NHCHO | 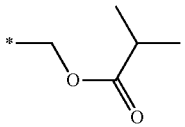 [SMILES: *COC(=O)C(C)C] | H | O | O | — | | 0 | 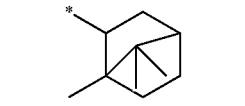 |
| 19. | NHCHO | 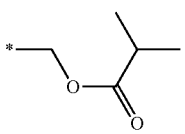 | H | O | O | — | | 0 | 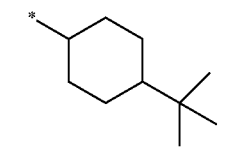 [SMILES: *C1CCC(C(C)(C)C)CC1] |
| 20. | NHCHO | 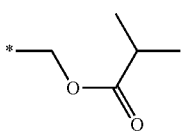 [SMILES: *COC(=O)C(C)C] | CH₃ | O | O | — | | 0 | 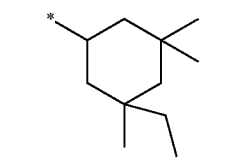 |
| 21. | NHCHO | 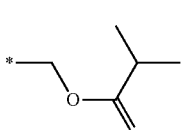 | CH₃ | O | O | — | | 0 | 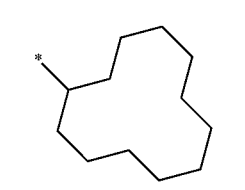 [SMILES: *C1CCCCCCCCCCC1] |
| 22. | NHCHO | 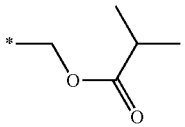 [SMILES: *COC(=O)C(C)C] | CH₃ | O | O | — | | 0 | 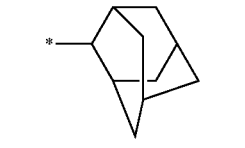 [SMILES: *C1C2CC3CC(C2)CC1C3] |
| 23. | NHCHO | 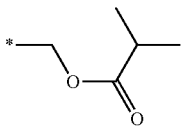 | H | S | O | — | | 0 | 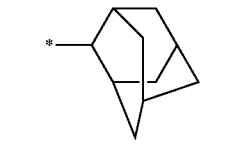 [SMILES: *C1C2CC3CC(C2)CC1C3] |

TABLE 1-continued
| Com. | R¹ | R² | R³ | Y | Z | A | X | n | G |
|---|---|---|---|---|---|---|---|---|---|
| 24. | OCH₃ | 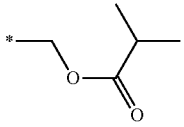 | H | S | O | — |  | 0 | 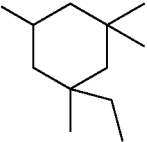 |
| 25. | NHCHO | 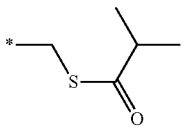 | H | S | O | — |  | 0 | 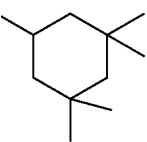 |
| 26. | NHCHO | 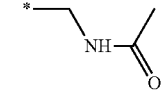 | H | O | O | — |  | 0 | 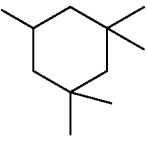 |
| 27. | NHCHO | 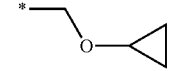 | H | O | O | — |  | 0 | 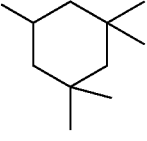 |
| 28. | NHCHO | 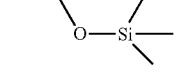 | H | O | O | — |  | 0 | 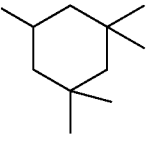 |
| 29. | NHCHO |  | H | O | O | — |  | 0 | 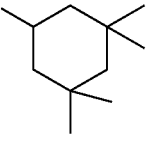 |
| 30. | NHCHO | 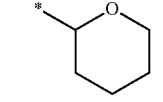 [SMILES: *C1CCCCO1] | H | O | O | — |  | 0 | 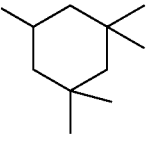 |
| 31. | NHCHO | 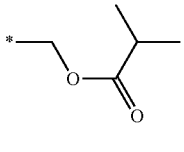 | H | O | O | CH₂ |  | 0 | 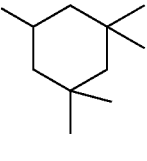 |
| 32. | NHCHO | 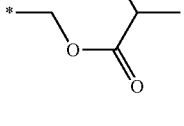 | H | O | O | CH₂ |  | 0 | 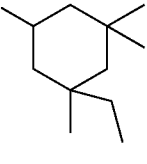 |
| 33. | OCH₃ | 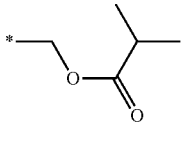 | H | O | O | — | 5-Cl | 1 | 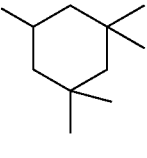 |

TABLE 1-continued
| Com. | R¹ | R² | R³ | Y | Z | A | X | n | G |
|---|---|---|---|---|---|---|---|---|---|
| 34. | OCH₃ | 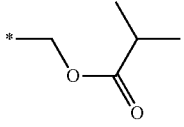 | H | O | O | — | 6-Br | 1 | 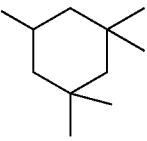 |
| 35. | OCH₃ | 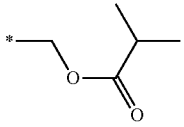 | H | O | O | — | 4-NO₂ | 1 | 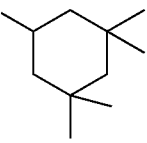 |
| 36 | NHCHO | 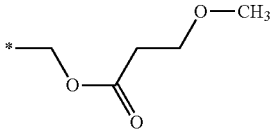 [SMILES: *COC(=O)CCOC] | H | O | O | CH₂ | | 0 | 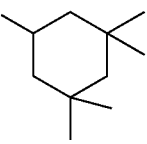 |
| 37 | NHCHO | 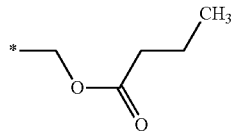 [SMILES: *COC(=O)CCC] | H | O | O | CH₂ | | 0 | 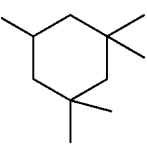 |
| 38 | NHCHO | 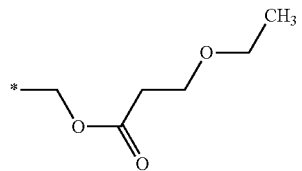 [SMILES: *COC(=O)CCOCC] | H | O | O | CH₂ | | 0 | 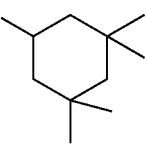 |
| 39 | NHCHO | 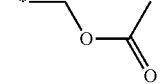 | H | O | O | — | | 0 | 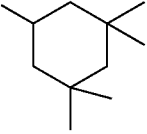 |
| 40 | NHCHO | 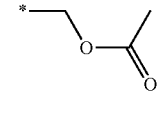 | H | O | O | — | | 0 | 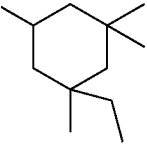 |
| 41 | NHCHO | 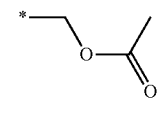 | H | S | O | | | 0 | 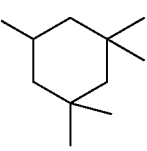 |
| 42 | NHCHO | 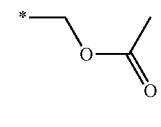 | H | S | O | — | | 0 | 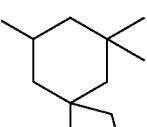 |
| 43 | NHCHO | 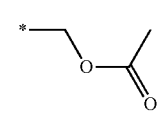 | H | O | O | — | | 0 | 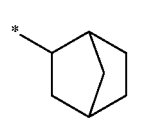 |

TABLE 1-continued
| Com. | R¹ | R² | R³ | Y | Z | A | X | n | G |
|---|---|---|---|---|---|---|---|---|---|
| 44 | NHCHO | 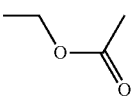 | H | S | O | — |  | 0 |  |
| 45 | NHCHO | 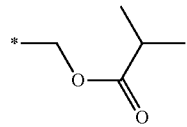 | H | O | O | — |  | 0 |  |
| 46 | NHCHO | 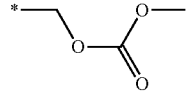 [SMILES: *COC(=O)OC] | H | O | O | — |  | 0 |  |
| 47 | NHCHO | 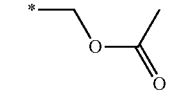 | H | O | O | — |  | 0 | 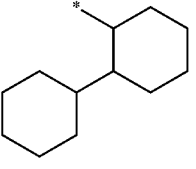 |
| 48 | NHCHO | 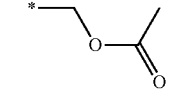 | H | S | O | — |  | 0 | 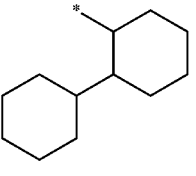 [SMILES: *C1CCCCC1C1CCCCC1] |
| 49 | NHCHO | 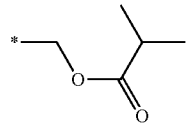 [SMILES: *COC(=O)C(C)C] | H | O | O | — |  | 0 | 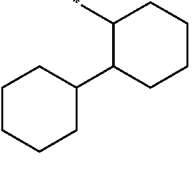 |
| 50 | NHCHO | 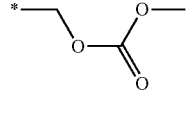 [SMILES: *COC(=O)OC] | H | O | O | — |  | 0 | 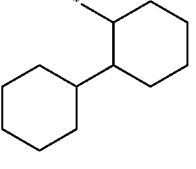 |
| 51 | NHCHO | H | H | O | O | — |  | 0 | 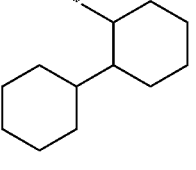 |
| 52 | NHCHO | COCH₃ | H | O | O | — |  | 0 | 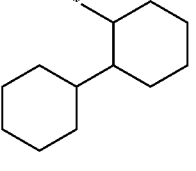 |
| 53 | NHCHO | 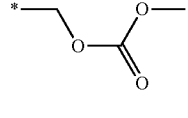 | H | O | O | — |  | 0 | 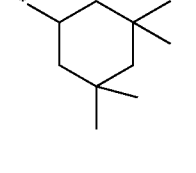 |

TABLE 1-continued
| Com. | R¹ | R² | R³ | Y | Z | A | X | n | G |
|---|---|---|---|---|---|---|---|---|---|
| 54 | NHCHO | 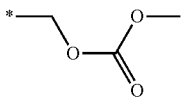 [SMILES: *COC(=O)OC] | H | O | O | — | | 0 | 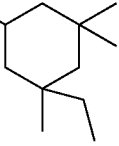 |
| 55 | NHCHO | 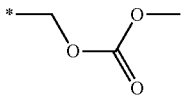 [SMILES: *COC(=O)OC] | H | O | O | — | | 0 | 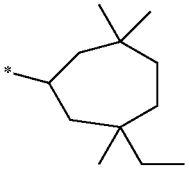 [SMILES: *C1CC(C)(C)CCC(C)(CC)C1] |
| 56 | NHCHO | 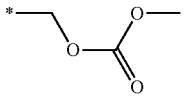 [SMILES: *COC(=O)OC] | H | O | O | — | | 0 | 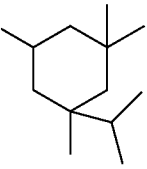 |
| 57 | NHCHO | 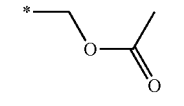 | H | O | O | — | | 0 | 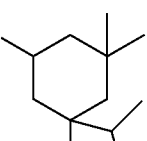 |
| 58 | NHCHO | 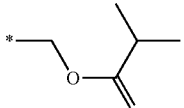 | H | O | O | — | | 0 | 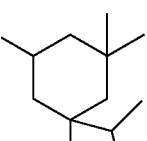 |
| 59 | NHCHO | 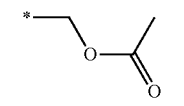 | H | O | O | — | | 0 | 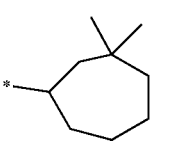 |
| 60 | NHCHO | 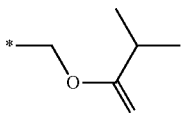 | H | O | O | — | | 0 | 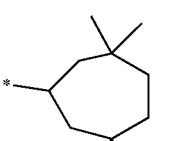 |
| 61 | NHCHO | 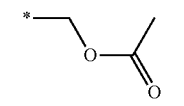 | H | O | O | — | | 0 | 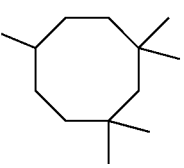 |
| 62 | NHCHO | 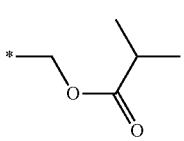 [SMILES: *COC(=O)C(C)C] | H | O | O | — | | 0 | 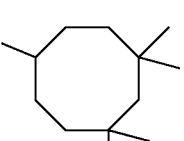 |

TABLE 1-continued

| Com. | R¹ | R² | R³ | Y | Z | A | X | n | G |
|---|---|---|---|---|---|---|---|---|---|
| 63 | NHCHO | *-CH₂-O-C(=O)-O-CH₃ | H | O | O | — | | 0 | cyclooctane with gem-dimethyl groups |
| 64 | NHCHO | *-CH₂-S-C(=O)-CH(CH₃)₂ | H | S | O | — | | 0 | cyclohexane with trimethyl and ethyl substituents |
| 65 | NHCHO | *-CH₂-NH-C(=O)-CH₃ | H | O | O | — | | 0 | cyclohexane with trimethyl and ethyl substituents |
| 66 | NHCHO | *-CH₂-O-cyclopropyl | H | O | O | — | | 0 | cyclohexane with trimethyl and ethyl substituents |
| 67 | NHCHO | *-CH₂-O-Si(CH₃)₃ | H | O | O | — | | 0 | cyclohexane with trimethyl and ethyl substituents |
| 68 | NHCHO | *-CH₂-O-CH₂CH₂-Si(CH₃)₃ | H | O | O | — | | 0 | cyclohexane with trimethyl and ethyl substituents |
| 69 | NHCHO | *-tetrahydropyran-2-yl | H | O | O | — | | 0 | cyclohexane with trimethyl and ethyl substituents |
| 70 | NHCHO | *-CH₂-O-C(=O)-CH₃ | H | O | O | CH₂ | | 0 | cyclohexane with trimethyl and ethyl substituents |
| 71 | NHCHO | H | H | O | O | — | | 0 | cyclic diester (lactone) |

TABLE 1-continued

| Com. | R¹ | R² | R³ | Y | Z | A | X | n | G |
|---|---|---|---|---|---|---|---|---|---|
| 72 | NHCHO | COCH₃ | H | O | O | — |  | 0 | (lactone ring) |
| 73 | NHCHO | *-CH₂-O-C(=O)-CH₃ | H | O | O | — |  | 0 | (lactone ring) |
| 74 | NHCHO | *-CH₂-O-C(=O)-O-CH₃ | H | O | O | — |  | 0 | (lactone ring) |
| 75 | NHCHO | *-CH₂-O-C(=O)-CH(CH₃)₂ | H | O | O | — |  | 0 | (lactone ring) |
| 76 | NHCHO | H | H | O | O | — |  | 0 | (thiolactone ring) |
| 77 | NHCHO | COCH₃ | H | O | O | — |  | 0 | (thiolactone ring) |
| 78 | NHCHO | *-CH₂-O-C(=O)-CH₃ | H | O | O | — |  | 0 | (thiolactone ring) |

TABLE 1-continued
| Com. | R¹ | R² | R³ | Y | Z | A | X | n | G |
|---|---|---|---|---|---|---|---|---|---|
| 79 | NHCHO | 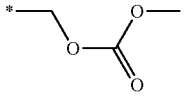 [SMILES: *COC(=O)OC] | H | O | O | — |  | 0 | 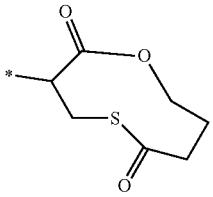 [SMILES: *C1CSC(=O)CCCOC1=O] |
| 80 | NHCHO | 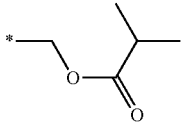 | H | O | O | — |  | 0 | 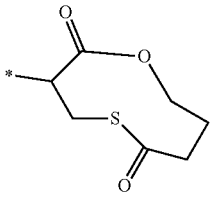 [SMILES: *C1CSC(=O)CCCOC1=O] |
| 81 | NHCHO | H | H | O | O | — |  | 0 | 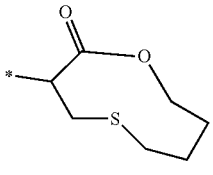 |
| 82 | NHCHO | COCH₃ | H | O | O | — |  | 0 | 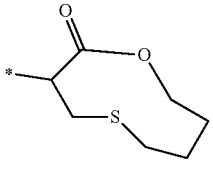 [SMILES: *C1CSCCCCOC1=O] |
| 83 | NHCHO | 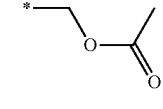 | H | O | O | — |  | 0 | 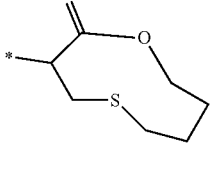 |
| 84 | NHCHO | 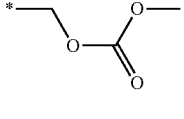 | H | O | O | — |  | 0 | 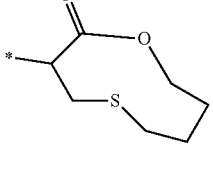 |
| 85 | NHCHO | 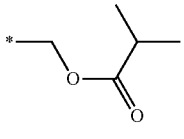 [SMILES: *COC(=O)C(C)C] | H | O | O | — |  | 0 | 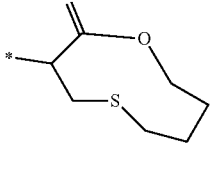 |
| 86 | NHCHO | H | H | O | O | — |  | 0 | 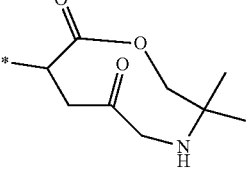 |

TABLE 1-continued
| Com. | R¹ | R² | R³ | Y | Z | A | X | n | G |
|---|---|---|---|---|---|---|---|---|---|
| 87 | NHCHO | 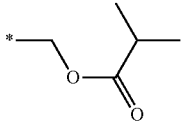 | H | O | O | — | | 0 | 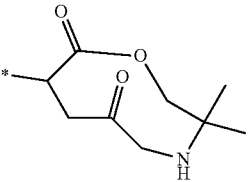 [SMILES: *C1CC(=O)CNC(C)(C)COC1=O] |
| 88 | NHCHO | COCH$_3$ | H | O | O | — | | 0 | 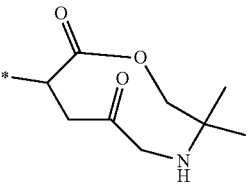 [SMILES: *C1CC(=O)CNC(C)(C)COC1=O] |
| 89 | NHCHO | 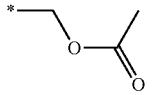 | H | O | O | — | | 0 | 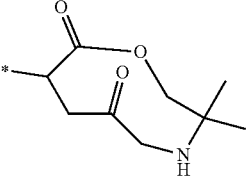 [SMILES: *C1CC(=O)CNC(C)(C)COC1=O] |
| 90 | NHCHO | 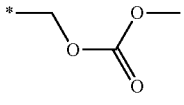 | H | O | O | — | | 0 | 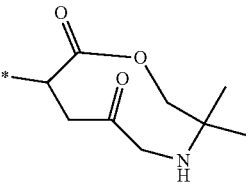 [SMILES: *C1CC(=O)CNC(C)(C)COC1=O] |
| 91 | NHCHO | 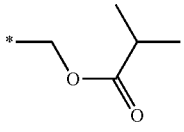 [SMILES: *COC(=O)C(C)C] | H | O | S | — | | 0 | 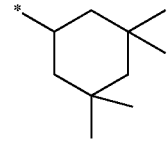 [SMILES: *C1CC(C)(C)CC(C)(C)C1] |
| 92 | NHCHO | 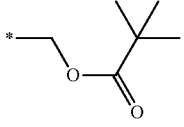 [SMILES: *COC(=O)C(C)(C)C] | H | O | S | — | | 0 | 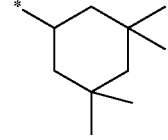 [SMILES: *C1CC(C)(C)CC(C)(C)C1] |
| 93 | NHCHO | 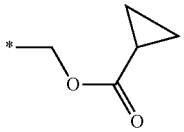 [SMILES: *COC(=O)C1CC1] | H | O | S | — | | 0 | 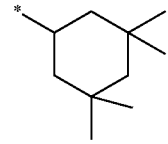 [SMILES: *C1CC(C)(C)CC(C)(C)C1] |
| 94 | NHCHO | 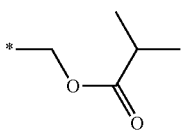 [SMILES: *COC(=O)C(C)C] | H | O | S | — | | 0 | 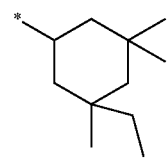 |
| 95 | NHCHO | 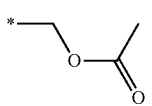 | H | O | S | — | | 0 | 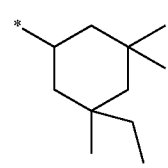 |

TABLE 1-continued
| Com. | R[1] | R[2] | R[3] | Y | Z | A | X | n | G |
|---|---|---|---|---|---|---|---|---|---|
| 96 | NHCHO | 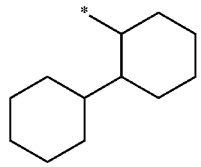 [SMILES: *C1CCCCC1C1CCCCC1] | H | O | S | — | | 0 | 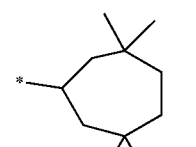 |
| 97 | NHCHO | 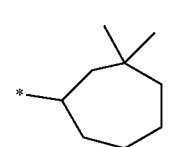 | H | O | S | — | | 0 | 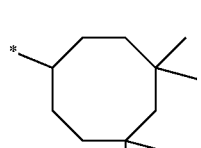 |
| 98 | NHCHO | 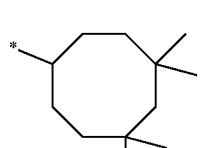 | H | O | S | — | | 0 | 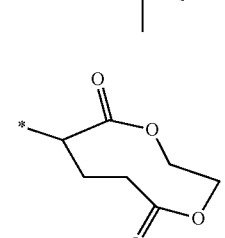 |
| 99 | NHCHO | 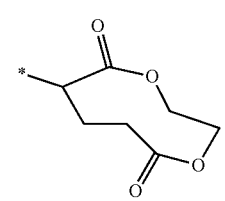 [SMILES: *C1CCC(=O)OCCOC1=O] | H | O | S | — | | 0 | 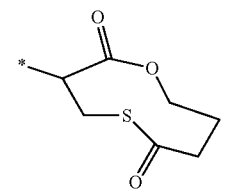 [SMILES: *C1CSC(=O)CCCOC1=O] |
| 100 | NHCHO |  | H | O | S | — | | 0 |  |
| 101 | NHCHO | COCH$_3$ | H | O | S | — | | 0 |  |
| 102 | NHCHO |  | H | O | S | — | | 0 |  |
| 103 | NHCHO | COCH$_3$ | H | O | S | — | | 0 |  |

TABLE 1-continued

| Com. | R¹ | R² | R³ | Y | Z | A | X | n | G |
|---|---|---|---|---|---|---|---|---|---|
| 104 | NHCHO | (isobutyl ester group) | H | O | S | — | | 0 | (cyclic structure with O, S, two C=O) |
| 105 | NHCHO | (isobutyl ester group) | H | O | S | — | | 0 | (ester-amide structure with gem-dimethyl) |
| 106 | NHCHO | COCH₃ | H | O | S | — | | 0 | (3,3,5-trimethylcyclohexyl with ethyl) |
| 107 | NHCHO | COCH₃ | H | O | S | — | | 0 | (3,3,5,5-tetramethylcyclohexyl) |

Amides having general formula (I) wherein R¹ represents an NR²CHO group, R² being equal to a hydrogen atom or having the meanings previously indicated for R² in Table 1, are particularly preferred, R¹ preferably represents an NHCHO group.

The compounds having general formula (I) can be obtained using various synthesis methods; for example, for exemplifying but non-exhaustive purposes, the compounds having general formula (I) wherein Z has the meaning of O, can be prepared from the compounds having general formula (II) by reaction with a suitable amine having formula (III) according to the reaction scheme 1.

The reaction is carried out by activating the acid by means of the corresponding chloride, for example with thionyl chloride in dichloromethane or chloroform or using a condenser such as N, N'-dicyclhexylcarbodiimide or N-(3-dimethylaminopropyl) N'-ethylcarbodiimide in tetrahydrofuran or ethyl acetate, or using 1,1-carbonyldiimidazole in tetrahydrofuran or methylene chloride at a temperature ranging from 0° C. to the reflux temperature of the solvent used, as widely described in R. Larock "Comprehensive Organic Transformations".

The activated acid form is then reacted with the amine having formula (III) in a suitable solvent such as methylene chloride, or dichloroethane, or chloroform at a temperature ranging from 0° C. to the reflux temperature of the solvent in the presence or absence of a base such as, for example, triethylamine or 4-dimethylaminopyridine according to what is known in literature in R. Larock "Comprehensive Organic Transformations".

The compounds having formula (III), when they are not commercial and A has the meaning of a direct bond and R³ is hydrogen, can be prepared, for example, from the corresponding cyclic ketones having formula (IV) by reaction in a solvent such as ethanol or methanol, at room temperature, with hydroxylamines having formula $NH_2OR'$ wherein R represents a hydrogen atom or a methyl according to the reaction scheme 2.

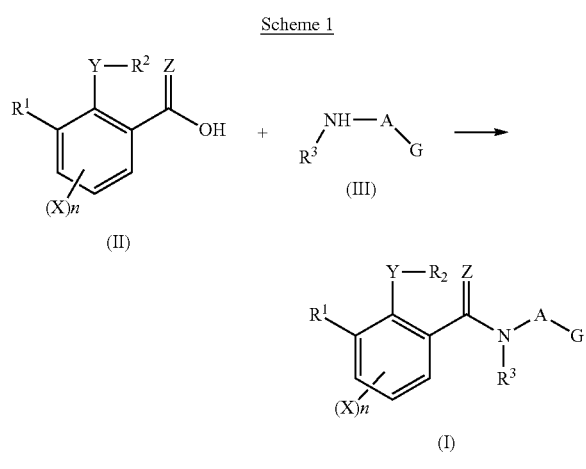

Scheme 1

Scheme 2

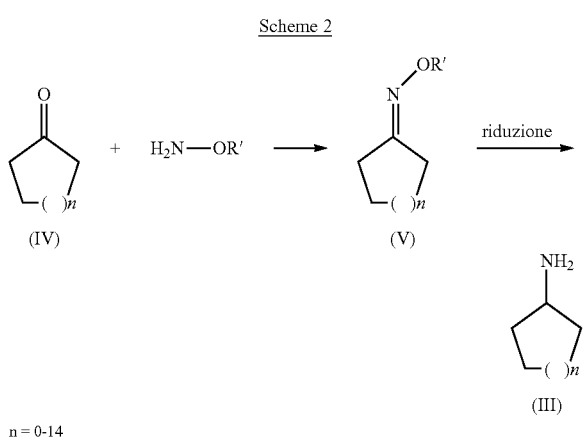

n = 0-14

The corresponding oximes having formula (V) can be converted to amines having general formula (III) by reduction with sodium in ethanol or with platinum, platinum oxide or nickel as catalysts in the presence of hydrogen, as described in WO2010010458.

Alternatively, the methyloximes can be reduced with sodium borohydride and trifluoroacetic acid in a solvent such as tetrahydrofuran or with sodium borohydride and zirconium chloride in tetrahydrofuran at temperatures ranging from 0° C. to the reflux temperature of the solvent, as described in N. Umino et al. in "Chem. Pharm. Bull" 1978, 26, 2897.

Alternatively, the compounds having formula (III), when they are not commercial and A has the meaning of $C_1$-$C_{12}$ alkyl and $R^3$ is hydrogen, can be obtained, for example, from the corresponding aldehyde or nitrile or azide or amide according to methods well known in literature and described in E. P. Kyba et al. "Tetrahedron Letters" (1977) 2737-2740, in Chen Feng et al. "Journal American Chemical Society" (2016) vol. 138 8781-8788, in Srinivasa, Nalina et al. in "Journal of Chemical Research" part S (2003) 630-631 or in G. Beamson et al. in "Journal of Catalysis" (2010) vol. 269 93-102. Again, the compounds having formula (II), when they are not commercial and A has the meaning of $C_1$-$C_{12}$ alkyl and $R^3$ is different from hydrogen, can be obtained either by reduction of the corresponding N-alkylamide or N-cycloalkylamide, for example with lithium aluminium hydride in tetrahydrofuran at temperatures ranging from 0° C. to the reflux temperature of the solvent as described in WO2010035032 or by reaction of the aldehyde having formula G-A-CHO with an appropriate alkylamine or cycloalkylamine having formula $R^3$—$NH_2$ and subsequent reduction of the imino-derivative thus obtained with methods known from literature, as described for example in WO2006100036.

The compounds having formula (II), as indicated in scheme 3, can be prepared by hydrolysis of the compound having formula (VII) wherein W has the meaning of methyl or ethyl or, if W has the meaning of a benzyl group, by hydrogenolysis with hydrogen in the presence of catalysts such as palladium on coal, using the methods indicated for example in Theodora W. Greene "Protective Groups in Organic Synthesis" Third Edition.

As is well known to skilled persons in the field, in order to obtain the compound having formula (VII) wherein $R^2$ is different from H, the alkylation of compound (VI) is carried out as indicated in scheme 3.

When $R^1$ represents the —NHCHO group, however, the Applicant has surprisingly discovered that the alkylation reaction of the —YH group leads to the formation of significant quantities of dialkylated product.

A further object of the present invention therefore relates to a process for the preparation of the compound having formula (I), comprising the preparation of the compound having formula (VI), wherein a compound $R^2$-Q is added to a mixture of the compound having formula (VI) dissolved in a suitable solvent, such as ethyl acetate, N,N-dimethylformamide or acetone, wherein Q represents an outgoing group such as a halogen or a mesylate or a triflate, preferably a halogen, more preferably an iodine atom at a temperature ranging from −15° C. to 0° C., in the presence of an organic or inorganic base such as potassium carbonate, sodium carbonate, sodium hydride, triethylamine or pyridine, optionally in the presence of a catalyst such as sodium iodide, potassium iodide or a crown ether such as 15-crown-5 or 18-crown-6 according to the reaction scheme 3.

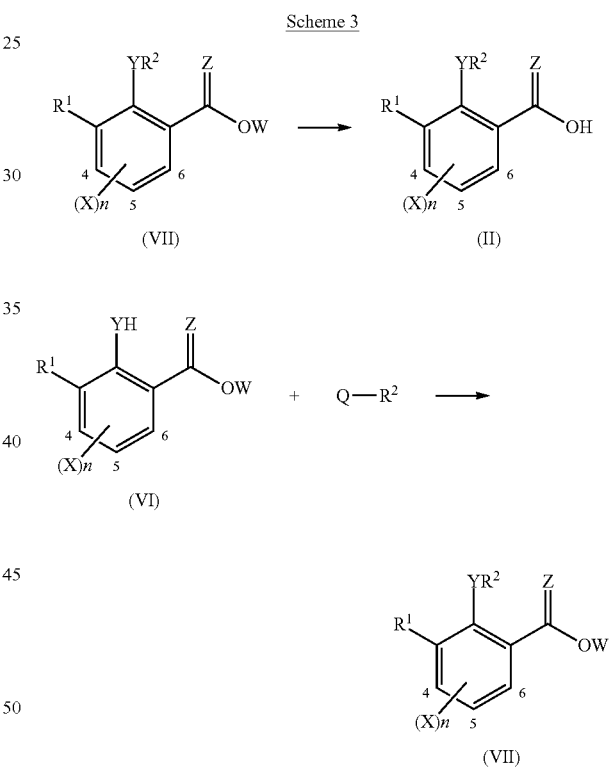

The compounds having general formula (I) can, alternatively, be obtained from the compounds having general formula (VIII) by alkylation reaction with a compound having formula $R^2$-Q wherein $R^2$ is different from H and Q represents a leaving group such as halogen, a mesylate or a triflate in ethyl acetate or N, N-dimethylformamide or acetone at a temperature ranging from −15° C. to 70° C., in the presence of an organic or inorganic base such as potassium carbonate, or sodium carbonate, or triethylamine or pyridine or sodium hydride in the presence or absence of a catalyst such as sodium iodide, potassium iodide and a crown ether such as 15-crown-5 or 18-crown-6 according to the reaction scheme 4.

Scheme 4

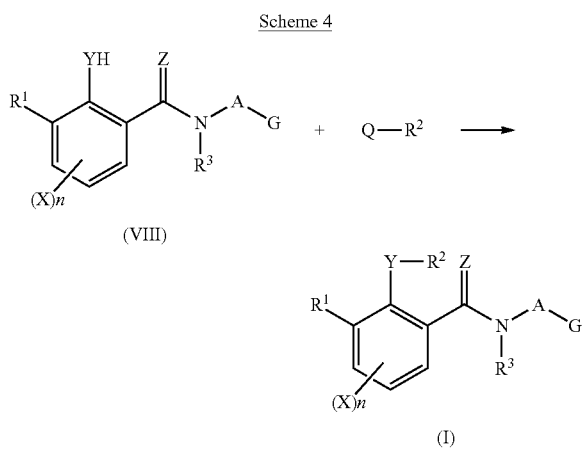

The compounds having general formula (VIII) wherein R² represents an H atom, can, in turn, be prepared from the compounds having general formula (IX) by reaction with a suitable amine R³—NH-A-G having formula (III) according to the reaction scheme 5.

Scheme 5

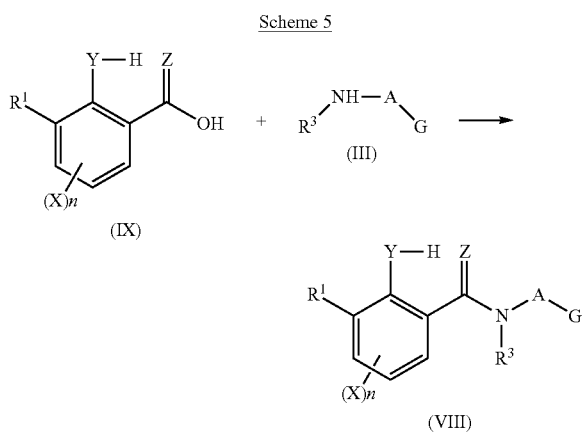

The reaction is carried out by activating the carboxylic acid through the corresponding chloride, for example with thionyl chloride in dichloromethane or chloroform or using a condenser such as N,N'-dicyclohexylcarbodiimide or N-(3-dimethylaminopropyl)-N'-ethylcarbodiimide in tetrahydrofuran or ethyl acetate, or using 1,1-carbonyldiimidazole in tetrahydrofuran or methylene chloride at temperatures ranging from 0° C. to the reflux temperature of the solvent used, as amply described in R. Larock "Comprehensive Organic Transformations".

The activated acid form is then reacted with the amine having formula (III) in a suitable solvent such as methylene chloride, or dichloroethane, or chloroform at a temperature ranging from 0° C. to the reflux temperature of the solvent, in the presence or absence of a base such as, for example, triethylamine or 4-dimethylaminopyridine, according to what is known in literature in R. Larock "Comprehensive Organic Transformations". The acids having general formula (IX) and the corresponding esters having formula (VI) are either commercial or can be synthesized according to methods known in literature and are easily available in the Reaxys Database (www.reaxys.com).

The compounds wherein Z has the meaning of S, can be prepared from the corresponding oxygenated compounds by reaction with phosphorus pentasulfide, or using the Lawesson reagent, in solvents such as toluene or dioxane at a temperature ranging from room temperature to the reflux temperature of the solvent as described in "Bioorganic and Medicinal Chemistry, 2018, vol. 26, pages 1547-1559".

A further object of the present invention relates to the use of the compounds having formula (I) for the control of phytopathogenic fungi of agricultural crops.

The compounds having general formula (I) are in fact provided with a very high fungicidal activity which is exerted with respect to numerous phytopathogenic fungi that attack important agricultural crops.

Examples of phytopathogenic fungi that can be effectively treated and fought with compounds having general formula (I) are those belonging to the classes of Basidiornycetes, Ascomycetes, Deuteromycetes or imperfect fungi, Oomycetes: *Puccinia* spp., *Ustilago* spp., *Tilletia* spp., *Uromyces* spp., *Phakopsora* spp., *Rhizoctonia* spp., *Eryiphe* spp., *Sphaerotheca* spp., *Podosphaera* spp., *Uncinula* spp., *Helminthosporium* spp., *Rhynchosporium* spp., *Pyrenophora* spp., *Monilinia* spp., *Sclerotinia* spp., *Septoria* spp. (*Mycosphaerella* spp.), *Venturia* spp., *Botrytis* spp., *Alternaria* spp., *Fusarium* spp., *Cercospora* spp., *Cercosporella herpotrichoides, Colletotrichum* spp., *Pyricularia oryzae, Sclerotium* spp., *Phytophtora* spp., *Pythium* spp., *Plasmopara viticola, Peronospora* spp., *Pseudoperonospora cubensis, Bremia* lactucae.

The main crops that can be protected with the compounds according to the present invention include cereals (wheat, barley, rye, oats, rice, corn, sorghum, etc.), fruit-trees (apples, pears, plums, peaches, almonds, cherries, bananas, vines, strawberries, raspberries, blackberries, etc.), citrus fruits (oranges, lemons, mandarins, grapefruit, etc.), legumes (beans, peas, lentils, soybeans, etc.), vegetables (spinach, lettuce, asparagus, cabbage, carrots, onions, tomatoes, potatoes, eggplants, peppers, etc.), cucurbits (pumpkins, courgettes, cucumbers, melons, watenrelons, etc.), oleaginous plants (sunflower, rapeseed, peanut, castor, coconut, etc.), tobacco, coffee, tea, cocoa, sugar beet, sugar cane, cotton.

In particular, the compounds having formula (I) have proved to be extremely effective in the control of *Plasnmopara viticola* on grapevines, *Phytophtora infestans* and *Botrytis cinerea* on tomatoes, *Puccinia recondita, Erisiphae graminis, Helminthosporium teres, Septoria nodoran, Septoria tritici* and *Fusariun* spp. on cereals, in the control of *Phakopsora pachYrhizi* on soybeans, in the control of *Uromyces appendicidatus* on beans, in the control of *Venturia inaequalis* on apple trees, in the control of *Sphaerotheca fuliginea* on cucumbers.

Furthermore, the compounds having general formula (I) are also effective in the control of phytopathogenic bacteria and viruses, such as for example *Xanihomonas* spp., *Pseudomonas* spp., *Erwinia amyovora*, the tobacco mosaic virus.

The compounds having formula (I) are capable of exerting a fungicidal action of both a curative and preventive nature and show an extremely low or zero phytotoxicity with respect to the crops treated.

For practical uses in agriculture, it is often preferable to use fungicidal compositions containing the compounds according to the present invention suitably formulated.

A further object of the present invention relates to fungicidal compositions comprising one or more compounds having formula (I), a solvent and/or solid or liquid diluent, possibly a surfactant.

The above-mentioned fungicidal compositions can be in the form of dry powders, wettable powders, emulsifiable concentrates, emulsions, micro-emulsions, pastes, granules, granules dispersible in water, solutions, suspensions, etc.: the selection of the type of composition depends on the specific use.

The fungicidal compositions are prepared according to known methods, for example by diluting or dissolving the active substance with a solvent medium and/or a solid or liquid diluent, possibly in the presence of surfactants.

Silica, kaolin, bentonite, talc, diatomaceous earth, dolomite, calcium carbonate, magnesia, gypsum, clays, synthetic silicates, attapulgite, seppiolite, can be used, for example, as solid diluents, or carriers.

Solvents or liquid diluents that can be used for example, in addition to water, are aromatic organic solvents (xylols or blends of alkyl benzenes, chlorobenzene, etc.), paraffins (petroleum fractions), alcohols (methanol, propanol, butanol, octanol, glycerin, etc.), esters (ethyl acetate, isobutyl acetate, alkyl carbonates, alkyl esters of adipic acid, alkyl esters of glutaric acid, alkyl esters of succinic acid, alkyl esters of lactic acid, etc.), vegetable oils (rapeseed oil, sunflower oil, soybean oil, castor oil, corn oil, peanut oil, and their alkyl esters), ketones (cyclohexanone, acetone, acetophenone, isophorone, ethylamylketone, etc.), amides (N,N-dimethylformanide, N-methylpyrrolidone, etc.), sulfoxides and sulfones (dimethyl sulfoxide, dimethylsulfone, etc.), and mixtures thereof.

Propellant gases such as butane, propane, halogenated hydrocarbons, nitrogen or carbon dioxide can be used as liquefied diluents or liquefied substances which gasify at room temperature and pressure.

Surfactants that can be used are sodium, calcium, potassium, triethylamine or triethanolamine salts of alkylnaphthalenesulfonates, poly-naphthalenesulfonates, alkylsulfonates, arylsulfonates, alkylarylsulfonates, polycarboxylates, sulfosuccinates, alkyl-sulfosuccinates, lignin sulfonates, alkyl sulfates; and furthermore polyethoxylated fatty alcohols, polyethoxylated alkylphenols, polyethoxylated or polypropoxy-polyethoxylated arylphenols or polyethoxylated esters of sorbitol, polyproproxy-polyethoxylates (block polymers), can also be used.

The fungicidal compositions can also contain special additives for particular purposes, for example antifreeze agents such as propylene glycol, or adhesion agents such as arabic gum, polyvinyl alcohol, polyvinylpyrrolidone, dispersing agents, for example lignin and its salts, cellulose derivatives or alginates, or stabilizers, for example antioxidants or ultraviolet-ray absorbents.

The concentration of active compound having formula (I) in the above compositions can vary within a wide range and depends on various factors. It varies in relation to the active compound having formula (I), the applications for which said compositions are destined, the environmental conditions and type of formulation adopted. In general, the concentration of active compound having formula (I) ranges from 0.1 to 90% by weight with respect to the total weight of the composition, preferably from 0.5 to 90% by weight.

If desired, it is possible to add to the fungicidal compositions containing the Compounds having general formula (I), other active ingredients compatible with the same, such as fungicides other than those having general formula (I), phytoregulators, antibiotics, herbicides, insecticides, fertilizers, biostimulants and/or mixtures thereof.

Examples of fungicides different from those having general formula (I) which can be included in the fungicidal compositions object of the present invention are: fluindapyr, acibenzolar, aldimorph, ametoctradin, amisulbrom, ampropylfos, anilazine, azaconazole, azithiram, azoxystrobin, benalaxyl, benalaxyl-M, benodanil, benomyl, benquinox, bentaluron, benthiavalicarb, benthoxazin, benzamacril, benzamorf, benzovindiflupyr, binapacryl, bitertanol, bixafen, blasticidin-S, boscalid, bromuconazole, bupirimate, buthiobate, captafol, captan, carbamorph, carbendazim, carboxin, carpropamid, chinomethionat, chlobenthiazone, chlorfenazole, chloroneb, chlorothalonil, chlorquinox, chlozolinate, cufraneb, cyazofamid, cycloheximide, cyflufenamid, cymoxanil, cypendazole, cyproconazole, cyprodinil, dazomet, debacarb, decafentin, dichlofluanid, dichlone, dichlorophen, dichlozoline, diclobutrazol, diclomezine, dicloran, diclocymet, diethofencarb, difenoconazole, diflumetorim, dimethirimol, dimethomorph, dimoxystrobin, diniconazole, dinobuton, dinocap, dinocton, dinopenton, dinosulfon, dinoterbon, dipyrithione, ditalimfos, dithianon, dodemorph, dodine, edifenphos, epoxiconazole, etaconazole, ethaboxam, ethirimol, ethoxyquin, etridiazole, famoxadone, fenamidone, fenaminosulf, fenapanil, fenarimol, fenbuconazole, fenfuram, fenhexamid, fenoxanil, fenpiclonil, fenpicoxamid, fenpropidin, fenpropimorph, fenpyrazamine, fentin, ferbam, ferimzone, fluazinam, fludioxonil, fluindapyr, flumetover, flumorph, fluopicolide, fluopyram, fluoroimide, fluotrimazole, fluoxastrobin, fluquinconazole, flusilazole, flusulfamide, flutianil, flutolanil, flutriafol, fluxapyroxad, folpet, fosetyl-aluminium, fuberidazole, furalaxyl, furametpyr, furcarbanil, furconazole, furconazole-cis, furophanate, guazatine, griseofulvin, halacrinate, hexaconazole, hexylthiofos, hymexazol, hydroxyquinoline sulfate, imazalil, imibenconazole, iminoctadine, inpyrfluxam, ipconazole, iprobenfos, iprodione, iprovalicarb, isofetamid, isoprothiolane, isopyrazam, isotianil, isovaledione, kasugamycin, kresoxim-methyl, mancopper, mancozeb, mandipropamid, maneb, mebenil, mecarbinzid, mepanipyrim, mepronil, meptyldinocap, metalaxyl, metalaxyl-M, metam, metconazole, methasulfocarb, methfuroxam, metiram, metominostrobin, metrafenone, metsulfovax, myclobutanil, myclozolin, nabam, natamycin, nicobifen, nitrothal-isopropyl, nuarimol, octhilinone, ofurace, orysastrobin, oxadixyl, oxathiapiprolin, oxpoconazole, oxycarboxin, pefurazoate, penconazole, pencycuron, penflufen, pentachlorofenol and its salts, penthiopyrad, phthalide, picoxystrobin, piperalin, Bordeaux mixture, polyoxins, probenazole, prochloraz, procymidone, propamocarb, propiconazole, propineb, proquinazid, prothiocarb, prothioconazole, pyracarbolid, pyraclostrobin, pyrametostrobin, pyraoxystrobin, pyrapropoyne, pyrazophos, pyribencarb, pyrifenox, pyrimethanil, pyriofenone, pyroquilon, pyroxyfur, quinacetol, quinazamid, quinconazole, quinoxyfen, quintozene, rabenzazole, copper hydroxide, copper oxychloride, copper (I) oxide, copper sulfate, sedaxane, silthiofam, simeconazole, spiroxamine, streptomycin, tebuconazole, tebufloquin, tetraconazole, thiabendazole, thiadifluor, thicyofen, thifluzamide, thiochlorfenphim, thiophanate, thiophanate-methyl, thioquinox, thiram, tiadinil, tioxymid, tolclofos-methyl, tolylfluanid, triadimefon, triadimenol, triamiphos, triarimol, triazbutil, triazoxide, tricyclazole, tridemorf, trifloxystrobin, triflumizole, triforine, triticonazole, uniconazole, uniconazole-P, validamycin, valifenalate, vinclozolin, zineb, ziram, sulfur, zoxamide.

A further object of the present invention therefore relates to fungicidal compositions comprising at least one compound having general formula (I) and at least another fungicide different from the compounds having formula (I).

Fungicidal compositions containing at least one amide having formula (I) and one or more known fungicides, particularly preferred for the particularly wide spectrum of action and a marked synergistic effect, are those in which one or more compounds having general formula (I) are combined with one or more known fungicides belonging to the following classes:

a) azoles selected from azaconazole, bitertanol, bromuconazole, cyproconazole, difenoconazole, epoxyconazole, fenbuconazole, fluquinconazole, flusilazole, flutriafol, hexaconazole, imazalil, ipconazole, metconazole, myclobutanil, penconazole, propiconazole, prochloraz, prothioconazole, simeconazole, tebuconazole, tetraconazole, triadimefon, triadimenol, triflumizole, triticonazole;

b) amines, ergosterol biosynthesis inhibitors selected from aldimorph, dodemorph, fenpropimorph, fenpropidin, spiroxamine, tridemorph;

c) succinate-dehydrogenase inhibitors (SDHI) selected from benzovindiflupyr, bixafen, boscalid, carboxin, fluindapyr, fluopyram, flutolanil, fluxapyroxad, furametpyr, isopyrazam, oxycarboxin, penflufen, penthiopyrad, sedaxane, thifluzamide;

d) strobilurins selected from azoxystrobin, dimoxystrobin, fluoxastrobin, kresoxim-methyl, metominostrobin, orysastrobin, picoxystrobin, pyraclostrobin, pyrametostrobin, pyraoxostrobin, trifloxystrobin;

e) specific antioidic compounds selected from cyflufenamid, flutianil, metrafenone, proquinazid, pyriofenone, quinoxyfen;

f) aniline-pyramidines selected from pyrimethanil, mepanipyrim, cyprodinil;

g) benzimidazoles and analogues thereof selected from carbendazim, benomyl, thiabendazole, thiophanate-methyl;

h) dicarboxyimides selected from iprodione, procymidone;

i) phtalimides selected from captafol, captan, folpet;

l) systemic acquired resistance (SAR) inducers selected from acibenzolar, probenazole, isotianil, tiadinil;

m) phenylpyrroles selected from fenpiclonil, fludioxonil;

n) acylalanines selected from benalaxyl, benalaxyl-M, furalaxyl, metalaxyl, metalaxyl-M;

o) other specific antiperonosporic compounds selected from ametoctradin, amisulbrom, benthiavalicarb, cyazofamid, cymoxanil, dimethomorph, ethaboxam, famoxadone, fenamidone, flumetover, flumorph, fluopicolide, iprovalicarb, mandipropamid, oxathiapiproline, valifenalate, zoxamide;

p) dithiocarbamates selected from maneb, mancozeb, propineb, zineb, metiram;

q) phosphorus acid and its inorganic or organic salts, fosetyl-aluninium r) cupric compounds selected from Bordeaux mixture, carpropamid, copper hydroxide, copper oxychloride, copper sulfate, copper salicylate;

s) other fungicides selected from chlorothalonil, fenhexamid, fenpyrazamine, fluazinam, silthiofarn, tebufloquin, zoxamide, dodine, guazatine, iminoctadine, tolclofos-methyl.

The fungicidal compounds are indicated in the present description with their international ISO name; the chemical structures and their CAS and IUPAC names are reported in Alan Wood's Website (www.alanwood.net), Compendium of Pesticide Common Names; the chemical-physical data and biological characteristics of most of these compounds are indicated in the "Pesticide Manual", C. D. S. Tomlin, 15th edition, 2009, British Crop Production Council.

The compound Fluindapyr has been described in patent application WO 2012/084812. Preferred compositions containing at least one compound having formula (I) (component A) and at least one other known fungicide are those consisting of:

C1: compound 1+tetraconazole;
C2: compound 1+tebuconazole;
C3: compound 1+epoxyconazole;
C4: compound 1+prothioconazole;
C5: compound 1+difenoconazole;
C6: compound 1+penconazole;
C7: compound 1+prochloraz;
C8: compound 1+fenpropimorph;
C9: compound 1+spiroxamine;
C10: compound 1+bixafen;
C11: compound 1+boscalid;
C12: compound 1+carboxin;
C13: compound 1+fluopyram;
C14: compound 1+fluxapyroxad;
C15: compound 1+isopyrazam;
C16: compound 1+penthiopyrad;
C17: compound 1+sedaxane;
C18: compound 1+azoxystrobin;
C19: compound 1+dimoxystrobin;
C20: compound 1+fluoxastrobin;
C21: compound 1+kresoxim-methyl;
C22: compound 1+picoxystrobin;
C23: compound 1+pyraclostrobin;
C24: compound 1+trifloxystrobin;
C25: compound 1+metrafenone;
C26: compound 1+proquinazid;
C27: compound 1+mepanipyrim;
C28: compound 1+cyprodinil;
C29: compound 1+iprodione;
C30: compound 1+procymidone;
C31: compound 1+carbendazim;
C32: compound 1+thiophanate-methyl;
C33: compound 1+fluindapyr;
C34: compound 1+benalaxyl-M;
C35: compound 1+fenpyrazamine;
C36: compound 1+fluazinam;
C37: compound 1+tolclofos-methyl;
C38: compound 1+mandipropamid;
C39: compound 1+copper oxychloride;
C40: compound 1+copper salicylate;
C41: compound 1+chlorothalonil;
C42: compound 1+cimoxanil;
C43: compound 1+dimetomorph;
C44: compound 1+oxathiopiproline;
C45: compound 1+fluopicolide;
C46: compound 2+tetraconazole;
C47: compound 2+tebuconazole;
C48: compound 2+epoxyconazole;
C49: compound 2+prothioconazole;
C50: compound 2+difenoconazole;
C51: compound 2+penconazole;
C52: compound 2+prochloraz;
C53: compound 2+fenpropimorph;
C54: compound 2+spiroxamine;
C55: compound 2+bixafen;
C56: compound 2+boscalid;
C57: compound 2+carboxin;
C58: compound 2+fluopyram;
C59: compound 2+fluxapyroxad;

C60: compound 2+isopyrazam;
C61: compound 2+penthiopyrad;
C62: compound 2+sedaxane;
C63: compound 2+azoxystrobin;
C64: compound 2+dimoxystrobin;
C65: compound 2+fluoxastrobin;
C66: compound 2+kresoxim-methyl;
C67: compound 2+picoxystrobin;
C68: compound 2+pyraclostrobin;
C69: compound 2+trifloxystrobin;
C70: compound 2+metrafenone;
C71: compound 2+proquinazid;
C72: compound 2+mepanipyrim;
C73: compound 2+cyprodinil;
C74: compound 2+iprodione;
C75: compound 2+procymidone;
C76: compound 2+carbendazim;
C77: compound 2+thiophanate-methyl;
C78: compound 2+fluindapyr;
C79: compound 2+benalaxyl-M;
C80: compound 2+fenpyrazamine;
C81: compound 2+fluazinam;
C82: compound 2+tolclofos-methyl;
C83: compound 2+mandipropamid;
C84: compound 2+copper oxychloride;
C85: compound 2+copper salicylate;
C86: compound 2+chlorothalonil;
C87: compound 2+cimoxanil;
C88: compound 2+dimetomorph;
C89: compound 2+oxathiopiproline;
C90: compound 2+fluopicolide;
C91: compound 4+tetraconazole;
C92: compound 4+tebuconazole;
C93: compound 4+epoxyconazole;
C94: compound 4+prothioconazole;
C95: compound 4+difenconazole;
C96: compound 4+penconazole;
C97: compound 4+prochloraz;
C98: compound 4+fenpropimorph;
C99: compound 4+spiroxamine;
C100: compound 4+bixafen;
C101: compound 4+boscalid;
C102: compound 4+carboxin;
C103: compound 4+fluopyram;
C104: compound 4+fluxapyroxad;
C105: compound 4+isopyrazam;
C106: compound 4+penthiopyrad;
C107: compound 4+sedaxane;
C108: compound 4+azoxystrobin;
C109: compound 4+dimoxystrobin;
C110: compound 4+fluoxastrobin;
C111: compound 4+kresoxim-methyl;
C112: compound 4+picoxystrobin;
C113: compound 4+pyraclostrobin;
C114: compound 4+trifloxystrobin;
C115: compound 4+metrafenone;
C116: compound 4+proquinazid;
C117: compound 4+mepanipyrim;
C118: compound 4+cyprodinil;
C119: compound 4+iprodione;
C120: compound 4+procymidone;
C121: compound 4+carbendazim;
C122: compound 4+thiophanate-methyl;
C123: compound 4+fluindapyr;
C124: compound 4+benalaxyl-M;
C125: compound 4+fenpyrazamine;
C125: compound 4+fluazinam;
C126: compound 4+tolclofos-methyl;
C127: compound 4+mandipropamid;
C128: compound 4+copper oxychloride;
C129: compound 4+copper salicylate;
C130: compound 4+chlorothalonil;
C131: compound 4+cimoxanil;
C132: compound 4+dimetomorph;
C133: compound 4+oxathiopiproline;
C134: compound 4+fluopicolide;
C135: compound 1+pyrachlostrobin;
C136: compound 1+zoxamide;
C137: compound 1+ametoctradin;
C138: compound 1+metiram;
C139: compound 1+potassium phosphite;
C140: compound 1+tetraconazole+azoxystrobin,
C141: compound 1+pyraclostrobin+tetraconazole;
C142: compound 1+epoxyconazole+azoxystrobin;
C143: compound 1+pyraclostrobin+epoxyconazole;
C144: compound 1+azoxystrobin+fluindapyr;
C145: compound 1+pyraclostrobin+fluindapyr;
C146: compound 1+fosetyl-aluminium+copper oxychloride;
C147: compound 1+fosetyl-aluminium+copper salicylate;
C148: compound 1+fluindapyr+tetraconazole;
C149: compound 4+tetraconazole+azoxystrobin;
C150: compound 4+pyraclostrobin+tetraconazole;
C151: compound 4+azoxystrobin+fluindapyr;
C152: compound 4+fluindapyr+tetraconazole;
C153: compound 10+tetraconazole;
C154: compound 10+tebuconazole;
C155: compound 10+epoxyconazole;
C156: compound 10 prothioconazole;
C157: compound 10+difenoconazole;
C158: compound 10+penconazole;
C159: compound 10+prochloraz;
C160: compound 10+fenpropimorph;
C161: compound 10+spiroxamine;
C162: compound 10+bixafen;
C163: compound 10+boscalid;
C164: compound 10+carboxin;
C165: compound 10+fluopyram;
C166: compound 10+fluxapyroxad;
C167: compound 10+isopyrazam;
C168: compound 10+penthiopyrad;
C169: compound 10+sedaxane;
C170: compound 10+azoxystrobin;
C171: compound 10+dimoxystrobin;
C172: compound 10+fluoxastrobin;
C173: compound 10+kresoxim-methyl;
C174: compound 10+picoxystrobin;
C175: compound 10+pyraclostrobin;
C176: compound 10+trifloxystrobin;
C177: compound 10+metrafenone;
C178: compound 10+proquinazid;
C179: compound 10+mepanipyrim;
C180: compound 10+cyprodinil;
C181: compound 10+iprodione;
C182: compound 10+procymidone;
C183: compound 10+carbendazim;
C184: compound 10+thiophanate-methyl;
C185: compound 10+fluindapyr;
C186: compound 10+benalaxyl-M;
C187: compound 10+fenpyrazamine;
C188: compound 10+fluazinam;
C189: compound 10+tolclofos-methyl;
C190: compound 10+mandipropamid;

C191: compound 10+copper oxychloride;
C192: compound 10+copper salicylate;
C193: compound 10+chlorothalonil;
C194: compound 10+cimoxanil;
C195: compound 10+dimetomorph;
C196: compound 10+oxathiopiproline;
C197: compound 10+fluopicolide;
C198: compound 106+tetraconazole;
C199: compound 106+tebuconazole;
C200: compound 106+epoxyconazole;
C201: compound 106+prothioconazole;
C202: compound 106+difenoconazole;
C203: compound 106+penconazole;
C204: compound 106+prochloraz;
C205: compound 106+fenpropimorph;
C206: compound 106+spiroxamine;
C208: compound 106+bixafen;
C209: compound 106+boscalid;
C210: compound 106+carboxin;
C211: compound 106+fluopyram;
C212: compound 106+fluxapyroxad;
C213 compound 106+isopyrazam;
C214: compound 106+penthiopyrad;
C215: compound 106+sedaxane;
C216: compound 106+azoxystrobin;
C217: compound 106+dimoxystrobin;
C218: compound 106+fluoxastrobin;
C219: compound 106+kresoxim-methyl;
C220: compound 106+picoxystrobin;
C221: compound 106+pyraclostrobin;
C222: compound 106+trifloxystrobin;
C223: compound 106+metrafenone;
C224: compound 106+proquinazid;
C225: compound 106+mepanipyrim;
C226: compound 106+cyprodinil;
C227: compound 106+iprodione;
C228: compound 106+procymidone;
C229: compound 106+carbendazim;
C230: compound 106+thiophanate-methyl;
C231: compound 106+fluindapyr;
C232: compound 106+benalaxyl-M;
C233: compound 106+fenpyrazamine;
C234: compound 106+fluazinam;
C235: compound 106+tolclofos-methyl;
C236: compound 106+mandipropamid;
C237: compound 106+copper oxychloride;
C238: compound 106+copper salicylate;
C239: compound 106+chlorothalonil;
C240: compound 106+cimoxanil;
C241: compound 106+dimetomorph;
C242: compound 106+oxathiopiproline;
C243: compound 106+fluopicolide;
C244: compound 107+tetraconazole;
C245: compound 107+tebuconazole;
C246: compound 107+epoxyconazole;
C247: compound 107+prothioconazole;
C248: compound 107+difenoconazole;
C249: compound 107+penconazole;
C250: compound 107+prochloraz;
C251: compound 107+fenpropimorph;
C252: compound 107+spiroxamine;
C253: compound 107+bixafen;
C254: compound 107+boscalid;
C255: compound 107+carboxin;
C256: compound 107+fluopyram;
C257: compound 107+fluxapyroxad;
C258: compound 107+isopyrazam;
C259: compound 107+penthiopyrad;
C260: compound 107+sedaxane;
C261: compound 107+azoxystrobin;
C262: compound 107+dimoxystrobin;
C263: compound 107+fluoxastrobin;
C264: compound 107+kresoxim-methyl;
C265: compound 107+picoxystrobin;
C266: compound 107+pyraclostrobin;
C267: compound 107+trifloxystrobin;
C268: compound 107+metrafenone;
C269: compound 107+proquinazid;
C270: compound 107+mepanipyrim;
C271: compound 107+cyprodinil;
C272: compound 107+iprodione;
C273: compound 107+procymidone;
C274: compound 107+carbendazim;
C275: compound 107+thiophanate-methyl;
C276: compound 107+fluindapyr;
C277: compound 107+benalaxyl-M;
C278: compound 107+fenpyrazamine;
C279: compound 107+fluazinam;
C280: compound 107+tolclofos-methyl;
C281: compound 107+mandipropamid;
C282: compound 107+copper oxychloride;
C283: compound 107+copper salicylate;
C284: compound 107+chlorothalonil;
C285: compound 107+cimoxanil;
C286: compound 107+dimetomorph;
C287: compound 107+oxathiopiproline;
C288: compound 107+fluopicolil;
C289: compound 10+tetraconazole+azoxystrobin,
C290: compound 10+pyraclostrobin+tetraconazole;
C291: compound 10+epoxyconazole+azoxystrobin;
C292: compound 10+pyraclostrobin+epoxyconazole;
C293: compound 10+azoxystrobin+fluindapyr;
C294: compound 10+pyraclostrobin+fluindapyr;
C295: compound 10+fosetyl-aluminium+copper oxychloride;
C296: compound 10+fosetyl-aluminium+copper salicylate;
C297: compound 10+fluindapyr+tetraconazole;
C298: compound 106+tetraconazole+azoxystrobin,
C299: compound 106+pyraclostrobin+tetraconazole;
C300: compound 106+epoxyconazole+azoxystrobin;
C301: compound 106+pyraclostrobin+epoxyconazole;
C302: compound 106+azoxystrobin+fluindapyr;
C303: compound 106+pyraclostrobin+fluindapyr;
C304: compound 106+fosetyl-aluminium+copper oxychloride;
C305: compound 106+fosetyl-aluminium+copper salicylate;
C306: compound 106+fluindapyr+tetraconazole;
C307: compound 107+tetraconazole+azoxystrobin,
C308: compound 107+pyraclostrobin+tetraconazole;
C309: compound 107+epoxyconazole+azoxystrobin;
C310: compound 107+pyraclostrobin+epoxyconazole;
C311: compound 107+azoxystrobin+fluindapyr;
C312: compound 107+pyraclostrobin+fluindapyr;
C313: compound 107+fosetyl-aluminium+copper oxychloride;
C314: compound 107+fosetyl-aluminium+copper salicylate;
C315: compound 107+fluindapyr+tetraconazole Component A, i.e. the compounds having general formula (I), of the previous compositions C1-C315 are described and exemplified in Table 1 and specifically these are the following compounds having general formula (I) wherein the substituents have the meanings indicated hereunder:

| Comp. | R¹ | R² | R³ | Y | Z | X | n | A | G |
|---|---|---|---|---|---|---|---|---|---|
| 1. | NHCHO | (isopropyl ester group) | H | O | O | — | 0 | — | (cyclohexyl group) |
| 2. | NHCHO | (tert-butyl ester group) | H | O | O | — | 0 | — | (cyclohexyl group) |
| 4. | NR²CHO | (isopropyl ester group) | H | O | O | — | 0 | — | (cyclohexyl group) |
| 10. | NHCHO | (isopropyl ester group) | H | O | O | — | | 0 | (cyclohexyl group) |
| 106 | NHCHO | COCH₃ | H | O | S | — | | 0 | (cyclohexyl group) |
| 107 | NHCHO | COCH₃ | H | O | S | — | | 0 | (cyclohexyl group) |

The synergistic effect of the compositions containing a compound having general formula (I) (component A) and a known fungicide (component B), can be evaluated by applying the Colby formula ("Weeds, 1967, 15, pages 20-22):

$$Et=EA+EB-(EA \times EB):100$$

wherein Et is the percentage of expected effectiveness for the composition containing compounds A and B at the doses dA+dB, EA is the percentage of effectiveness observed for component A at the dose dA, EB is the percentage of effectiveness observed for component B at the dose dB.

When the effectiveness observed for the composition A+B (EA+B) is higher than the expected effectiveness according to the Colby formula (EA+B/Et>1), there is a synergistic effect.

In the case of ternary combinations, the Colby formula has the form:

$$Et=EA+EB1+EB2-(EA \times EB1+EA \times EB2+EB1 \times EB2)/100$$

wherein Et is the percentage of expected effectiveness for the composition containing compounds A, B1 and B2 at the doses dA+dB1+dB2, EA is the percentage of effectiveness observed for component A at the dose dA, EB1 is the percentage of effectiveness observed for component B1 at the dose dB1, EB2 is the percentage of effectiveness observed for component B2 at the dose dB2.

When the effectiveness observed for the composition A+B1+B2 (EA+B1+B2) is higher than the expected effectiveness according to the Colby formula (EA+B1+B2/Et>1), there is a synergistic effect.

A further object of the present invention therefore relates to the use of the compositions comprising at least one amide having general formula (I) for the control of phytopathogenic fungi in agricultural crops.

The main crops which can be protected with the compositions comprising at least one compound having formula (I), alone or combined with at least one other known active ingredient, comprise cereals (wheat, barley, rye, oats, rice, corn, sorghum, etc.), fruit-trees (apples, pears, plums, peaches, almonds, cherries, bananas, grape-vines, strawberries, raspberries, blackberries, etc.), citrus fruit (oranges, lemons, mandarins, grapefruit, etc.), legumes (beans, peas, lentils, soybeans, etc.), vegetables (spinach, lettuce, asparagus, cabbage, carrots, onions, tomatoes, potatoes, eggplants, peppers, etc.), cucurbits (pumpkins, zucchini, cucumbers, melons, watermelons, etc.), oleaginous plants (sunflower, rapeseed, peanut, castor, coconut, etc.); tobacco, coffee, tea, cocoa, sugar beet, sugar cane, cotton, nuts.

In particular, the compositions of the present invention have proved to be extremely effective in the control of *Plasmopara viticola* on vines, *Phyophlora infestans* and *Botrytis cinerea* on tomatoes, *Phytophtora infestans* on potatoes, *Puccinia recondita, Erysiphe graminis, Helminthosporium teres, Septoria* spp and *Fusarium* spp. on cereals, in the control of *Phakopsora pachyrhizi* on soybeans, in the control of *Uromyces appendculatus* on beans, in the control of *Venturi Inaequalis* on apple trees, in the control of *Sphaerotheca Fuliginea* on cucumbers.

Furthermore, the compositions of the present invention are also effective in the control of soil fungi, such as, for example, *Rhizoctonia solani, Sclerotinia* spp, *Pythium ultimum* on horticultural plants.

The compositions of the present invention are also effective in the control of phytopathogenic bacteria and viruses, preferably *Xanthomonas* spp., *Pseudomonas* spp., *Erwinia amylovora*, the tobacco mosaic virus.

The compositions object of the present invention are capable of exerting a fungicidal action which can be of a curative, preventive or eradicative nature, and, in general, exhibit a very low or zero phytotoxicity on the crops treated.

If the compositions comprise a compound having general formula (I) and at least one known active ingredient, the weight ratios in the above compositions vary according to the compounds selected and can normally range from 1:100 to 100:1, preferably from 1:10 to 10:1.

The total concentration of the active components in the above compositions can vary within a wide range; they generally range from 1% to 99% by weight with respect to the total weight of the composition, preferably from 5 to 90% by weight with respect to the total weight of the composition.

The application of these compositions can take place on any part of the plant, for example on the leaves, stems, branches and roots, or on the seeds themselves before sowing, or on the soil in which the plant grows.

A further object of the present invention therefore relates to a method for controlling phytopathogenic fungi in agricultural crops, which consists in applying effective and non-phytotoxic doses of compounds comprising at least one compound having formula (I), and, optionally, one or more known active ingredients compatible with the same, on any part of the plant to be protected or on the soil.

The concentration of the amide compounds having general formula (I) in the above-mentioned compositions can vary within a wide range; in general, it ranges from 1% to 90% by weight with respect to the total weight of the composition, preferably from 5 to 50% by weight with respect to the total weight of the composition.

The application of these compositions can take place on any part of the plant, for example on the leaves, stems, branches and roots, or on the seeds themselves before sowing, or on the soil in which the plant grows.

A further object of the present invention therefore relates to a method for the control of phytopathogenic fungi in agricultural crops, which consists in applying effective doses of the compounds having formula (I), used as such or formulated in fungicidal compositions as described above.

The quantity of compound to be applied for obtaining the desired effect can vary according to various factors such as, for example, the compound used, the crop to be preserved, the type of pathogen, the degree of infection, the climatic conditions, the method of application, the formulation adopted.

Doses of compound ranging from 10 g to 5 kg per hectare of agricultural crop generally provide a sufficient control.

The following examples are provided for a better understanding of the invention, and should be considered illustrative and non-limitative of the same.

EXAMPLE 1

Preparation of 3-formylamino-2 hydroxy-N-(3,3,5,5-tetramethylcyclohexyl) benzamide A solution, prepared separately, obtained by dissolving 4.25 g of N-(3-dimethylaminopropyl)-N'-ethylcarbodiimide chlorohydrate (22.2 mmoles) and 3.10 ml of triethylamine (22.2 mmoles) in 100 ml of dichloromethane, was added dropwise on an ice bath, at about 0° C., to a suspension of 2.68 g of 3-formylamino salicylic acid (14.8 mmoles), 2.30 g of 3,3,5,5-tetramethylcyclohexylamine (14.8 mmol) and 3.40 g of 1-hydroxybenzotriazole (22.2 mmoles) in 100 ml of dichloromethane. After an hour, the reaction mixture was left to return to room temperature and was left under stirring at this temperature for 24 hours.

After GC-MS and LC-MS control, the reaction mixture was washed with water and the phases were separated. The aqueous phase was re-extracted using dichloromethane and the organic phase was joined and washed twice with water and then with a saturated solution of sodium chloride, anhydrified on sodium sulfate, filtered and evaporated to give 5.12 g of product.

The product thus obtained was purified by silica gel chromatography, eluting with heptane/ethyl acetate 9:1. 4.19 g of the desired product were obtained.

Yield 88.5%.

LC-MS: $M^+$=318

EXAMPLE 2

Preparation of 3-formylamino-2-[(2-methyl-propanoyl-oxy)methoxy]-N-(3,3,5,5-tetramethylcyclohexyl)benzamide [Compound nr. 1]

4.19 g of 3-formylamino-2-hydroxy-N-(3,3,5,5-tetramethylcyclohexyl) benzamide (13.2 mmoles) dissolved in 45 ml of anhydrous N,N-dimethylformamide, were added, at −10° C., to a suspension of 0.58 g of sodium hydride (14.5 mmoles) at 60% in hexane, in 75 ml of anhydrous N,N-dimethylformamide. The reaction mixture was left at this temperature for 10 minutes, and 4.53 g of iodomethyl isobutyrate (19.80 mmoles) in 30 ml of N,N-dimethylformamide were then added dropwise and the reaction mixture was left at this temperature for about 1 hour.

After GC-MS and LC-MS control, the reaction mixture was poured into water and ice, recovered with ethyl acetate, washed twice with water and then with a saturated solution of sodium chloride, anhydrified on sodium sulfate, filtered and evaporated to give 5.1 of raw product.

The product thus obtained was purified by means of silica gel chromatography, eluting with heptane/ethyl acetate 9:1. 3.95 g of the desired product were obtained.

Yield 71.6%

LC-MS: $M^+$=418

EXAMPLE 3

Preparation of 3-(N'-formyl-N'-[(2-methylpropanoyl-oxy)methyl]amino)-2-[(2-methylpropanoyloxy)methoxy]-N-(3,3,5,5-tetramethylcyclohexyl)-benzamide [Compound nr. 4]

4.19 g of 3-formylamino-2-hydroxy-N-(3,3,5,5-tetramethylcyclohexyl) benzamide (13.2 mmoles) dissolved in 45 ml of N,N-dimethylformamide were added at −10° C. to a suspension of 1.32 g of sodium hydride (33.0 mmoles) at 60% in hexane, in 75 ml of anhydrous N,N-dimethylformamide.

The reaction mixture was left for ten minutes at this temperature, and 9.06 g of iodomethyl isobutyrate (39.60 mmoles) in 30 ml of anhydrous N,N-dimethylformamide were then added dropwise and the reaction mixture was left to return to room temperature and left under stirring for 3 hours.

After GC-MS and LC-MS control, the reaction mixture was poured into water and ice, recovered with ethyl acetate, washed twice with water and then with a saturated solution of sodium chloride, anhydrified on sodium sulfate, filtered and evaporated to give 7.21 of raw product.

The product thus obtained was purified by means of silica gel chromatography, eluting with heptane/ethyl acetate 9:1. 5.82 g of the desired product were obtained.

Yield 85.1%
LC-MS: $M^+$=518

EXAMPLE 4

Preparation of 2-hydroxy-3-nitro-N-(3,3,5,5-tetramethylcyclohexyl)-benzamide

A solution, prepared separately, obtained by dissolving 4.25 g of N-(3-dimethylaminopropyl)-N'-ethylcarbodiimide chlorohydrate (22.2 mmoles) and 3.10 ml of triethylamine (22.2 mmoles) in 100 ml of dichloromethane, was added dropwise on an ice bath, at about 0° C., to a suspension of 2.72 g of 3-nitro salicylic acid (14.8 mmoles), 2.30 g of 3,3,5,5-tetramethylcyclohexylamine (14.8 mmoles) and 3.40 g of 1-hydroxybenzotriazole (22.2 mmoles) in 100 ml of dichloromethane. After an hour, the reaction mixture was left to return to room temperature and was left under stirring at this temperature for 24 hours.

After GC-MS and LC-MS control, the reaction mixture was washed with water and the phases were separated. The aqueous phase was re-extracted with dichloromethane and the organic phase was joined and washed twice with water and then with a saturated solution of sodium chloride, anhydrified on sodium sulfate, filtered and evaporated to give 4.95 g of product which was used as such for the subsequent reaction.

LC-MS: $M^+$=320

EXAMPLE 5

Preparation of 3-amino-2-hydroxy-N-(3,3,5,5-tetramethylcyclohexyl)-benzamide 0.45 g of Pd/C at 10% (0.10% w/w) were added, under a nitrogen atmosphere, to a solution of 4.95 g of 2-hydroxy-3-nitro-N-(3,3,5,5-tetramethylcyclohexyl)benzamide (14.8 mmoles theoretical) in 220 ml of ethyl acetate and the reaction mixture was hydrogenated in an autoclave at 3 bars and 30° C. for 24 hours.

After GC-MS and LC-MS control, the reaction mixture was filtered on celite to eliminate the catalyst, washed twice with water and then with a saturated solution of sodium chloride, anhydrified on sodium sulfate, filtered and evaporated to give 4.02 g of raw product which was used as such for the subsequent reaction. Yield 93.6%.

LC-MS: $M^+$=290

EXAMPLE 6

Preparation of 3-(N',N'-bis(2-methylpropanoyloxy) methyl]amino)-2-[(2-methylpropanoyloxy) methoxy]-N-(3,3,5,5-tetramethylcyclohexyl) benzamide [Compound nr. 7]

4.02 g of 3-amino-2-hydroxy-N-(3,3,5,5-tetramethylcyclohexyl)benzamide (13.8 mmoles theoretical) dissolved in 45 ml of N,N-dimethylformamide were added, at −10° C., to a suspension in 75 ml of anhydrous N,N-dimethylformamide, of 2.21 g of sodium hydride (55.20 mmoles) al 60% in hexane. The reaction mixture was left for 10 minutes at this temperature and 12.64 g of iodomethyl isobutyrate (55.20 mmoles) in 60 ml of N,N-dimethylformamide were then added dropwise and the reaction mixture was left to return to room temperature and left under stirring for 4 hours.

After GC-MS and LC-MS control, the reaction mixture was poured into water and ice, recovered with ethyl acetate, washed twice with water and then with a saturated solution of sodium chloride, anhydrified on sodium sulfate, filtered and evaporated to give 9.62 g of raw product.

The product thus obtained was purified by means of silica gel chromatography, eluting with heptane/ethyl acetate 9:1. 7.53 g of the desired product were obtained.

Yield 92.5%.
LC-MS: $M^+$=590

EXAMPLE 7

Preparation of 3-formylamino-2-hydroxy-N-(3,3,5,5-tetramethylcyclohexyl) benzamide A suspension of 4.02 g of 3-amino-2-hydroxy-N-(3,3,5,5-tetramethylcyclohexyl)benzamide (13.8 mmoles theoretical) in 11.5 ml of formamide was stirred and heated to 150° C. for an hour.

After GC-MS and LC-MS control, the reaction mixture was poured into water, extracted twice with ethyl acetate, then anhydrified on sodium sulfate, filtered and evaporated to give 4.40 g of raw product which was purified on silica gel, eluting with a mixture of heptane/ethyl acetate 6:4, obtaining 3.5 g of the desired product.

Yield 80.1%
LC-MS: $M^+$=318

EXAMPLE 8

Preparation of Compounds nr. 2, 3, 5, 6, 8-107

Compounds nr. 2, 3, 5, 6, 8-107 having formula (I) indicated in Table 2, were obtained by operating analogously to what is described in the previous examples.

TABLE 2
| Comp. | R¹ | R² | R³ | Y | Z | A | X | n | G |
|---|---|---|---|---|---|---|---|---|---|
| 1. | NHCHO | 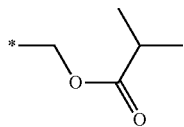 | H | O | O | — | | 0 | 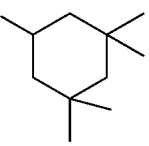 |
| 2. | NHCHO | 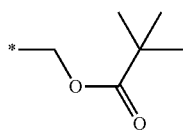 | H | O | O | — | | 0 | 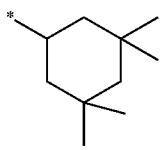 |
| 3. | NHCHO | 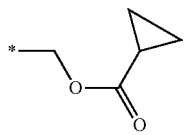 [SMILES: *COC(=O)C1CC1] | H | O | O | — | | 0 | 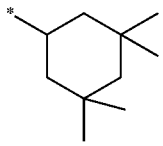 |
| 4. | NR²CHO | 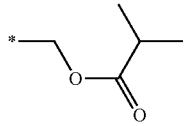 | H | O | O | — | | 0 | 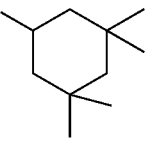 |
| 5. | NR²CHO | 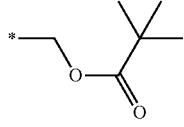 | H | O | O | — | | 0 | 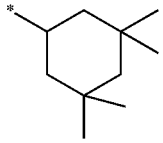 |
| 6. | NR²CHO | 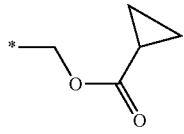 [SMILES: *COC(=O)C1CC1] | H | O | O | — | | 0 | 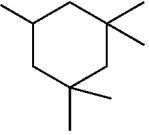 |
| 7. | NR₂² | 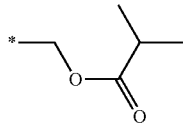 [SMILES: *COC(=O)C(C)C] | H | O | O | — | | 0 | 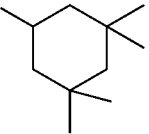 |
| 8. | NR₂² | 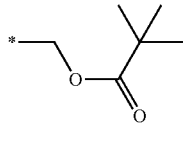 [SMILES: *COC(=O)C(C)(C)C] | H | O | O | — | | 0 | 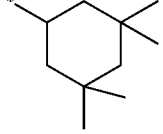 |
| 9. | NR₂² | 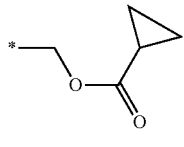 [SMILES: *COC(=O)C1CC1] | H | O | O | — | | 0 | 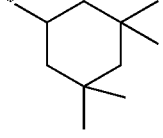 |
| 10. | NHCHO | 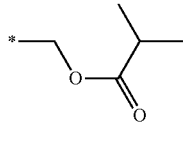 | H | O | O | — | | 0 | 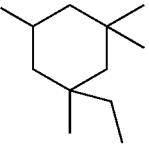 |

TABLE 2-continued
| Comp. | R¹ | R² | R³ | Y | Z | A | X | n | G |
|---|---|---|---|---|---|---|---|---|---|
| 11. | NHCHO | 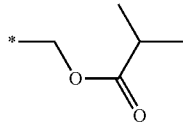 | H | O | O | — | | 0 | 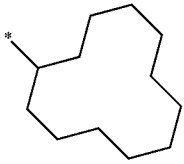 [SMILES: *C1CCCCCCCCCCC1] |
| 12. | NHCHO | 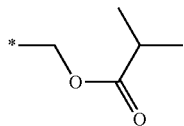 [SMILES: *COC(=O)C(C)C] | H | O | O | — | | 0 | 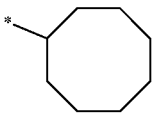 [SMILES: *C1CCCCCCC1] |
| 13. | NHCHO | 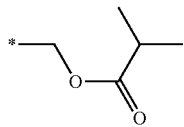 | H | O | O | — | | 0 | 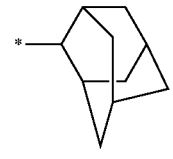 [SMILES: *C1C2CC3CC(C2)CC1C3] |
| 14. | NHCHO | 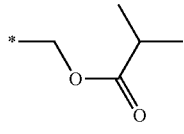 [SMILES: *COC(=O)C(C)C] | H | O | O | — | | 0 | 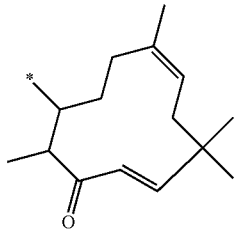 |
| 15. | NHCHO | 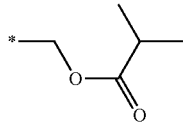 | H | O | O | — | | 0 | 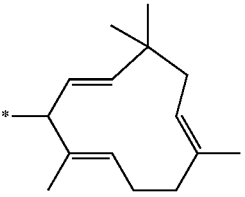 [SMILES: *C1/C=C/C(C)(C)C/C=C(\C)CC/C=C/1C] |
| 16. | NHCHO | 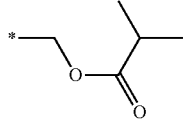 [SMILES: *COC(=O)C(C)C] | H | O | O | — | | 0 | 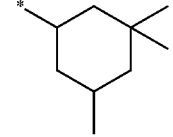 |
| 17. | NHCHO | 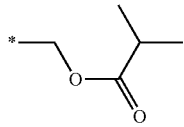 | H | O | O | — | | 0 | 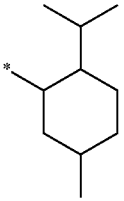 [SMILES: *C1CC(C)CCC1C(C)C] |
| 18. | NHCHO | 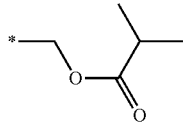 [SMILES: *COC(=O)C(C)C] | H | O | O | — | | 0 |  |
| 19. | NHCHO | 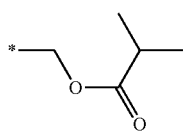 | H | O | O | — | | 0 | 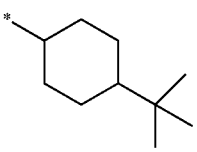 [SMILES: *C1CCC(C(C)(C)C)CC1] |

TABLE 2-continued
| Comp. | R¹ | R² | R³ | Y | Z | A | X | n | G |
|---|---|---|---|---|---|---|---|---|---|
| 20. | NHCHO | 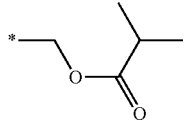 [SMILES: *COC(=O)C(C)C] | CH₃ | O | O | — | | 0 | 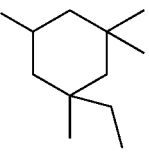 |
| 21. | NHCHO | 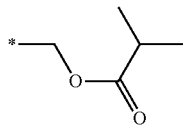 | CH₃ | O | O | — | | 0 | 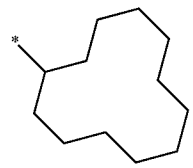 [SMILES: *C1CCCCCCCCCCC1] |
| 22. | NHCHO | 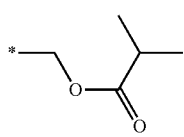 | CH₃ | O | O | — | | 0 | 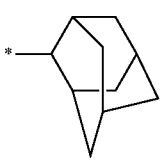 [SMILES: *C1C2CC3CC(C2)CC1C3] |
| 23. | NHCHO | 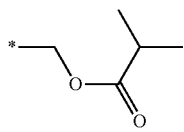 [SMILES: *COC(=O)C(C)C] | H | S | O | — | | 0 | 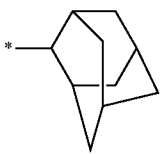 [SMILES: *C1C2CC3CC(C2)CC1C3] |
| 24. | OCH₃ | 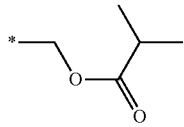 | H | S | O | — | | 0 | 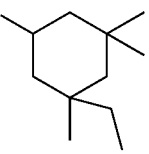 |
| 25. | NHCHO | 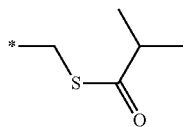 [SMILES: *CSC(=O)C(C)C] | H | S | O | — | | 0 | 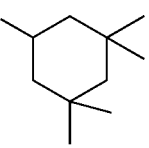 |
| 26. | NHCHO | 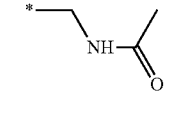 | H | O | O | — | | 0 | 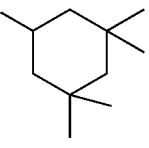 |
| 27. | NHCHO | 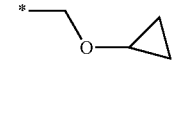 | H | O | O | — | | 0 | 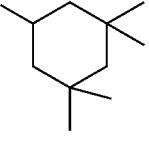 |
| 28. | NHCHO | 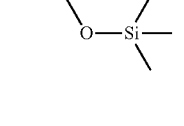 | H | O | O | — | | 0 | 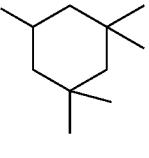 |
| 29. | NHCHO | 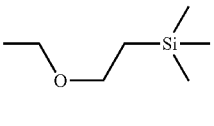 | H | O | O | — | | 0 | 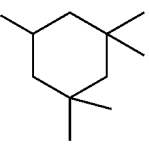 |

TABLE 2-continued
| Comp. | R¹ | R² | R³ | Y | Z | A | X | n | G |
|---|---|---|---|---|---|---|---|---|---|
| 30. | NHCHO | 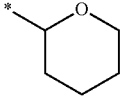 | H | O | O | — | | 0 | 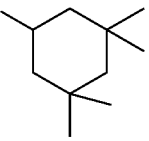 |
| 31. | NHCHO | 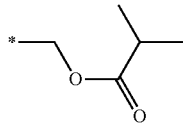 [SMILES: *COC(=O)C(C)C] | H | O | O | $CH_2$ | | 0 | 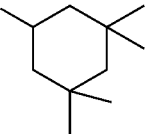 |
| 32. | NHCHO | 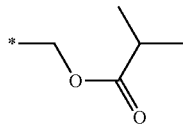 [SMILES: *COC(=O)C(C)C] | H | O | O | $CH_2$ | | 0 | 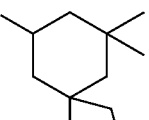 |
| 33 | $OCH_3$ | 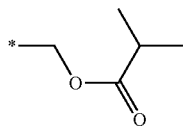 [SMILES: *COC(=O)C(C)C] | H | O | O | — | 5-Cl | 1 | 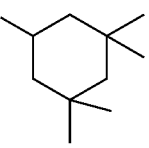 |
| 34 | $OCH_3$ | 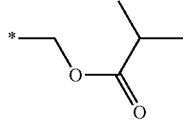 [SMILES: *COC(=O)C(C)C] | H | O | O | — | 6-Br | 1 | 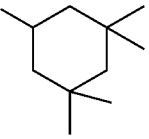 |
| 35 | $OCH_3$ | 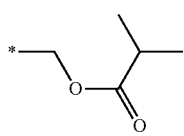 [SMILES: *COC(=O)C(C)C] | H | O | O | — | 4-$NO_2$ | 1 | 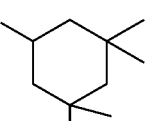 |
| 36 | NHCHO | 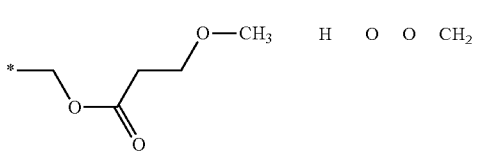 | H | O | O | $CH_2$ | | 0 | 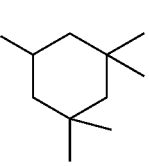 |
| 37 | NHCHO | 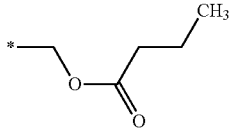 | H | O | O | $CH_2$ | | 0 | 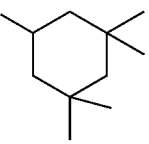 |
| 38 | NHCHO | 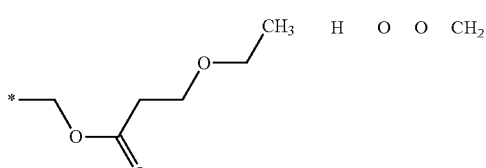 | H | O | O | $CH_2$ | | 0 | 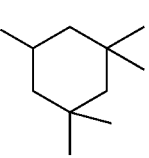 |

TABLE 2-continued
| Comp. | R¹ | R² | R³ | Y | Z | A | X | n | G |
|---|---|---|---|---|---|---|---|---|---|
| 39 | NHCHO |  | H | O | O | — |  | 0 | 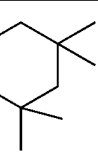 |
| 40 | NHCHO | 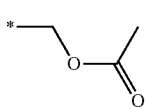 | H | O | O | — |  | 0 | 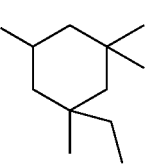 |
| 41 | NHCHO | 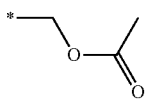 [SMILES: *COC(C)=O] | H | S | O |  |  | 0 | 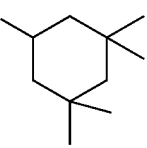 |
| 42 | NHCHO | 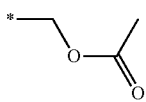 | H | S | O | — |  | 0 | 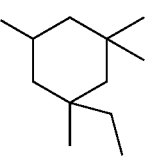 |
| 43 | NHCHO | 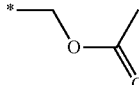 | H | O | O | — |  | 0 |  |
| 44 | NHCHO | 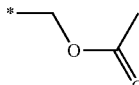 | H | S | O | — |  | 0 |  |
| 45 | NHCHO | 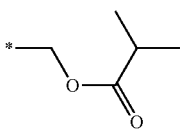 [SMILES: *COC(=O)C(C)C] | H | O | O | — |  | 0 | 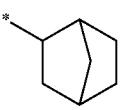 [SMILES: *C1CC2CCC1C2] |
| 46 | NHCHO | 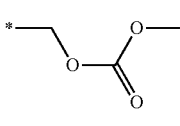 | H | O | O | — |  | 0 | 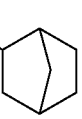 |
| 47 | NHCHO | 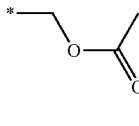 | H | O | O | — |  | 0 | 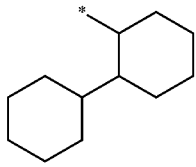 |
| 48 | NHCHO | 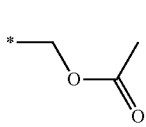 | H | S | O | — |  | 0 | 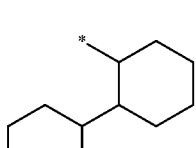 |

TABLE 2-continued
| Comp. | R¹ | R² | R³ | Y | Z | A | X | n | G |
|---|---|---|---|---|---|---|---|---|---|
| 49 | NHCHO | 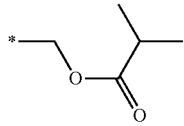 | H | O | O | — | | 0 | 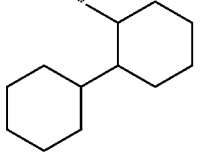 |
| 50 | NHCHO | 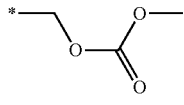 [SMILES: *COC(=O)OC] | H | O | O | — | | 0 | 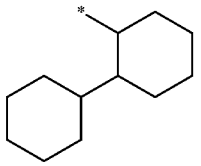 [SMILES: *C1CCCCC1C1CCCCC1] |
| 51 | NHCHO | H | H | O | O | — | | 0 | 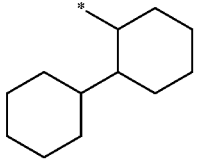 [SMILES: *C1CCCCC1C1CCCCC1] |
| 52 | NHCHO | COCH₃ | H | O | O | — | | 0 | 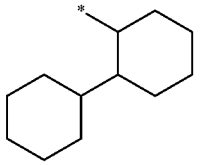 |
| 53 | NHCHO | 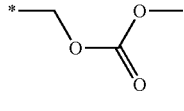 | H | O | O | — | | 0 | 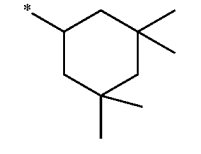 |
| 54 | NHCHO | 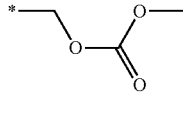 | H | O | O | — | | 0 | 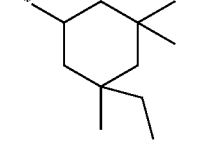 |
| 55 | NHCHO | 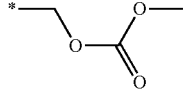 [SMILES: *COC(=O)OC] | H | O | O | — | | 0 | 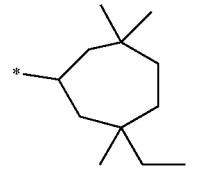 [SMILES: *C1CC(C)(C)CCC(C)(CC)C1] |
| 56 | NHCHO | 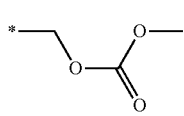 [SMILES: *COC(=O)OC] | H | O | O | — | | 0 | 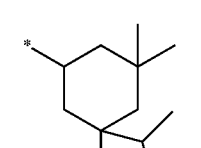 |
| 57 | NHCHO | 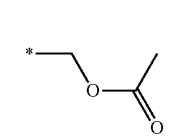 | H | O | O | — | | 0 | 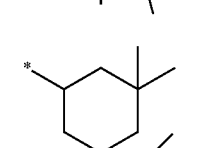 |

TABLE 2-continued

| Comp. | R¹ | R² | R³ | Y | Z | A | X | n | G |
|---|---|---|---|---|---|---|---|---|---|
| 58 | NHCHO | *-CH₂-O-C(=O)-CH(CH₃)₂ | H | O | O | — | | 0 | 3,5,5-trimethylcyclohexyl |
| 59 | NHCHO | *-CH₂-O-C(=O)-CH₃ | H | O | O | — | | 0 | 4,4-diethyl-cycloheptyl |
| 60 | NHCHO | *-CH₂-O-C(=O)-CH(CH₃)₂ | H | O | O | — | | 0 | 4,4-diethyl-cycloheptyl |
| 61 | NHCHO | *-CH₂-O-C(=O)-CH₃ | H | O | O | — | | 0 | 3,3,6,6-tetramethylcyclooctyl |
| 62 | NHCHO | *-CH₂-O-C(=O)-CH(CH₃)₂ | H | O | O | — | | 0 | 3,3,6,6-tetramethylcyclooctyl |
| 63 | NHCHO | *-CH₂-O-C(=O)-O-CH₃ | H | O | O | — | | 0 | 3,3,6,6-tetramethylcyclooctyl |
| 64 | NHCHO | *-CH₂-S-C(=O)-CH(CH₃)₂ | H | S | O | — | | 0 | 3-ethyl-5,5-dimethylcyclohexyl |
| 65 | NHCHO | *-CH₂-NH-C(=O)-CH₃ | H | O | O | — | | 0 | 3-ethyl-5,5-dimethylcyclohexyl |
| 66 | NHCHO | *-CH₂-O-cyclopropyl | H | O | O | — | | 0 | 3-ethyl-5,5-dimethylcyclohexyl |

TABLE 2-continued
| Comp. | R¹ | R² | R³ | Y | Z | A | X | n | G |
|---|---|---|---|---|---|---|---|---|---|
| 67 | NHCHO | 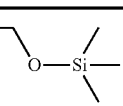 | H | O | O | — |  | 0 | 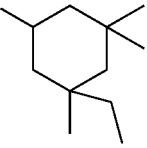 |
| 68 | NHCHO | 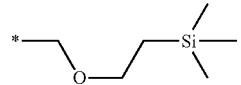 | H | O | O | — |  | 0 | 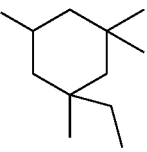 |
| 69 | NHCHO | 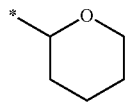 | H | O | O | — |  | 0 | 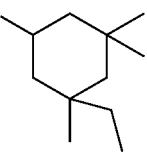 |
| 70 | NHCHO | 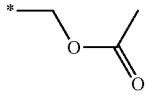 [SMILES: *COC(C)=O] | H | O | O | $CH_2$ |  | 0 | 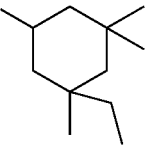 |
| 71 | NHCHO | H | H | O | O | — |  | 0 | 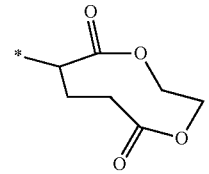 |
| 72 | NHCHO | $COCH_3$ | H | O | O | — |  | 0 | 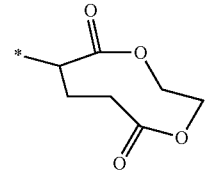 |
| 73 | NHCHO | 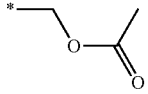 [SMILES: *COC(C)=O] | H | O | O | — |  | 0 | 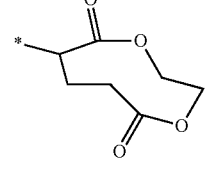 |
| 74 | NHCHO | 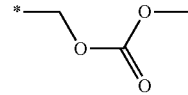 [SMILES: *COC(=O)OC] | H | O | O | — |  | 0 | 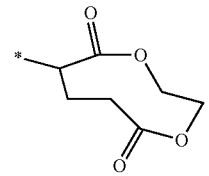 [SMILES: *C1CCC(=O)OCCOC1=O] |
| 75 | NHCHO | 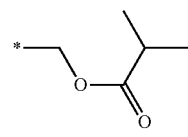 | H | O | O | — |  | 0 | 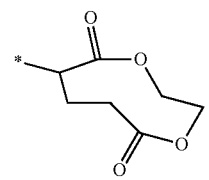 [SMILES: *C1CCC(=O)OCCOC1=O] |

TABLE 2-continued
| Comp. | R¹ | R² | R³ | Y | Z | A | X | n | G |
|---|---|---|---|---|---|---|---|---|---|
| 76 | NHCHO | H | H | O | O | — | | 0 | 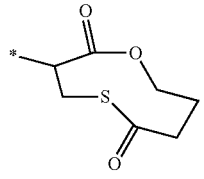 [SMILES: *C1CSC(=O)CCCOC1=O] |
| 77 | NHCHO | COCH₃ | H | O | O | — | | 0 | 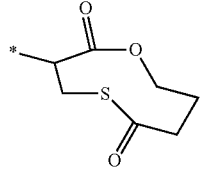 [SMILES: *C1CSC(=O)CCCOC1=O] |
| 78 | NHCHO | 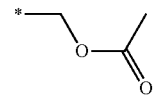 | H | O | O | — | | 0 | 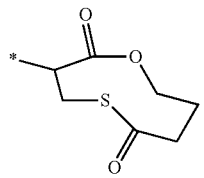 [SMILES: *C1CSC(=O)CCCOC1=O] |
| 79 | NHCHO | 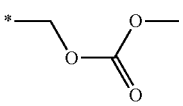 | H | O | O | — | | 0 | 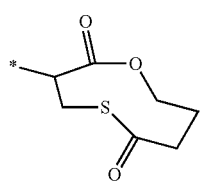 |
| 80 | NHCHO | 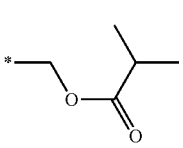 | H | O | O | — | | 0 | 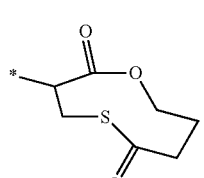 |
| 81 | NHCHO | H | H | O | O | — | | 0 | 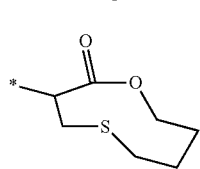 |
| 82 | NHCHO | COCH₃ | H | O | O | — | | 0 | 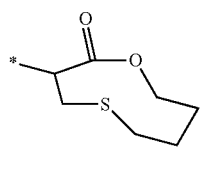 [SMILES: *C1CSCCCCOC1=O] |
| 83 | NHCHO | 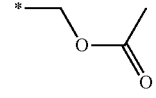 | H | O | O | — | | 0 | 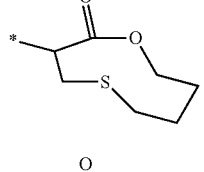 |
| 84 | NHCHO | 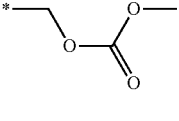 | H | O | O | — | | 0 | 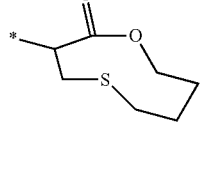 |

TABLE 2-continued

| Comp. | R¹ | R² | R³ | Y | Z | A | X | n | G |
|---|---|---|---|---|---|---|---|---|---|
| 85 | NHCHO | *-CH₂-O-C(=O)-CH(CH₃)₂ | H | O | O | — | | 0 | (2-oxo-1,4-oxathiepan-3-yl) |
| 86 | NHCHO | H | H | O | O | — | | 0 | (5,5-dimethyl-2,6-dioxomorpholin-3-yl) |
| 87 | NHCHO | *-CH₂-O-C(=O)-CH(CH₃)₂ | H | O | O | — | | 0 | (5,5-dimethyl-2,6-dioxomorpholin-3-yl) |
| 88 | NHCHO | COCH₃ | H | O | O | — | | 0 | (5,5-dimethyl-2,6-dioxomorpholin-3-yl) |
| 89 | NHCHO | *-CH₂-O-C(=O)-CH₃ | H | O | O | — | | 0 | (5,5-dimethyl-2,6-dioxomorpholin-3-yl) |
| 90 | NHCHO | *-CH₂-O-C(=O)-O-CH₃ | H | O | O | — | | 0 | (5,5-dimethyl-2,6-dioxomorpholin-3-yl) |
| 91 | NHCHO | *-CH₂-O-C(=O)-CH(CH₃)₂ | H | O | S | — | | 0 | (3,3,5,5-tetramethylcyclohexyl) |
| 92 | NHCHO | *-CH₂-O-C(=O)-C(CH₃)₃ | H | O | S | — | | 0 | (3,3,5,5-tetramethylcyclohexyl) |
| 93 | NHCHO | *-CH₂-O-C(=O)-cyclopropyl | H | O | S | — | | 0 | (3,3,5,5-tetramethylcyclohexyl) |

TABLE 2-continued

| Comp. | R¹ | R² | R³ | Y | Z | A | X | n | G |
|---|---|---|---|---|---|---|---|---|---|
| 94. | NHCHO | (isobutyrate -CH₂-O-C(O)-CH(CH₃)₂) | H | O | S | — | | 0 | (3,3,5-trimethyl-5-ethylcyclohexyl) |
| 95 | NHCHO | (-CH₂-O-C(O)-CH₃) | H | O | S | — | | 0 | (3,3,5-trimethyl-5-ethylcyclohexyl) |
| 96 | NHCHO | (-CH₂-O-C(O)-CH₃) | H | O | S | — | | 0 | (bicyclohexyl) |
| 97 | NHCHO | (-CH₂-O-C(O)-CH₃) | H | O | S | — | | 0 | (trimethyl-ethyl cycloheptyl) |
| 98 | NHCHO | (-CH₂-O-C(O)-CH(CH₃)₂) | H | O | S | — | | 0 | (trimethyl-ethyl cycloheptyl) |
| 99 | NHCHO | (-CH₂-O-C(O)-CH(CH₃)₂) | H | O | S | — | | 0 | (tetramethyl cyclooctyl) |
| 100 | NHCHO | (-CH₂-O-C(O)-O-CH₃) | H | O | S | — | | 0 | (tetramethyl cyclooctyl) |
| 101 | NHCHO | COCH₃ | H | O | S | — | | 0 | (dioxo-dioxecane ring) |
| 102 | NHCHO | (-CH₂-O-C(O)-CH(CH₃)₂) | H | O | S | — | | 0 | (dioxo-dioxecane ring) |

TABLE 2-continued

| Comp. | R¹ | R² | R³ | Y | Z | A | X | n | G |
|---|---|---|---|---|---|---|---|---|---|
| 103 | NHCHO | COCH₃ | H | O | S | — |  | 0 | (thiolactone/lactone bicyclic structure with *) |
| 104 | NHCHO | *—CH₂—O—C(=O)—CH(CH₃)₂ (isobutyrate ester) | H | O | S | — |  | 0 | (thiolactone/lactone bicyclic structure with *) |
| 105 | NHCHO | *—CH₂—O—C(=O)—CH(CH₃)₂ (isobutyrate ester) | H | O | S | — |  | 0 | (morpholinedione with gem-dimethyl and NH, with *) |
| 106 | NHCHO | COCH₃ | H | O | S | — |  | 0 | (3-ethyl-3,5,5-trimethylcyclohexyl with *) |
| 107 | NHCHO | COCH₃ | H | O | S | — |  | 0 | (3,3,5,5-tetramethylcyclohexyl with *) |

Table 3 shows the results of the GC-MS analyses on the samples 2, 3, 5, 6, 8-107.

TABLE 3

| Compound Nr. | LC-MS: M+ |
|---|---|
| 2. | 432 |
| 3. | 416 |
| 5. | 546 |
| 6. | 514 |
| 8. | 632 |
| 9. | 584 |
| 10. | 432 |
| 11. | 446 |
| 12. | 390 |
| 13. | 414 |
| 14. | 398 |
| 15. | 482 |
| 16. | 404 |
| 17. | 418 |
| 18. | 416 |
| 19. | 418 |
| 20. | 446 |
| 21. | 460 |
| 22. | 428 |
| 23. | 430 |
| 24. | 436 |
| 25. | 450 |
| 26. | 389 |
| 27. | 338 |
| 28. | 420 |
| 29. | 448 |
| 30. | 402 |
| 31. | 546 |
| 32. | 446 |
| 33 | 425 |
| 34. | 470 |
| 35. | 436 |
| 36. | 448 |
| 37. | 432 |
| 38. | 462 |
| 39. | 391 |
| 40. | 405 |
| 41. | 407 |
| 42. | 421 |
| 43. | 347 |
| 44. | 363 |
| 45. | 375 |
| 46. | 363 |
| 47. | 417 |
| 48. | 433 |
| 49. | 445 |
| 50. | 433 |
| 51. | 345 |
| 52. | 387 |
| 53. | 407 |
| 54. | 421 |
| 55. | 435 |
| 56. | 435 |
| 57. | 419 |

TABLE 3-continued

| Compound Nr. | LC-MS: M+ |
|---|---|
| 58. | 447 |
| 59. | 419 |
| 60. | 447 |
| 61. | 419 |
| 62. | 447 |
| 63. | 435 |
| 64. | 449 |
| 65. | 404 |
| 66. | 403 |
| 67. | 435 |
| 68. | 473 |
| 69. | 417 |
| 70. | 419 |
| 71. | 337 |
| 72. | 379 |
| 73. | 409 |
| 74. | 425 |
| 75. | 437 |
| 76. | 353 |
| 77. | 395 |
| 78. | 425 |
| 79. | 441 |
| 80. | 453 |
| 81. | 339 |
| 82. | 381 |
| 83. | 411 |
| 84. | 427 |
| 85. | 439 |
| 86. | 350 |
| 87. | 450 |
| 88. | 392 |
| 89. | 422 |
| 90. | 438 |
| 91. | 435 |
| 92. | 449 |
| 93. | 433 |
| 94. | 449 |
| 95. | 421 |
| 96. | 433 |
| 97. | 435 |
| 98. | 463 |
| 99. | 463 |
| 100. | 451 |
| 101. | 395 |
| 102. | 453 |
| 103. | 411 |
| 104. | 469 |
| 105. | 466 |
| 106. | 377 |
| 107. | 391 |

EXAMPLE 9

Determination of the Preventive Fungicidal Activity (5 Days) Against *Puccinia recondita* on Wheat Leaves of wheat plants of the Salgemma variety, grown in pots in a conditioned environment at 20° C. and 70% of Relative Humidity (RH) were treated by spraying both sides of the leaves with the compound under examination (see Table 4 hereunder) dispersed in a hydroacetone solution at 20% by volume of acetone.

After remaining 5 days in a conditioned environment, the plants were sprayed on both sides of the leaves with an aqueous suspension of conidia of *Puccinia recondita* (2 mg of inoculum per 1 ml of solution for infection).

After spraying, the plants were kept in a humidity-saturated environment at a temperature ranging from 18 to 24° C. for the incubation period of the fungus (1 day).

At the end of this period, the plants were put in a greenhouse with a relative humidity (RH) of 70% and at a temperature of 18-24° C. for 14 days.

At the end of this period, the external symptoms of the pathogen appeared and it was therefore possible to proceed with the visual evaluation of the intensity of the infection, both on the parts treated directly with the products (T) and on the parts developed during the implementation of the test (NT).

The fungicidal activity is expressed as a percentage of the reduction, with respect to non-treated seedlings (comparison), in the area of the leaf affected by the disease (100=full effectiveness; 0=zero effectiveness).

All of the compounds 1, 2, 3, 5 showed full activity (100%) at the dosage of 250 ppm. At the same time, an evaluation of the phytotoxicity was effected (percentage of leaf necrosis) induced on the wheat seedlings by the application of the products: in this case the evaluation scale ranges from 0 (completely healthy plant) to 100 (completely necrotic plant).

Table 4 indicates the results obtained by carrying out the test described with compounds 1, 2, and 4 compared with compound 504 described in WO9927783:

CR1: 3-formylamino-2-hydroxy-N-(3,3,5,5-tetramethylcyclohexyl)benzamide

TABLE 4

| | | P5 activity | |
|---|---|---|---|
| Compound Nr. | ppm | T | NT |
| 1 | 125 | 70 | 60 |
| | 250 | 75 | 65 |
| 2 | 125 | 60 | 55 |
| | 250 | 70 | 65 |
| 4 | 125 | 70 | 65 |
| | 250 | 80 | 70 |
| CR1 | 125 | 50 | 35 |
| | 250 | 65 | 50 |

EXAMPLE 10

Determination of the Preventive Activity (7 Days) of the Compounds Having Formula (I) Against *Plasmopara viticola* on Vines Leaves of vine plants of the Merlot variety, grown in pots, in a conditioned environment, (20±1° C., 70% of R.H.) were treated by spraying both sides with the compound under examination.

7 days after the treatment, the plants were inoculated with an aqueous suspension of spores of *Plasmopara viticola* (200,000 spores/cc) by spraying both sides of the leaves with a compressed air gun.

After remaining 24 hours in a humidity-saturated environment, at 21° C. the plants were transferred for an incubation period (7 days) in a conditioned environment at 70% of R H. and at 24° C.

At the end of this period, the external symptoms of the pathogen appeared and it was therefore possible to proceed with the evaluation of the intensity of the infection.

The fungicidal activity was expressed as the reduction percentage, with respect to non-treated seedlings, in the area of the leaf affected by the disease (100=full effectiveness; 0=zero effectiveness).

Table 5 indicates the results obtained by carrying out the test described with compounds nr. 1, 2 and 4 compared with compound 504 described in WO9927783.

CR1: 3-formylamino-2-hydroxy-N-(3,3,5,5-tetramethylcyclohexyl)benzamide

TABLE 5

| Compound Nr | ppm | P7 activity |
| --- | --- | --- |
| 1 | 30 | 100 |
|  | 125 | 100 |
| 2 | 30 | 95 |
|  | 125 | 100 |
| 4 | 30 | 100 |
|  | 125 | 100 |
| CR1 | 30 | 50 |
|  | 125 | 65 |

EXAMPLE 11

Determination of the Fungicidal Activity of the Compounds Having Formula (I) Against Helmintosporium *Teres* on Barley Leaves of barley plants (cultivar Gemini), grown in pots in a conditioned environment (20±1° C., 70% of R.H.), were treated by spraying both sides of the leaves with the compounds under examination, dispersed in a hydro-acetate solution at 20% by volume of acetone.

After remaining 5 days in a conditioned environment, the plants were sprayed on both sides of the leaves with an aqueous suspension of conidia of Helmintosporium *teres* (50,000 conidia per $cm^3$ (adding Tween 20-1 drop/100 ml).

The plants were then kept in a controlled environment during the incubation period of the fungus (1 day wet room for infection, 3 days in a cell with R.H. 70% and 0° C. for the incubation period, 3 days for wet room evasion, 12 days biological cycle).

At the end of this period (12 days), the fungicidal activity was evaluated according to an evaluation percentage scale from 0 (plant completely infected) to 100 (healthy plant).

Table 6 indicates the results obtained by carrying out the test described with compound nr. 1 compared with compound 504 described in WO9927783.

CR1: 3-formylamino-2-hydroxy-N-(3,3,5,5-tetramethylcyclohexyl)benzamide

TABLE 6

| Compound Nr | ppm | P7 activity |
| --- | --- | --- |
| 1 | 125 | 75 |
|  | 250 | 80 |
| CR1 | 125 | 5 |
|  | 250 | 15 |

The invention claimed is:

1. An amide having general formula (I):

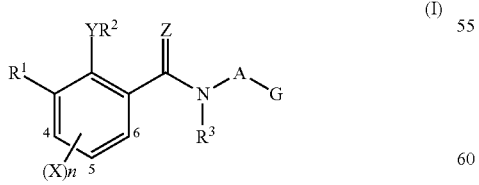

wherein:

$R^1$ represents a $C_1$-$C_{12}$ alkoxyl, a $C_1$-$C_{12}$ haloalkoxyl, a $C_3$-$C_{18}$ cycloalkyl, a —$NR^4R^5$ group;

$R^2$ represents a $C_2$-$C_{13}$ acyl, a $C_2$-$C_{12}$ alkanoyloxyalkyl $C_1$-$C_{12}$, a $C_2$-$C_{12}$ haloalkanoyloxyalkyl $C_1$-$C_{12}$, a $C_1$-$C_{12}$ alkoxy-$C_1$-$C_{12}$-alkanoyloxyalkyl $C_1$-$C_{12}$, a $C_1$-$C_{12}$ haloalkoxy-$C_1$-$C_{12}$-alkanoyloxyalkyl $C_1$-$C_{12}$, a $C_3$-$C_{18}$ cycloalkoxy-$C_1$-$C_{12}$-alkanoyloxyalkyl $C_1$-$C_{12}$, an aryloxy $C_1$-$C_{12}$ alkanoyloxyalkyl $C_1$-$C_{12}$, a benzyloxy $C_1$-$C_{12}$ alkanoyloxyalkyl $C_1$-$C_{12}$, a $C_4$-$C_{18}$ cycloalkanoyloxyalkyl $C_1$-$C_{12}$, a $C_1$-$C_{12}$ aroyloxyalkyl, a $C_1$-$C_{12}$ benzoyloxyalkyl, a $C_1$-$C_{12}$ heterocyclylcarbonyloxyalkyl, a $C_1$-$C_{12}$ alkyloxyalkyl $C_1$-$C_{12}$, a $C_1$-$C_{12}$ haloalkyloxyalkyl $C_1$-$C_{12}$, a $C_1$-$C_{12}$ alkoxy-$C_1$-$C_{12}$-alkyloxyalkyl $C_1$-$C_{12}$, a $C_1$-$C_{12}$ haloalkoxy-$C_1$-$C_{12}$-alkyloxyalkyl $C_1$-$C_{12}$, a $C_3$-$C_{18}$ cycloalkoxy $C_1$-$C_{12}$-alkyloxyalkyl $C_1$-$C_{12}$, an aryloxy $C_1$-$C_{12}$-alkyloxyalkyl $C_1$-$C_{12}$, a benzyloxy $C_1$-$C_{12}$-alkyloxyalkyl $C_1$-$C_{12}$, a $C_3$-$C_{18}$ cycloalkyloxyalkyl $C_1$-$C_{12}$, a $C_1$-$C_{12}$ aryloxyalkyl, a $C_1$-$C_{12}$ benzyloxyalkyl; a $C_1$-$C_{12}$ heterocyclyloxyalkyl, a $C_4$-$C_{12}$ alkanoylthioalkyl $C_1$-$C_{12}$, a $C_2$-$C_{12}$ haloalkanoylthioalkyl $C_1$-$C_{12}$, a $C_4$-$C_{18}$ cycloalkanoylthioalkyl $C_1$-$C_{12}$, a $C_1$-$C_{12}$ aroylthioalkyl, a $C_1$-$C_{12}$ benzoylthioalkyl; a $C_1$-$C_{12}$ heterocyclylcarbonylthioalkyl, a $C_1$-$C_{12}$ alkylthioalkyl $C_1$-$C_{12}$, a $C_1$-$C_{12}$ haloalkylthioalkyl $C_1$-$C_{12}$, a $C_1$-$C_{12}$ alkoxy-$C_1$-$C_{12}$-alkylthioalkyl $C_1$-$C_{12}$, a $C_1$-$C_{12}$ haloalkoxy-$C_1$-$C_{12}$-alkylthioalkyl $C_1$-$C_{12}$, a $C_3$-$C_{18}$ cycloalkoxy $C_1$-$C_{12}$-alkylthioalkyl $C_1$-$C_{12}$, a $C_1$-$C_{12}$ aryloxy alkylthioalkyl $C_1$-$C_{12}$, a $C_1$-$C_{12}$ benzyloxy alkylthioalkyl $C_1$-$C_{12}$, a $C_3$-$C_{18}$ cycloalkylthioalkyl $C_1$-$C_{12}$, a $C_1$-$C_{12}$ benzylthioalkyl, a $C_1$-$C_{12}$ arylthioalkyl, a $C_1$-$C_{12}$ heterocyclylthioalkyl, a $C_2$-$C_{12}$ alkanoylaminoalkyl $C_1$-$C_{12}$, a $C_2$-$C_{12}$ haloalkanoylaminoalkyl $C_1$-$C_{12}$, a $C_4$-$C_{18}$ cycloalkanoylaminoalkyl $C_1$-$C_{12}$, a $C_1$-$C_{12}$ aroylaminoalkyl, a $C_1$-$C_{12}$ benzoylaminoalkyl, a $C_1$-$C_{12}$ heterocyclylcarbonylaminoalkyl, a $C_1$-$C_{12}$ heterocyclylaminoalkyl, a $C_4$-$C_{18}$ cycloalkylaminoalkyl $C_1$-$C_{12}$, a tetrahydropyranyl, a $C_1$-$C_{12}$ trimethylsilyloxyalkyl, a $C_1$-$C_{12}$ trimethylsilylethoxyalkyl;

$R^1$ and $R^2$ together with the carbon atoms to which they are bound can form a 1,3-oxazole ring;

$R^3$ represents a hydrogen atom, a $C_1$-$C_{12}$ alkyl, a $C_3$-$C_{18}$ cycloalkyl;

$R^4$ and $R^5$, the same or different, represent a hydrogen atom, an aminocarbonyl group, a methylaminocarbonyl group, a dimethylaminocarbonyl group, a $C_1$-$C_{12}$ alkyl, a formyl, a $C_2$-$C_{13}$ acyl, a $C_2$-$C_{13}$ haloalkylcarbonyl, a benzyl group, an aroyl group, an $C_2$-$C_{13}$ alkoxycarbonyl, a $C_1$-$C_{12}$ alkoxyalkyl $C_1$-$C_{12}$; a $C_1$-$C_{12}$ alkanoyloxyalkyl $C_1$-$C_{12}$, a $C_1$-$C_{12}$ haloalkanoyloxyalkyl $C_1$-$C_{12}$, a $C_3$-$C_{18}$ cycloalkanoyloxyalkyl $C_1$-$C_{12}$, a $C_1$-$C_{12}$ aroyloxyalkyl, a $C_1$-$C_{12}$ heterocyclylcarbonyloxyalkyl, a $C_1$-$C_{12}$ aryloxyalkyl, a $C_1$-$C_{12}$ heterocyclyloxyalkyl, a $C_1$-$C_{12}$ alkanoylthioalkyl $C_1$-$C_{12}$, a $C_1$-$C_{12}$ halo-alkanoylthioalkyl $C_1$-$C_{12}$, a $C_3$-$C_{18}$ cycloalkanoylthioalkyl $C_1$-$C_{12}$, a $C_1$-$C_{12}$ aroylthioalkyl, a $C_1$-$C_{12}$ heterocyclylthioalkyl, a $C_1$-$C_{12}$ arylthioalkyl, a $C_1$-$C_{12}$ alkanoylaminoalkyl $C_1$-$C_{12}$, a $C_1$-$C_{12}$ haloalkanoylaminoalkyl $C_1$-$C_{12}$, a $C_3$-$C_{18}$ cycloalkanoylaminoalkyl $C_1$-$C_{12}$, a $C_1$-$C_{12}$ aroylaminoalkyl, a $C_1$-$C_{12}$ heterocyclylaminoalkyl;

A represents a direct bond or a $C_1$-$C_{12}$ alkyl;

Y represents an oxygen or sulfur atom;

Z represents an oxygen or sulfur atom;

X represents a halogen atom, a CN group, a $NO_2$ group;

n represents a number ranging from 0 to 3;

G represents a $C_3$-$C_{18}$ cycloalkyl containing from 0 to 3 heteroatoms selected from the group consisting of O, N, S, a $C_3$-$C_{18}$ cycloalkenyl containing from 1 to 3 unsaturations and from 0 to 3 heteroatoms selected from the group consisting of O, N, S, a $C_6$-$C_{20}$ bicycloalkyl containing from 0 to 3 heteroatoms selected from O, N, S, a $C_6$-$C_{20}$ bicycloalkenyl containing from 1 to 3 unsaturations and from 0 to 3 heteroatoms selected from the group consisting of O, N, S, adamantyl, said cyclic groups being optionally substituted with 1 to 3 groups, the same or different, selected from the group consisting of $C_1$-$C_6$ alkyl, $C_3$-$C_{12}$ cycloalkyl, benzyl and with the possibility of incorporating in said cyclic structure one or more groups selected from the group consisting of: C=O, C(=O)O, C(=O)S, C(=S)O, C(=S)S, C(=O)NR$^3$;

with the proviso that if R$^1$ represents a —NR$^4$R$^5$ group wherein R$^4$ is a hydrogen atom and R$^5$ is an aminocarbonyl group, a methylaminocarbonyl group, a dimethylaminocarbonyl group, a formyl, a $C_2$-$C_{13}$ acyl, a $C_2$-$C_{13}$ alkoxycarbonyl, and R$^2$ and R$^3$ represent a hydrogen atom, and Y is an oxygen atom, G cannot be a $C_3$-$C_{12}$ cycloalkyl, a $C_3$-$C_{12}$ cycloalkenyl and a $C_3$-$C_8$ cycloalkyl containing from 0 to 3 heteroatoms selected from O, N, S.

2. The amide according to claim 1, wherein:

R$^1$ represents a $C_1$-$C_6$ alkoxyl, a $C_1$-$C_6$ haloalkoxyl, a $C_3$-$C_{12}$ cycloalkoxyl, a —NR$^4$R$^5$ group;

R$^2$ represents a $C_2$-$C_7$ acyl, a $C_2$-$C_7$ alkanoyloxyalkyl $C_1$-$C_6$, a $C_2$-$C_7$ haloalkanoyloxyalkyl $C_1$-$C_6$, a $C_1$-$C_6$ alkoxy-$C_1$-$C_6$-alkanoyloxyalkyl $C_1$-$C_6$, a $C_1$-$C_6$ haloalkoxy-$C_1$-$C_6$-alkanoyloxyalkyl $C_1$-$C_6$, a $C_3$-$C_{12}$ cycloalkoxy-$C_1$-$C_6$-alkanoyloxyalkyl $C_1$-$C_6$, an aryloxy $C_1$-$C_6$ alkanoyloxyalkyl $C_1$-$C_6$, a benzyloxy $C_1$-$C_6$ alkanoyloxyalkyl $C_1$-$C_6$, a $C_4$-$C_{12}$ cycloalkanoyloxyalkyl $C_1$-$C_6$, a $C_1$-$C_6$ aroyloxyalkyl, a $C_1$-$C_6$ benzoyloxyalkyl, a $C_1$-$C_6$ heterocyclylcarbonyloxyalkyl, a $C_1$-$C_6$ alkyloxyalkyl $C_1$-$C_6$, a $C_1$-$C_6$ haloalkyloxyalkyl $C_1$-$C_6$, a $C_1$-$C_6$ alkoxy-$C_1$-$C_6$-alkyloxyalkyl $C_1$-$C_6$, a $C_1$-$C_6$ haloalkoxy-$C_1$-$C_6$-alkoxyalkyl $C_1$-$C_6$, a $C_3$-$C_{12}$ cycloalkoxy $C_1$-$C_6$-alkyloxyalkyl $C_1$-$C_6$, an aryloxy $C_1$-$C_6$-alkyloxyalkyl $C_1$-$C_6$, a benzyloxy $C_1$-$C_6$-alkyloxyalkyl $C_1$-$C_6$, a $C_3$-$C_{12}$ cycloalkyloxyalkyl $C_1$-$C_6$, a $C_1$-$C_6$ aryloxyalkyl, a $C_1$-$C_6$ benzyloxyalkyl; a $C_1$-$C_6$ heterocyclyloxyalkyl, a $C_4$-$C_6$ alkanoylthioalkyl $C_1$-$C_6$, a $C_2$-$C_6$ haloalkanoylthioalkyl $C_1$-$C_6$, a $C_4$-$C_{12}$ cycloalkanoylthioalkyl $C_1$-$C_6$, a $C_1$-$C_6$ aroylthioalkyl, a $C_1$-$C_6$ benzoylthioalkyl; a $C_1$-$C_6$ heterocyclylcarbonylthioalkyl, a $C_1$-$C_6$ alkylthioalkyl $C_1$-$C_6$, a $C_1$-$C_6$ haloalkylthioalkyl $C_1$-$C_6$, a $C_1$-$C_6$ alkoxy-$C_1$-$C_6$-alkylthioalkyl $C_1$-$C_6$, a $C_1$-$C_6$ haloalkoxy-$C_1$-$C_6$-alkylthioalkyl $C_1$-$C_6$, a $C_3$-$C_{12}$ cycloalkoxy $C_1$-$C_6$ alkylthioalkyl $C_1$-$C_6$, a $C_1$-$C_6$ aryloxy alkylthioalkyl $C_1$-$C_6$, a $C_1$-$C_6$ benzyloxy alkylthioalkyl $C_1$-$C_6$, a $C_3$-$C_{12}$ cycloalkylthioalkyl $C_1$-$C_6$, a $C_1$-$C_6$ benzylthioalkyl, a $C_1$-$C_6$ arylthioalkyl, a $C_1$-$C_6$ heterocyclylthioalkyl, a $C_2$-$C_6$ alkanoylaminoalkyl $C_1$-$C_6$, a $C_2$-$C_6$ haloalkanoylaminoalkyl $C_1$-$C_6$, a $C_4$-$C_{12}$ cycloalkanoylaminoalkyl $C_1$-$C_6$, a $C_1$-$C_6$ aroylaminoalkyl, a $C_1$-$C_6$ benzoylaminoalkyl, a $C_1$-$C_6$ heterocyclylcarbonylaminoalkyl, a $C_1$-$C_6$ heterocyclylaminoalkyl, a $C_4$-$C_{12}$ cycloalkylaminoalkyl $C_1$-$C_6$, a tetrahydropyranyl, a $C_1$-$C_6$ trimethylsilyloxyalkyl, a $C_1$-$C_6$ trimethylsilyl-ethoxyalkyl;

R$^3$ represents a hydrogen atom, a $C_1$-$C_6$ alkyl, a $C_3$-$C_{12}$ cycloalkyl;

R$^4$ and R$^5$, the same or different, represent a hydrogen atom, an aminocarbonyl group, a methylaminocarbonyl group, a dimethylaminocarbonyl group, a $C_1$-$C_6$ alkyl, a formyl, a $C_2$-$C_7$ acyl, a $C_2$-$C_7$ haloalkylcarbonyl, a benzyl group, an aroyl group, a $C_2$-$C_7$ alkoxycarbonyl, a $C_1$-$C_6$ alkoxyalkyl $C_1$-$C_6$; a $C_1$-$C_6$ alkanoyloxyalkyl $C_1$-$C_6$, a $C_1$-$C_6$ haloalkanoyloxyalkyl $C_1$-$C_{12}$, a $C_3$-$C_{12}$ cycloalkanoyloxyalkyl $C_1$-$C_6$, a $C_1$-$C_6$ aroyloxyalkyl, a $C_1$-$C_6$ heterocyclylcarbonyloxyalkyl, a $C_1$-$C_6$ aryloxyalkyl, a $C_1$-$C_6$ heterocyclyloxyalkyl, a $C_1$-$C_6$ alkanoylthioalkyl $C_1$-$C_6$, a $C_1$-$C_6$ haloalkanoylthioalkyl $C_1$-$C_6$, a $C_3$-$C_{12}$ cycloalkanoylthioalkyl $C_1$-$C_6$, a $C_1$-$C_6$ aroylthioalkyl, a $C_1$-$C_6$ heterocyclylthioalkyl, a $C_1$-$C_6$ arylthioalkyl, a $C_1$-$C_6$ alkanoylaminoalkyl $C_1$-$C_6$, a $C_1$-$C_6$ haloalkanoylaminoalkyl $C_1$-$C_6$, a $C_3$-$C_{12}$ cycloalkanoylaminoalkyl $C_1$-$C_6$, a $C_1$-$C_6$ aroylaminoalkyl, a $C_1$-$C_6$ heterocyclylaminoalkyl;

A represents a direct bond or a $C_1$-$C_6$ alkyl;

Y represents an oxygen or sulfur atom;

X represents a halogen atom, a CN group, a NO$_2$ group;

n represents a number ranging from 0 to 1;

G represents a $C_3$-$C_{12}$ cycloalkyl containing from 0 to 3 heteroatoms selected from O, N, S, a $C_3$-$C_{12}$ cycloalkenyl containing from 1 to 3 unsaturations and from 0 to 3 heteroatoms selected from the group consisting of O, N, S, a $C_6$-$C_{16}$ bicycloalkyl containing from 0 to 3 heteroatoms selected from O, N, S, a $C_6$-$C_{16}$ bicycloalkenyl containing from 1 to 3 unsaturations and from 0 to 3 heteroatoms selected from O, N, S, adamantyl, said cyclic groups being optionally substituted with 1 to 3 groups, the same or different, selected from the group consisting of $C_1$-$C_6$ alkyl, $C_3$-$C_{12}$ cycloalkyl, benzyl and with the possibility of incorporating in said cyclic structure one or more groups selected from the group consisting of: C=O, C(=O)O, C(=O)S, C(=S)O, C(=S)S, and C(=O)NR$^3$.

3. The amide according to claim 1, wherein:

R$^2$ represents a $C_2$-$C_6$ acyl, a $C_1$-$C_6$ alkoxy-$C_1$-$C_6$-alkanoyloxyalkyl $C_1$-$C_6$, a $C_1$-$C_6$ haloalkoxy-$C_1$-$C_6$-alkanoyloxyalkyl $C_1$-$C_6$, a $C_3$-$C_{12}$ cycloalkoxy-$C_1$-$C_6$-alkanoyloxyalkyl $C_1$-$C_6$, a $C_3$-$C_{12}$ cycloalkyloxyalkyl $C_1$-$C_6$, a $C_4$-$C_{12}$ alkanoylthioalkyl $C_1$-$C_6$, a $C_2$-$C_6$ haloalkanoylthioalkyl $C_1$-$C_6$, a $C_4$-$C_{12}$ cycloalkanoylthioalkyl $C_1$-$C_6$, a $C_2$-$C_6$ alkanoylaminoalkyl $C_1$-$C_6$, a $C_2$-$C_6$ haloalkanoylaminoalkyl $C_1$-$C_6$, a $C_1$-$C_6$ alkoxy-$C_1$-$C_6$-alkyloxyalkyl $C_1$-$C_6$, a $C_1$-$C_6$ haloalkoxy-$C_1$-$C_6$-alkyloxyalkyl $C_1$-$C_6$, a $C_3$-$C_{12}$ cycloalkoxy $C_1$-$C_6$-alkyloxyalkyl $C_1$-$C_6$, a tetrahydropyranyl, a $C_1$-$C_6$ trimethylsilyloxyalkyl, a $C_1$-$C_6$ trimethylsilyl-ethoxyalkyl;

Y and Z both represent an oxygen atom;

G represents a $C_3$-$C_{12}$ cycloalkyl containing from 0 to 3 heteroatoms selected from O, N, S, a $C_3$-$C_{12}$ cycloalkenyl containing from 1 to 3 unsaturations and from 0 to 3 heteroatoms selected from the group consisting of O, N, S, a $C_6$-$C_{16}$ bicycloalkyl containing from 0 to 3 heteroatoms selected from the group consisting of O, N, S, a $C_6$-$C_{16}$ bicycloalkenyl containing from 1 to 3 unsaturations and from 0 to 3 heteroatoms selected from the group consisting of O, N, S, adamantyl, said cyclic groups being optionally substituted with 1 to 3 groups, the same or different, selected from the group consisting of $C_1$-$C_6$ alkyl, $C_3$-$C_{12}$ cycloalkyl, benzyl and with the possibility of incorporating in said cyclic structure one or more groups selected from the group consisting of: C=O, C(=O)O, C(=O)S, C(=S)O, C(=S)S, and C(=O)NR$^3$.

4. The amide according to claim 1, selected from compounds having general formula (I) wherein R$^1$, R$^2$, R$^3$, Y, Z, X, n, A, G have the meanings indicated in the following table

| Comp. | R¹ | R² | R³ | Y | Z | A | X | n | G |
|---|---|---|---|---|---|---|---|---|---|
| 1. | NHCHO | 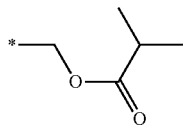 [SMILES: *COC(=O)C(C)C] | H | O | O | — | | 0 | 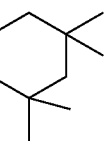 |
| 2. | NHCHO | 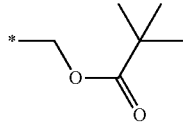 [SMILES: *COC(=O)C(C)(C)C] | H | O | O | — | | 0 | 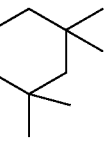 |
| 3. | NHCHO | 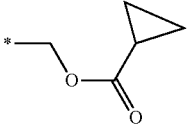 [SMILES: *COC(=O)C1CC1] | H | O | O | — | | 0 | 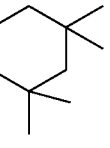 |
| 4. | NR²CHO | 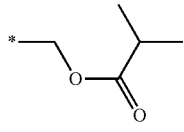 | H | O | O | — | | 0 | 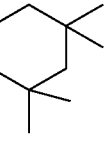 |
| 5. | NR²CHO | 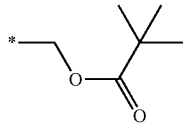 [SMILES: *COC(=O)C(C)(C)C] | H | O | O | — | | 0 | 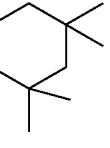 |
| 6. | NR²CHO | 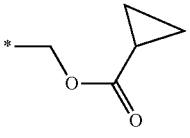 [SMILES: *COC(=O)C1CC1] | H | O | O | — | | 0 |  |
| 7. | NR$_2^2$ | 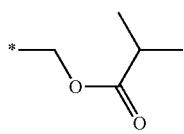 | H | O | O | — | | 0 | 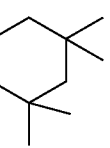 |
| 8. | NR$_2^2$ | 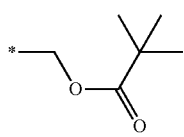 [SMILES: *COC(=O)C(C)(C)C] | H | O | O | — | | 0 | 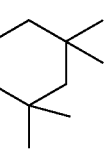 |
| 9. | NR$_2^2$ | 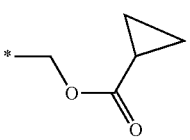 | H | O | O | — | | 0 | 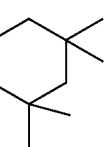 |
| 10. | NHCHO | 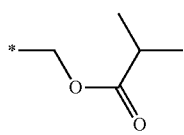 | H | O | O | — | | 0 | 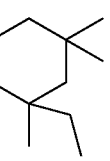 |

-continued

| Comp. | R¹ | R² | R³ | Y | Z | A | X | n | G |
|---|---|---|---|---|---|---|---|---|---|
| 11. | NHCHO | *─\O─C(CH₃)H─C(=O)─ | H | O | O | — | | 0 | cyclododecyl* |
| 12. | NHCHO | *─\O─C(CH₃)H─C(=O)─ | H | O | O | — | | 0 | cyclooctyl* |
| 13. | NHCHO | *─\O─C(CH₃)H─C(=O)─ | H | O | O | — | | 0 | adamantyl* |
| 14. | NHCHO | *─\O─C(CH₃)H─C(=O)─ | H | O | O | — | | 0 | (macrocyclic ketone group)* |
| 15. | NHCHO | *─\O─C(CH₃)H─C(=O)─ | H | O | O | — | | 0 | (macrocyclic trimethyl diene)* |
| 16. | NHCHO | *─\O─C(CH₃)H─C(=O)─ | H | O | O | — | | 0 | 3,3,5-trimethylcyclohexyl* |
| 17. | NHCHO | *─\O─C(CH₃)H─C(=O)─ | H | O | O | — | | 0 | menthyl* |
| 18. | NHCHO | *─\O─C(CH₃)H─C(=O)─ | H | O | O | — | | 0 | pinanyl* |
| 19. | NHCHO | *─\O─C(CH₃)H─C(=O)─ | H | O | O | — | | 0 | 4-tert-butylcyclohexyl* |

-continued

| Comp. | R¹ | R² | R³ | Y | Z | A | X | n | G |
|---|---|---|---|---|---|---|---|---|---|
| 20. | NHCHO | *−CH₂−O−C(=O)−CH(CH₃)− | CH₃ | O | O | — |  | 0 | 3-ethyl-3,5,5-trimethylcyclohexyl |
| 21. | NHCHO | *−CH₂−O−C(=O)−CH(CH₃)− | CH₃ | O | O | — |  | 0 | cyclododecyl |
| 22. | NHCHO | *−CH₂−O−C(=O)−CH(CH₃)− | CH₃ | O | O | — |  | 0 | 2-adamantyl |
| 23. | NHCHO | *−CH₂−O−C(=O)−CH(CH₃)− | H | S | O | — |  | 0 | 2-adamantyl |
| 24. | OCH₃ | *−CH₂−O−C(=O)−CH(CH₃)− | H | S | O | — |  | 0 | 3-ethyl-3,5,5-trimethylcyclohexyl |
| 25. | NHCHO | *−CH₂−S−C(=O)−CH(CH₃)− | H | S | O | — |  | 0 | 3-ethyl-3,5,5-trimethylcyclohexyl |
| 26. | NHCHO | *−CH₂−NH−C(=O)−CH₃ | H | O | O | — |  | 0 | 3-ethyl-3,5,5-trimethylcyclohexyl |
| 27. | NHCHO | *−CH₂−O−cyclopropyl | H | O | O | — |  | 0 | 3-ethyl-3,5,5-trimethylcyclohexyl |
| 28. | NHCHO | *−CH₂−O−Si(CH₃)₃ | H | O | O | — |  | 0 | 3-ethyl-3,5,5-trimethylcyclohexyl |

-continued
| Comp. | R¹ | R² | R³ | Y | Z | A | X | n | G |
|---|---|---|---|---|---|---|---|---|---|
| 29. | NHCHO | 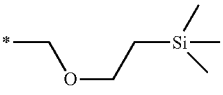 | H | O | O | — | | 0 | 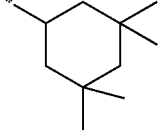 |
| 30. | NHCHO | 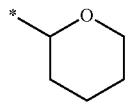 | H | O | O | — | | 0 | 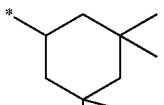 |
| 31. | NHCHO | 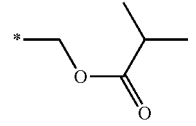 | H | O | O | CH₂ | | 0 | 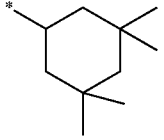 [SMILES: *C1CC(C)(C)CC(C)(C)C1] |
| 32. | NHCHO | 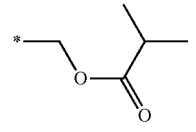 | H | O | O | CH₂ | | 0 | 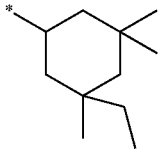 [SMILES: *C1CC(C)(C)CC(C)(CC)C1] |
| 33. | OCH₃ | 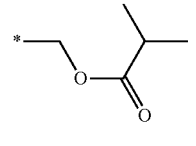 | H | O | O | — | 5-Cl | 1 | 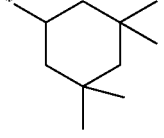 |
| 34. | OCH₃ | 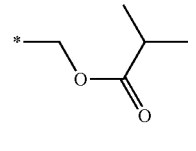 [SMILES: *COC(=O)C(C)C] | H | O | O | — | 6-Br | 1 | 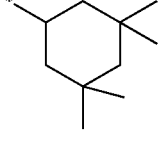 |
| 35. | OCH₃ | 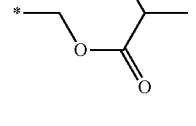 | H | O | O | — | 4-NO₂ | 1 | 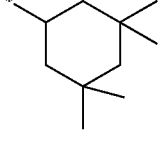 |
| 36. | NHCHO | 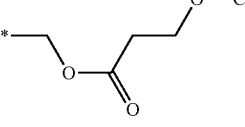 | H | O | O | CH₂ | | 0 | 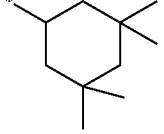 |
| 37. | NHCHO | 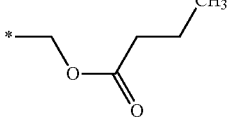 | H | O | O | CH₂ | | 0 | 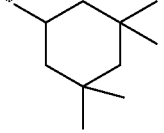 |
| 38. | NHCHO | 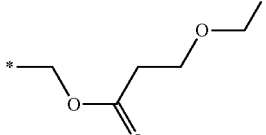 | H | O | O | CH₂ | | 0 | 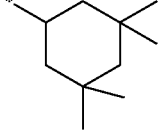 |

-continued
| Comp. | R¹ | R² | R³ | Y | Z | A | X | n | G |
|---|---|---|---|---|---|---|---|---|---|
| 39. | NHCHO | 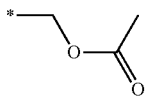 | H | O | O | — | | 0 | 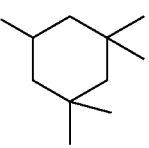 |
| 40. | NHCHO | 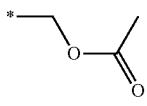 | H | O | O | — | | 0 | 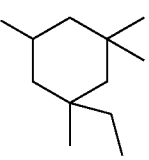 |
| 41. | NHCHO | 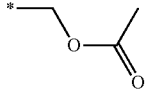 | H | S | O | | | 0 | 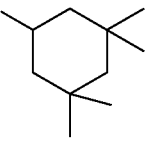 |
| 42. | NHCHO | 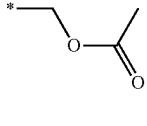 | H | S | O | — | | 0 | 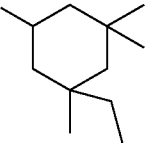 |
| 43. | NHCHO | 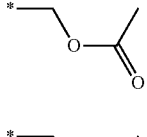 | H | O | O | — | | 0 | 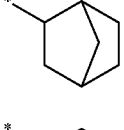 |
| 44. | NHCHO | 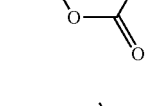 | H | S | O | — | | 0 | 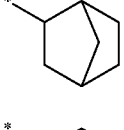 |
| 45. | NHCHO | 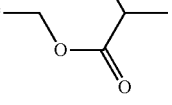 | H | O | O | — | | 0 | 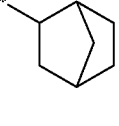 |
| 46. | NHCHO | 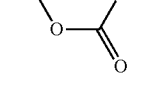 | H | O | O | — | | 0 | 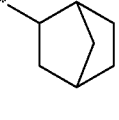 |
| 47. | NHCHO | 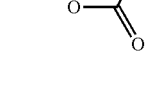 | H | O | O | — | | 0 | 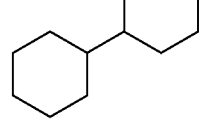 |
| 48. | NHCHO | 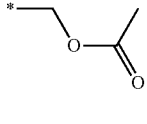 | H | S | O | — | | 0 | 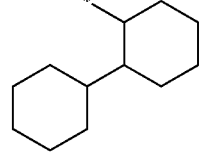 |

-continued

| Comp. | R¹ | R² | R³ | Y | Z | A | X | n | G |
|---|---|---|---|---|---|---|---|---|---|
| 49. | NHCHO | *-CH₂-O-C(=O)-CH(CH₃)₂ | H | O | O | — |  | 0 | *-cyclohexyl-cyclohexyl |
| 50. | NHCHO | *-CH₂-O-C(=O)-O-CH₃ | H | O | O | — |  | 0 | *-cyclohexyl-cyclohexyl |
| 52. | NHCHO | COCH₃ | H | O | O | — |  | 0 | *-cyclohexyl-cyclohexyl |
| 53. | NHCHO | *-CH₂-O-C(=O)-O-CH₃ | H | O | O | — |  | 0 | *-3,3,5,5-tetramethylcyclohexyl |
| 54. | NHCHO | *-CH₂-O-C(=O)-O-CH₃ | H | O | O | — |  | 0 | *-3,3,5-trimethyl-5-ethylcyclohexyl |
| 55. | NHCHO | *-CH₂-O-C(=O)-O-CH₃ | H | O | O | — |  | 0 | *-cycloheptyl with ethyl/methyl |
| 56. | NHCHO | *-CH₂-O-C(=O)-O-CH₃ | H | O | O | — |  | 0 | *-tetramethylcyclohexyl |
| 57. | NHCHO | *-CH₂-O-C(=O)-CH₃ | H | O | O | — |  | 0 | *-tetramethylcyclohexyl |
| 58. | NHCHO | *-CH₂-O-C(=O)-CH(CH₃)₂ | H | O | O | — |  | 0 | *-tetramethylcyclohexyl |

-continued
| Comp. | R¹ | R² | R³ | Y | Z | A | X | n | G |
|---|---|---|---|---|---|---|---|---|---|
| 59. | NHCHO | 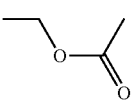 | H | O | O | — | | 0 | 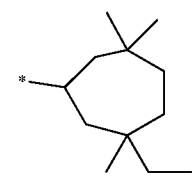 [SMILES: *C1CC(C)(C)CCC(C)(CC)C1] |
| 60. | NHCHO | 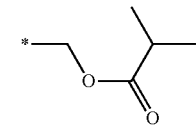 [SMILES: *COC(=O)C(C)C] | H | O | O | — | | 0 | 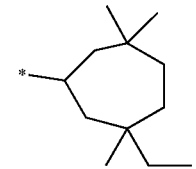 [SMILES: *C1CC(C)(C)CCC(C)(CC)C1] |
| 61. | NHCHO | 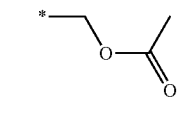 | H | O | O | — | | 0 | 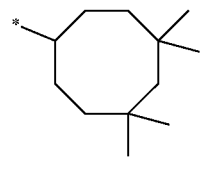 [SMILES: *C1CCC(C)(C)CC(C)(C)CC1] |
| 62. | NHCHO | 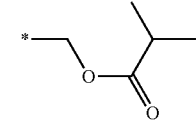 [SMILES: *COC(=O)C(C)C] | H | O | O | — | | 0 | 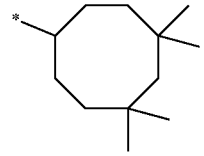 [SMILES: *C1CCC(C)(C)CC(C)(C)CC1] |
| 63. | NHCHO | 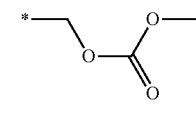 [SMILES: *COC(=O)OC] | H | O | O | — | | 0 | 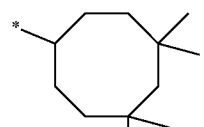 |
| 64. | NHCHO | 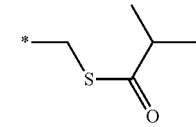 [SMILES: *CSC(=O)C(C)C] | H | S | O | — | | 0 | 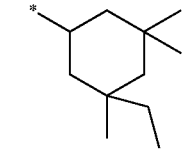 [SMILES: *C1CC(C)(C)CC(C)(CC)C1] |
| 65. | NHCHO | 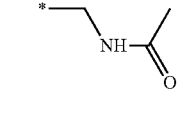 | H | O | O | — | | 0 | 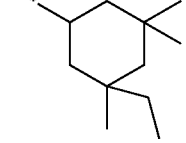 |
| 66. | NHCHO | 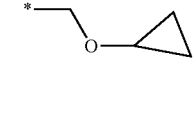 | H | O | O | — | | 0 | 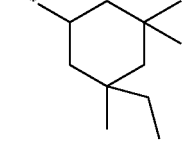 |
| 67. | NHCHO | 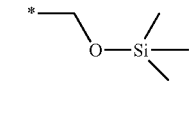 | H | O | O | — | | 0 | 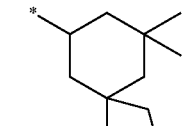 |

-continued

| Comp. | R¹ | R² | R³ | Y | Z | A | X | n | G |
|---|---|---|---|---|---|---|---|---|---|
| 68. | NHCHO | *−CH₂−O−CH₂CH₂−Si(CH₃)₃ | H | O | O | — |  | 0 | 3,3,5-trimethyl-5-ethylcyclohexyl* |
| 69. | NHCHO | *-(tetrahydropyran-2-yl) | H | O | O | — |  | 0 | 3,3,5-trimethyl-5-ethylcyclohexyl* |
| 70. | NHCHO | *−CH₂−O−C(=O)−CH₃ | H | O | O | CH₂ |  | 0 | 3,3,5-trimethyl-5-ethylcyclohexyl* |
| 72. | NHCHO | COCH₃ | H | O | O | — |  | 0 | dilactone ring* |
| 73. | NHCHO | *−CH₂−O−C(=O)−CH₃ | H | O | O | — |  | 0 | dilactone ring* |
| 74. | NHCHO | *−CH₂−O−C(=O)−O−CH₃ | H | O | O | — |  | 0 | dilactone ring* |
| 75. | NHCHO | *−CH₂−O−C(=O)−CH(CH₃)₂ | H | O | O | — |  | 0 | dilactone ring* |
| 77. | NHCHO | COCH₃ | H | O | O | — |  | 0 | lactone-thiolactone ring* |

-continued

| Comp. | R¹ | R² | R³ | Y | Z | A | X | n | G |
|---|---|---|---|---|---|---|---|---|---|
| 78. | NHCHO | *−CH₂−O−C(=O)−CH₃ | H | O | O | — | | 0 | (macrocycle with lactone and thioester) |
| 79. | NHCHO | *−CH₂−O−C(=O)−O−CH₃ | H | O | O | — | | 0 | (macrocycle with lactone and thioester) |
| 80. | NHCHO | *−CH₂−O−C(=O)−CH(CH₃)₂ | H | O | O | — | | 0 | (macrocycle with lactone and thioester) |
| 82. | NHCHO | COCH₃ | H | O | O | — | | 0 | (macrocycle with lactone and thioether) |
| 83. | NHCHO | *−CH₂−O−C(=O)−CH₃ | H | O | O | — | | 0 | (macrocycle with lactone and thioether) |
| 84. | NHCHO | *−CH₂−O−C(=O)−O−CH₃ | H | O | O | — | | 0 | (macrocycle with lactone and thioether) |
| 85. | NHCHO | *−CH₂−O−C(=O)−CH(CH₃)₂ | H | O | O | — | | 0 | (macrocycle with lactone and thioether) |
| 87. | NHCHO | *−CH₂−O−C(=O)−CH(CH₃)₂ | H | O | O | — | | 0 | (macrocycle with lactone and gem-dimethyl amide) |

-continued
| Comp. | R¹ | R² | R³ | Y | Z | A | X | n | G |
|---|---|---|---|---|---|---|---|---|---|
| 88. | NHCHO | COCH₃ | H | O | O | — | | 0 | 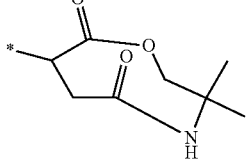 |
| 89. | NHCHO | 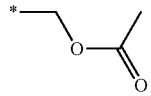 | H | O | O | — | | 0 | 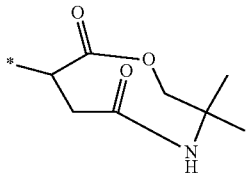 |
| 90. | NHCHO | 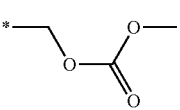 | H | O | O | — | | 0 | 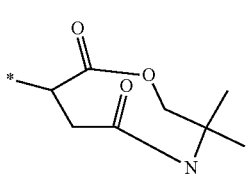 |
| 91. | NHCHO | 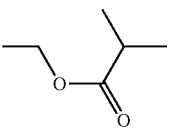 | H | O | S | — | | 0 | 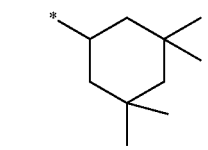 |
| 92. | NHCHO | 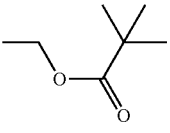 | H | O | S | — | | 0 | 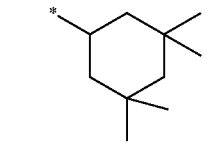 |
| 93. | NHCHO | 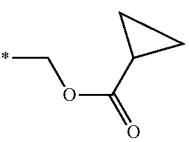 | H | O | S | — | | 0 | 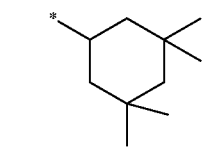 |
| 94. | NHCHO | 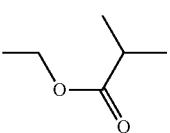 | H | O | S | — | | 0 | 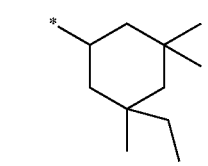 [SMILES: *C1CC(C)(C)CC(C)(CC)C1] |
| 95. | NHCHO | 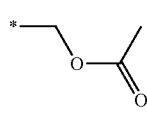 [SMILES: *COC(C)=O] | H | O | S | — | | 0 | 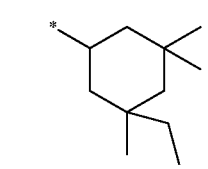 |
| 96. | NHCHO | 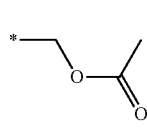 [SMILES: *COC(C)=O] | H | O | S | — | | 0 | 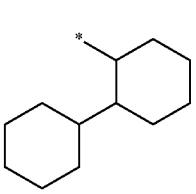 [SMILES: *C1CCCCC1C1CCCCC1] |

-continued
| Comp. | R¹ | R² | R³ | Y | Z | A | X | n | G |
|---|---|---|---|---|---|---|---|---|---|
| 97. | NHCHO | 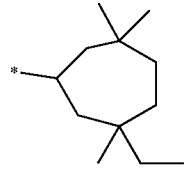 [SMILES: *C1CC(C)(C)CCC(C)(CC)C1] | H | O | S | — |  | 0 | 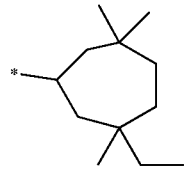 [SMILES: *C1CC(C)(C)CCC(C)(CC)C1] |
| 98. | NHCHO | 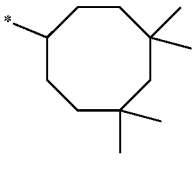 | H | O | S | — |  | 0 | 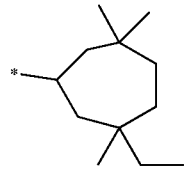 [SMILES: *C1CC(C)(C)CCC(C)(CC)C1] |
| 99. | NHCHO | 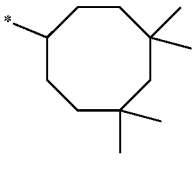 | H | O | S | — |  | 0 | 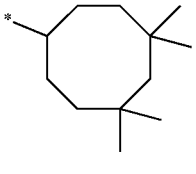 [SMILES: *C1CCC(C)(C)CC(C)(C)CC1] |
| 100. | NHCHO | 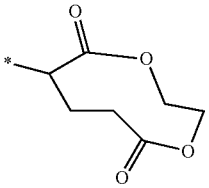 | H | O | S | — |  | 0 | 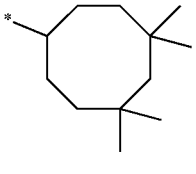 [SMILES: *C1CCC(C)(C)CC(C)(C)CC1] |
| 101. | NHCHO | COCH₃ | H | O | S | — |  | 0 | 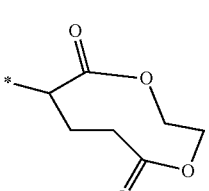 |
| 102. | NHCHO | 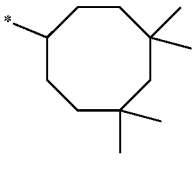 | H | O | S | — |  | 0 | 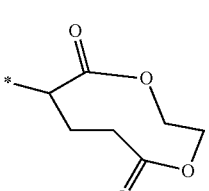 |
| 103. | NHCHO | COCH₃ | H | O | S | — |  | 0 | 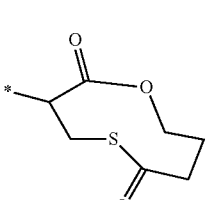 |
| 104. | NHCHO | 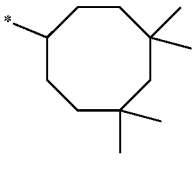 | H | O | S | — |  | 0 | 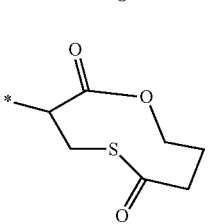 |

-continued

| Comp. | R¹ | R² | R³ | Y | Z | A | X | n | G |
|---|---|---|---|---|---|---|---|---|---|
| 105. | NHCHO | *—CH₂—O—C(=O)—CH(CH₃)₂ | H | O | S | — | | 0 | (lactone/morpholinone structure) |
| 106. | NHCHO | COCH₃ | H | O | S | — | | 0 | (3,3,5-trimethyl-5-ethylcyclohexyl) |
| 107. | NHCHO | COCH₃ | H | O | S | — | | 0 | (3,3,5,5-tetramethylcyclohexyl) |

5. The amide according to claim 1, selected from compounds having general formula (I) wherein $R^1$, $R^2$, $R^3$, Y, Z, X, n, A, G have the meanings indicated in the following table

| Comp. | R¹ | R² | R³ | Y | Z | A | X | n | G |
|---|---|---|---|---|---|---|---|---|---|
| 1. | NHCHO | *—CH₂—O—C(=O)—CH(CH₃)₂ | H | O | O | — | | 0 | (3,3,5,5-tetramethylcyclohexyl) |
| 2. | NHCHO | *—CH₂—O—C(=O)—C(CH₃)₃ | H | O | O | — | | 0 | (3,3,5,5-tetramethylcyclohexyl) |
| 4. | NR²CHO | *—CH₂—O—C(=O)—CH(CH₃)₂ | H | O | O | — | | 0 | (3,3,5,5-tetramethylcyclohexyl) |
| 10. | NHCHO | *—CH₂—O—C(=O)—CH(CH₃)₂ | H | O | O | — | | 0 | (3,3,5-trimethyl-5-ethylcyclohexyl) |
| 106. | NHCHO | COCH₃ | H | O | S | — | | 0 | (3,3,5-trimethyl-5-ethylcyclohexyl) |

-continued

| Comp. | R¹ | R² | R³ | Y | Z | A | X | n | G |
|---|---|---|---|---|---|---|---|---|---|
| 107. | NHCHO | COCH₃ | | H | O | S | — | 0 | *-(3,3,5,5-tetramethylcyclohexyl) |

6. The amide according to claim 1, which are a) geometric isomers of the compounds having general formula (I); b) in the form of salts of the compounds having formula (I) obtained by the addition of inorganic or organic acids; c) hydrated forms of the compounds having formula (I).

7. A fungicidal composition comprising at least one compound having formula (I) according to claim 1, a solvent and/or solid or liquid diluent, and optionally a surfactant.

8. The composition according to claim 7, comprising one or more further active ingredients selected from the group consisting of fungicides other than those having general formula (I), phytoregulators, antibiotics, herbicides, insecticides, fertilizers and/or mixtures thereof, preferably comprising at least one other fungicide.

9. The composition according to claim 8, consisting of a compound having formula (I) and a further fungicide, selected from the group consisting of:
C1: compound 1+tetraconazole;
C2: compound 1+tebuconazole;
C3: compound 1+epoxyconazole;
C4: compound 1+prothioconazole;
C5: compound 1+difenoconazole;
C6: compound 1+penconazole;
C7: compound 1+prochloraz;
C8: compound 1+fenpropimorph;
C9: compound 1+spiroxamine;
C10: compound 1+bixafen;
C11: compound 1+boscalid;
C12: compound 1+carboxin;
C13: compound 1+fluopyram;
C14: compound 1+fluxapyroxad;
C15: compound 1+isopyrazam;
C16: compound 1+penthiopyrad;
C17: compound 1+sedaxane;
C18: compound 1+azoxystrobin;
C19: compound 1+dimoxystrobin;
C20: compound 1+fluoxastrobin;
C21: compound 1+kresoxim-methyl;
C22 compound 1+picoxystrobin;
C23: compound 1+pyraclostrobin;
C24: compound 1+trifloxystrobin;
C25: compound 1+metrafenone;
C26: compound 1+proquinazid;
C27: compound 1+mepanipyrim;
C28: compound 1+cyprodinil;
C29: compound 1+iprodione;
C30: compound 1+procymidone;
C31: compound 1+carbendazim;
C32: compound 1+thiophanate-methyl;
C33: compound 1+fluindapyr;
C34: compound 1+benalaxyl-M;
C35: compound 1+fenpyrazamine;
C36: compound 1+fluazinam;
C37: compound 1+tolclofos-methyl;
C38: compound 1+mandipropamid;
C39: compound 1+copper oxychloride;
C40: compound 1+copper salicylate;
C41: compound 1+chlorothalonil;
C42: compound 1+cimoxanil;
C43: compound 1+dimetomorph;
C44: compound 1+oxathiapiprolin;
C45: compound 1+fluopicolide;
C46: compound 2+tetraconazole;
C47: compound 2+tebuconazole;
C48: compound 2+epoxyconazole;
C49: compound 2+prothioconazole;
C50: compound 2+difenoconazole;
C51: compound 2+penconazole;
C52: compound 2+prochloraz;
C53: compound 2+fenpropimorph;
C54: compound 2+spiroxamine;
C55: compound 2+bixafen;
C56: compound 2+boscalid;
C57: compound 2+carboxin;
C58: compound 2+fluopyram;
C59: compound 2+fluxapyroxad;
C60: compound 2+isopyrazam;
C61: compound 2+penthiopyrad;
C62: compound 2+sedaxane;
C63: compound 2+azoxystrobin;
C64: compound 2+dimoxystrobin;
C65: compound 2+fluoxastrobin;
C66: compound 2+kresoxim-methyl;
C67: compound 2+picoxystrobin;
C68: compound 2+pyraclostrobin;
C69: compound 2+trifloxystrobin;
C70: compound 2+metrafenone;
C71: compound 2+proquinazid;
C72: compound 2+mepanipyrim;
C73: compound 2+cyprodinil;
C74: compound 2+iprodione;
C75: compound 2+procymidone;
C76: compound 2+carbendazim;
C77: compound 2+thiophanate-methyl;
C78: compound 2+fluindapyr;
C79: compound 2+benalaxyl-M;
C80: compound 2+fenpyrazamine;
C81: compound 2+fluazinam;
C82: compound 2+tolclofos-methyl;
C83: compound 2+mandipropamid;
C84: compound 2+copper oxychloride;
C85: compound 2+copper salicylate;
C86: compound 2+chlorothalonil;
C87: compound 2+cimoxanil;
C88: compound 2+dimetomorph;
C89: compound 2+oxathiopiproline;
C90: compound 2+fluopicolide;
C91: compound 4+tetraconazole;
C92: compound 4+tebuconazole;
C93: compound 4+epoxyconazole;

C94: compound 4+prothioconazole;
C95: compound 4+difenconazole;
C96: compound 4+penconazole;
C97: compound 4+prochloraz;
C98: compound 4+fenpropimorph;
C99: compound 4+spiroxamine;
C100: compound 4+bixafen;
C101: compound 4+boscalid;
C102: compound 4+carboxin;
C103: compound 4+fluopyram;
C104: compound 4+fluxapyroxad;
C105: compound 4+isopyrazam;
C106: compound 4+penthiopyrad;
C107: compound 4+sedaxane;
C108: compound 4+azoxystrobin;
C109: compound 4+dimoxystrobin;
C110: compound 4+fluoxastrobin;
C111: compound 4+kresoxim-methyl;
C112: compound 4+picoxystrobin;
C113: compound 4+pyraclostrobin;
C114: compound 4+trifloxystrobin;
C115: compound 4+metrafenone;
C116: compound 4+proquinazid;
C117: compound 4+mepanipyrim;
C118: compound 4+cyprodinil;
C119: compound 4+iprodione;
C120: compound 4+procymidone;
C121: compound 4+carbendazim;
C122: compound 4+thiophanate-methyl;
C123: compound 4+fluindapyr;
C124: compound 4+benalaxyl-M;
C125: compound 4+fenpyrazamine;
C125: compound 4+fluazinam;
C126: compound 4+tolclofos-methyl;
C127: compound 4+mandipropamid;
C128: compound 4+copper oxychloride;
C129: compound 4+copper salicylate;
C130: compound 4+chlorothalonil;
C131: compound 4+cimoxanil;
C132: compound 4+dimetomorph;
C133: compound 4+oxathiopiproline;
C134: compound 4+fluopicolide;
C135: compound 1+pyrachlostrobin;
C136: compound 1+zoxamide;
C137: compound 1+ametoctradin;
C138: compound 1+metiram;
C139: compound 1+potassium phosphite;
C140: compound 1+tetraconazole+azoxystrobin,
C141: compound 1+pyraclostrobin+tetraconazole;
C142: compound 1+epoxyconazole+azoxystrobin;
C143: compound 1+pyraclostrobin+epoxyconazole;
C144: compound 1+azoxystrobin+fluindapyr;
C145: compound 1+pyraclostrobin+fluindapyr;
C146: compound 1+fosetyl-aluminium+copper oxychloride;
C147: compound 1+fosetyl-aluminium+copper salicylate;
C148: compound 1+fluindapyr+tetraconazole;
C149: compound 4+tetraconazole+azoxystrobin;
C150: compound 4+pyraclostrobin+tetraconazole;
C151: compound 4+azoxystrobin+fluindapyr;
C152: compound 4+fluindapyr+tetraconazole,
C153: compound 10+tetraconazole;
C154: compound 10+tebuconazole;
C155: compound 10+epoxyconazole;
C156: compound 10 prothioconazole;
C157: compound 10+difenoconazole;
C158: compound 10+penconazole;
C159: compound 10+prochloraz;
C160: compound 10+fenpropimorph;
C161: compound 10+spiroxamine;
C162: compound 10+bixafen;
C163: compound 10+boscalid;
C164: compound 10+carboxin;
C165: compound 10+fluopyram;
C166 compound 10+fluxapyroxad;
C167: compound 10+isopyrazam;
C168 compound 10+penthiopyrad;
C169 compound 10+sedaxane;
C170: compound 10+azoxystrobin;
C171: compound 10+dimoxystrobin;
C172: compound 10+fluoxastrobin;
C173: compound 10+kresoxim-methyl;
C174: compound 10+picoxystrobin;
C175: compound 10+pyraclostrobin;
C176: compound 10+trifloxystrobin;
C177: compound 10+metrafenone;
C178: compound 10+proquinazid;
C179: compound 10+mepanipyrim;
C180: compound 10+cyprodinil;
C181: compound 10+iprodione;
C182: compound 10+procymidone;
C183: compound 10+carbendazim;
C184: compound 10+thiophanate-methyl;
C185: compound 10+fluindapyr;
C186: compound 10+benalaxyl-M;
C187: compound 10+fenpyrazamine;
C188: compound 10+fluazinam;
C189: compound 10+tolclofos-methyl;
C190: compound 10+mandipropamid;
C191: compound 10+copper oxychloride;
C192: compound 10+copper salicylate;
C193: compound 10+chlorothalonil;
C194: compound 10+cimoxanil;
C195: compound 10+dimetomorph;
C196: compound 10+oxathiopiproline;
C197: compound 10+fluopicolide;
C198: compound 106+tetraconazole;
C199: compound 106+tebuconazole;
C200: compound 106+epoxyconazole;
C201: compound 106+prothioconazole;
C202: compound 106+difenoconazole;
C203: compound 106+penconazole;
C204: compound 106+prochloraz;
C205: compound 106+fenpropimorph;
C206: compound 106+spiroxamine;
C208: compound 106+bixafen;
C209: compound 106+boscalid;
C210: compound 106+carboxin;
C211: compound 106+fluopyram;
C212: compound 106+fluxapyroxad;
C213 compound 106+isopyrazam;
C214: compound 106+penthiopyrad;
C215: compound 106+sedaxane;
C216: compound 106+azoxystrobin;
C217: compound 106+dimoxystrobin;
C218: compound 106+fluoxastrobin;
C219: compound 106+kresoxim-methyl;
C220: compound 106+picoxystrobin;
C221: compound 106+pyraclostrobin;
C222: compound 106+trifloxystrobin;
C223: compound 106+metrafenone;
C224: compound 106+proquinazid;
C225: compound 106+mepanipyrim;

C226: compound 106+cyprodinil;
C227: compound 106+iprodione;
C228: compound 106+procymidone;
C229: compound 106+carbendazim;
C230: compound 106+thiophanate-methyl;
C231: compound 106+fluindapyr;
C232: compound 106+benalaxyl-M;
C233: compound 106+fenpyrazamine;
C234: compound 106+fluazinam;
C235: compound 106+tolclofos-methyl;
C236: compound 106+mandipropamid;
C237: compound 106+copper oxychloride;
C238: compound 106+copper salicylate;
C239: compound 106+chlorothalonil;
C240: compound 106+cimoxanil;
C241: compound 106+dimetomorph;
C242: compound 106+oxathiopiproline;
C243: compound 106+fluopicolide;
C244: compound 107+tetraconazole;
C245: compound 107+tebuconazole;
C246: compound 107+epoxyconazole;
C247: compound 107+prothioconazole;
C248: compound 107+difenoconazole;
C249: compound 107+penconazole;
C250: compound 107+prochloraz;
0251: compound 107+fenpropimorph;
C252: compound 107+spiroxamine;
C253: compound 107+bixafen;
C254: compound 107+boscalid;
C255: compound 107+carboxin;
C256: compound 107+fluopyram;
C257: compound 107+fluxapyroxad;
C258: compound 107+isopyrazam;
C259: compound 107+penthiopyrad;
C260: compound 107+sedaxane;
C261: compound 107+azoxystrobin;
C262: compound 107+dimoxystrobin;
C263: compound 107+fluoxastrobin;
C264: compound 107+kresoxim-methyl;
C265: compound 107+picoxystrobin;
C266: compound 107+pyraclostrobin;
C267: compound 107+trifloxystrobin;
C268: compound 107+metrafenone;
C269: compound 107+proquinazid;
C270: compound 107+mepanipyrim;
C271: compound 107+cyprodinil;
C272: compound 107+iprodione;
C273: compound 107+procymidone;
C274: compound 107+carbendazim;
C275: compound 107+thiophanate-methyl;
C276: compound 107+fluindapyr;
C277: compound 107+benalaxyl-M;
C278: compound 107+fenpyrazamine;
C279: compound 107+fluazinam;
C280: compound 107+tolclofos-methyl;
C281: compound 107+mandipropamid;
C282: compound 107+copper oxychloride;
C283: compound 107+copper salicylate;
C284: compound 107+chlorothalonil;
C285: compound 107+cimoxanil;
C286: compound 107+dimetomorph;
C287: compound 107+oxathiopiproline;
C288: compound 107+fluopicolil;
C289: compound 10+tetraconazole+azoxystrobin,
C290: compound 10+pyraclostrobin+tetraconazole;
C291: compound 10+epoxyconazole+azoxystrobin;
C292: compound 10+pyraclostrobin+epoxyconazole;
C293: compound 10+azoxystrobin+fluindapyr;
C294: compound 10+pyraclostrobin+fluindapyr;
C295: compound 10+fosetyl-aluminium+copper oxychloride;
C296: compound 10+fosetyl-aluminium+copper salicylate;
C297: compound 10+fluindapyr+tetraconazole;
C298: compound 106+tetraconazole+azoxystrobin,
C299: compound 106+pyraclostrobin+tetraconazole;
C300: compound 106+epoxyconazole+azoxystrobin;
C301: compound 106+pyraclostrobin+epoxyconazole;
C302: compound 106+azoxystrobin+fluindapyr;
C303: compound 106+pyraclostrobin+fluindapyr;
C304: compound 106+fosetyl-aluminium+copper oxychloride;
C305: compound 106+fosetyl-aluminium+copper salicylate;
C306: compound 106+fluindapyr+tetraconazole;
C307: compound 107+tetraconazole+azoxystrobin,
C308: compound 107+pyraclostrobin+tetraconazole;
C309: compound 107+epoxyconazole+azoxystrobin;
C310: compound 107+pyraclostrobin+epoxyconazole;
C311: compound 107+azoxystrobin+fluindapyr;
C312: compound 107+pyraclostrobin+fluindapyr;
C313: compound 107+fosetyl-aluminium+copper oxychloride;
C314: compound 107+fosetyl-aluminium+copper salicylate;
C315: compound 107+fluindapyr+tetraconazole;
wherein compounds 1, 2, 4, 10, 106, 107 are compounds having general formula (I) wherein the substituents have the meanings defined hereunder:

| Comp. | $R^1$ | $R^2$ | $R^3$ | Y | Z | X | n | A | G |
|---|---|---|---|---|---|---|---|---|---|
| 1. | NHCHO | *-CH₂-O-C(=O)-CH(CH₃)₂ | H | O | O | — | 0 | — | 3,5,5-trimethylcyclohexyl |
| 2. | NHCHO | *-CH₂-O-C(=O)-C(CH₃)₃ | H | O | O | — | 0 | — | 3,5,5-trimethylcyclohexyl |

-continued

| Comp. | R¹ | R² | R³ | Y | Z | X | n | A | G |
|---|---|---|---|---|---|---|---|---|---|
| 4. | NR²CHO | *—CH₂—O—C(=O)—CH(CH₃)₂ | H | O | O | — | 0 | — | 3,3,5-trimethylcyclohexyl |
| 10. | NHCHO | *—CH₂—O—C(=O)—CH(CH₃)₂ | H | O | O | — | 0 | — | 3,3,5-trimethylcyclohexyl |
| 106. | NHCHO | COCH₃ | H | O | S | — | 0 | — | 3,3,5-trimethylcyclohexyl |
| 107. | NHCHO | COCH₃ | H | O | S | — | 0 | — | 3-ethyl-3,5-dimethylcyclohexyl |

10. A method of controlling phytopathogenic fungi in agricultural crops, both curative and preventive, and for the control of phytopathogenic bacteria and viruses, comprising applying an amide according to claim 1.

11. The method according to claim 10, for the control of *Plasmopara viticola* on vines, *Phytophtora infestans* and *Botrytis cinerea* on tomatoes, *Puccinia recondita, Erisiphae graminis, Helminthosporium teres, Septoria nodorum, Septoria tritici* and *Fusarium* spp. on cereals, for the control of *Phakopsora pachyrhizi* on soybeans, for the control of *Uromyces appendiculatus* on beans, for the control of *Venturia inaequalis* on apple trees, for the control of *Sphaerotheca fuliginea* on cucumbers; for the control of *Xanthomonas* spp., *Pseudomonas* spp., *Erwinia amylovora*.

12. A method for controlling phytopathogenic fungi in agricultural crops, both curative and preventive or eradicative, for the control of fungi of the soil and for the control of phytopathogenic bacteria and viruses, comprising applying a fungicidal composition according to claim 7.

13. The method according to claim 12, for the control of *Plasmopara viticola* on vines, *Phytophtora infestans* and *Botrytis cinerea* on tomatoes, *Phytophtora infestans* on potatoes, *Puccinia Recondita, Erysiphe graminis, Helminthosporium teres, Septoria* spp and *Fusarium* spp. on cereals, for the control of *Phakopsora Pachyrhizi* on soybeans, for the control of *Uromyces appendiculatus* on beans, for the control of *Venturia inaequalis* on apple trees, for the control of *Sphaerotheca fuliginea* on cucumbers, for the control of *Rhizoctonia solani, Sclerotinia* spp, *Pythium ultimum* on horticultural plants, for the control of *Xanthomonas* spp., *Pseudomonas* spp., *Erwinia amylovora*.

14. A method for controlling phytopathogenic fungi in agricultural crops, which consists in applying, on any part of the plants to be protected or on the ground, effective and non-phytotoxic doses of compounds having formula (I) according to claim 1.

15. A process for preparing a compound having formula (I) according to claim 1, according to the following reaction scheme:

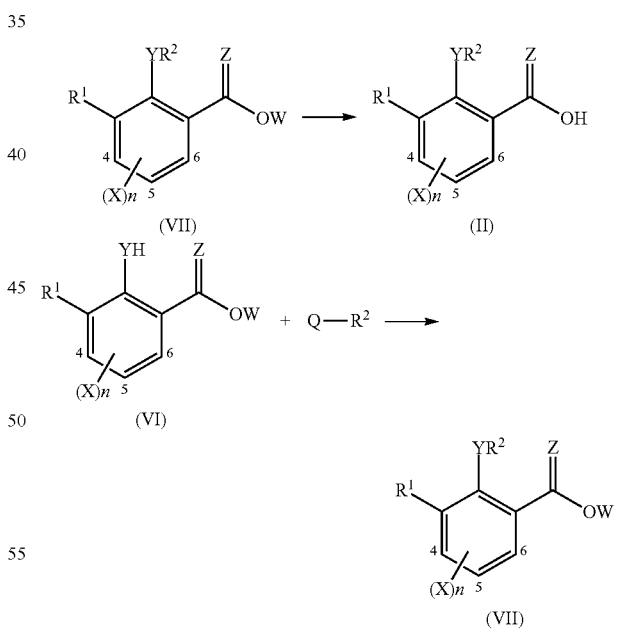

wherein a compound having formula (VII) is obtained by the reaction of a compound R²-Q with a mixture of a compound having formula (VI) dissolved in a solvent selected from the group consisting of ethyl acetate, N,N-dimethylformamide and acetone, at a temperature ranging from −15° C. to 0° C., in the presence of an organic or inorganic base, selected from the group consisting of potassium carbonate, sodium carbonate, sodium hydride, triethylamine and pyridine, optionally in the presence of a catalyst selected from the group consisting of sodium iodide, potassium iodide and a crown ether, such as 15-crown-5 or 18-crown-6, wherein, in the compound $R^2$-Q, Q represents an outgoing group selected from the group consisting of a halogen, or a mesylate and a triflate, the other substituents having the meanings previously indicated.

16. The process for preparing a compound according to claim 15, wherein Q represents a halogen.

17. The process for preparing a compound according to claim 15, wherein Q represents an iodine atom.

* * * * *